United States Patent
Pearson et al.

(10) Patent No.: US 12,201,349 B2
(45) Date of Patent: Jan. 21, 2025

(54) CONGESTIVE OBSTRUCTION PULMONARY DISEASE (COPD)

(71) Applicant: AngioDynamics, Inc., Latham, NY (US)

(72) Inventors: Robert Pearson, San Jose, CA (US); Mark Ortiz, San Jose, CA (US); Peter Callas, Castro Valley, CA (US)

(73) Assignee: AngioDynamics, Inc., Latham, NY (US)

( * ) Notice: Subject to any disclaimer, the term of this patent is extended or adjusted under 35 U.S.C. 154(b) by 1124 days.

(21) Appl. No.: 17/074,867

(22) Filed: Oct. 20, 2020

(65) Prior Publication Data

US 2021/0030470 A1    Feb. 4, 2021

Related U.S. Application Data

(63) Continuation of application No. 14/948,696, filed on Nov. 23, 2015, now Pat. No. 10,813,688, which is a
(Continued)

(51) Int. Cl.
*A61B 18/18*    (2006.01)
*A61B 18/12*    (2006.01)
(Continued)

(52) U.S. Cl.
CPC ......... *A61B 18/1492* (2013.01); *A61M 25/10* (2013.01); *A61N 1/0519* (2013.01);
(Continued)

(58) Field of Classification Search
CPC .... A61B 2034/2055; A61B 2034/2063; A61B 2090/365; A61B 2090/3937; A61B 34/20;
(Continued)

(56) References Cited

U.S. PATENT DOCUMENTS 1,329,496 A    2/1920    Binkley
1,351,661 A    8/1920    Kaufman
(Continued)

FOREIGN PATENT DOCUMENTS

AU    7656800 A    4/2001
AU    2002315095 A1    12/2002
(Continued)

OTHER PUBLICATIONS

Gowrishankar et al., An Approach to electrical modeling of single and multiple cells, Mar. 18, 2003, PNAS, vol. 100 No. 6, pp. 3203-3208.
(Continued)

*Primary Examiner* — Michael F Peffley
*Assistant Examiner* — Amanda L Zink
(74) *Attorney, Agent, or Firm* — Kevin P. Radigan, Esq.; Heslin Rothenberg Farley & Mesiti P.C.

(57) ABSTRACT

A method for treating Chronic Obstructive Pulmonary Disease (COPD) or chronic bronchitis to alleviate the discomforts of breathing by using non-thermal electroporation energy to ablate diseased portions of the lung including the bronchus, airways and alveoli which, in effect, opens the restrictive diseased portions thereby maximizing the overall surface area thereof causing improved airflow and uninhibited breathing.

18 Claims, 12 Drawing Sheets

Related U.S. Application Data continuation of application No. 14/147,162, filed on Jan. 3, 2014, now Pat. No. 9,295,516, which is a continuation of application No. 12/754,210, filed on Apr. 5, 2010, now Pat. No. 8,632,534.

(60) Provisional application No. 61/166,386, filed on Apr. 3, 2009.

(51) Int. Cl.
| | |
|---|---|
| *A61B 18/14* | (2006.01) |
| *A61M 25/10* | (2013.01) |
| *A61N 1/05* | (2006.01) |
| *A61N 1/32* | (2006.01) |
| *A61B 17/00* | (2006.01) |
| *A61B 18/00* | (2006.01) |

(52) U.S. Cl.
CPC .... *A61N 1/327* (2013.01); *A61B 2017/00176* (2013.01); *A61B 2018/00214* (2013.01); *A61B 2018/0022* (2013.01); *A61B 2018/00541* (2013.01); *A61B 2018/00577* (2013.01); *A61B 2018/00613* (2013.01); *A61B 2018/00898* (2013.01); *A61B 2018/1425* (2013.01); *A61B 18/1477* (2013.01)

(58) Field of Classification Search
CPC ......... A61B 34/32; A61B 34/35; A61B 34/37; A61B 50/13; A61B 90/36; B25J 5/007; B25J 9/162; G05D 1/0231; G05D 1/0274; G05D 1/0282
See application file for complete search history.

(56) References Cited

U.S. PATENT DOCUMENTS

| | | |
|---|---|---|
| 1,376,652 A | 5/1921 | Henry |
| 1,380,272 A | 5/1921 | Tomasulo |
| 1,430,015 A | 9/1922 | Icher |
| 1,437,941 A | 12/1922 | Hoover |
| 1,442,697 A | 1/1923 | Orthmann |
| 1,443,360 A | 1/1923 | Grace |
| 1,445,198 A | 2/1923 | Bornmann |
| 1,450,391 A | 4/1923 | Shaw |
| 1,653,819 A | 12/1927 | Northcott |
| 3,437,941 A | 4/1969 | Leary |
| 3,634,460 A | 1/1972 | Nelson |
| 3,639,545 A | 2/1972 | Wilcox |
| 3,730,238 A | 5/1973 | Butler |
| 3,746,004 A | 7/1973 | Jankelson |
| 3,871,359 A | 3/1975 | Pacela |
| 4,016,866 A | 4/1977 | Lawton |
| 4,016,886 A | 4/1977 | Doss |
| 4,037,341 A | 7/1977 | Herbert |
| 4,216,860 A | 8/1980 | Heimann |
| 4,224,949 A | 9/1980 | Scott |
| 4,226,246 A | 10/1980 | Fragnet |
| 4,262,672 A | 4/1981 | Kief |
| 4,267,047 A | 5/1981 | Henne |
| 4,278,092 A | 7/1981 | Borsanyi et al. |
| 4,299,217 A | 11/1981 | Sagae et al. |
| 4,304,239 A | 12/1981 | Perlin |
| 4,311,148 A | 1/1982 | Courtney |
| 4,336,881 A | 6/1982 | Babb et al. |
| 4,344,436 A | 8/1982 | Kubota |
| 4,392,855 A | 7/1983 | Oreopoulos |
| 4,406,827 A | 9/1983 | Carim |
| 4,407,943 A | 10/1983 | Cole |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek |
| 4,636,199 A | 1/1987 | Victor |
| 4,676,258 A | 6/1987 | Inokuchi |
| 4,676,782 A | 6/1987 | Yamamoto |
| 4,687,471 A | 8/1987 | Twardowski |
| 4,716,896 A | 1/1988 | Ackerman |
| 4,723,549 A | 2/1988 | Wholey |
| D294,519 S | 3/1988 | Hardy, Jr. |
| 4,756,838 A | 7/1988 | Veltman |
| 4,772,269 A | 9/1988 | Twardowski |
| 4,798,585 A | 1/1989 | Inoue |
| 4,810,963 A | 3/1989 | Blake-Coleman |
| 4,813,929 A | 3/1989 | Semrad |
| 4,819,637 A | 4/1989 | Dormandy, Jr. |
| 4,822,470 A | 4/1989 | Chang |
| 4,836,204 A | 6/1989 | Landymore |
| 4,840,172 A | 6/1989 | Augustine |
| 4,863,426 A | 9/1989 | Ferragamo |
| 4,885,003 A | 12/1989 | Hillstead |
| 4,886,496 A | 12/1989 | Conoscenti |
| 4,886,502 A | 12/1989 | Poirier et al. |
| 4,889,634 A | 12/1989 | El-Rashidy |
| 4,903,707 A | 2/1990 | Knute |
| 4,907,601 A | 3/1990 | Frick |
| 4,919,148 A | 4/1990 | Muccio |
| 4,921,484 A | 4/1990 | Muccio |
| 4,946,793 A | 8/1990 | Marshall, III |
| 4,981,477 A | 1/1991 | Schon |
| 4,986,810 A | 1/1991 | Semrad |
| 4,987,895 A | 1/1991 | Heimlich |
| 5,019,034 A | 5/1991 | Weaver |
| 5,031,775 A | 7/1991 | Corp |
| 5,052,391 A | 10/1991 | Silberstone |
| 5,053,013 A | 10/1991 | Ensminger |
| 5,058,605 A | 10/1991 | Slovak |
| 5,071,558 A | 12/1991 | Itob |
| 5,098,843 A | 3/1992 | Calvin |
| 5,134,070 A | 7/1992 | Casnig |
| 5,137,517 A | 8/1992 | Loney |
| 5,141,499 A | 8/1992 | Zappacosta |
| D329,496 S | 9/1992 | Wotton |
| 5,156,597 A | 10/1992 | Verreet |
| 5,173,158 A | 12/1992 | Schmukler |
| 5,186,715 A | 2/1993 | Phillips |
| 5,186,800 A | 2/1993 | Dower |
| 5,188,592 A | 2/1993 | Hakki |
| 5,190,541 A | 3/1993 | Abele |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King |
| 5,242,415 A | 9/1993 | Kantrowitz et al. |
| 5,273,525 A | 12/1993 | Hofmann |
| D343,687 S | 1/1994 | Houghton |
| 5,277,201 A | 1/1994 | Stern |
| 5,279,564 A | 1/1994 | Taylor |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross |
| 5,318,563 A | 6/1994 | Malis |
| 5,328,451 A | 7/1994 | Davis |
| 5,334,167 A | 8/1994 | Cocanower |
| 5,348,554 A | 9/1994 | Imran |
| D351,661 S | 10/1994 | Fischer |
| 5,389,069 A | 2/1995 | Weaver |
| 5,391,158 A | 2/1995 | Peters |
| 5,403,311 A | 4/1995 | Abele |
| 5,405,320 A | 4/1995 | Twardowski et al. |
| 5,417,687 A | 5/1995 | Nardella |
| 5,424,752 A | 6/1995 | Yamazaki |
| 5,425,752 A | 6/1995 | Vu Nguyen |
| 5,439,440 A | 8/1995 | Hofmann |
| 5,439,444 A | 8/1995 | Andersen |
| 5,458,597 A | 10/1995 | Edwards |

(56) References Cited

U.S. PATENT DOCUMENTS

| | | | |
|---|---|---|---|
| 5,458,625 A | 10/1995 | Kendall |
| 5,462,521 A | 10/1995 | Brucker |
| 5,462,644 A | 10/1995 | Woodson |
| 5,484,400 A | 1/1996 | Edwards |
| 5,484,401 A | 1/1996 | Rodriguez |
| 5,533,999 A | 7/1996 | Hood |
| 5,536,240 A | 7/1996 | Edwards |
| 5,536,267 A | 7/1996 | Edwards |
| 5,540,737 A | 7/1996 | Fenn |
| 5,542,916 A | 8/1996 | Hirsch |
| 5,546,940 A | 8/1996 | Panescu et al. |
| 5,575,811 A | 11/1996 | Reid |
| D376,652 S | 12/1996 | Hunt |
| 5,582,588 A | 12/1996 | Sakurai et al. |
| 5,588,424 A | 12/1996 | Insler |
| 5,588,960 A | 12/1996 | Edwards et al. |
| 5,599,311 A | 2/1997 | Raulerson |
| 5,616,126 A | 4/1997 | Malekmehr |
| 5,620,479 A | 4/1997 | Diederich |
| 5,626,146 A | 5/1997 | Barber |
| 5,630,426 A | 5/1997 | Eggers et al. |
| D380,272 S | 6/1997 | Partika |
| 5,634,899 A | 6/1997 | Shapland |
| 5,643,197 A | 7/1997 | Brucker |
| 5,645,855 A | 7/1997 | Lorenz |
| 5,653,684 A | 8/1997 | Laptewicz |
| 5,672,173 A | 9/1997 | Gough |
| 5,672,174 A | 9/1997 | Gough |
| 5,674,267 A | 10/1997 | Mir |
| 5,681,282 A | 10/1997 | Eggers |
| 5,683,384 A | 11/1997 | Zomed |
| 5,687,723 A | 11/1997 | Avitall |
| 5,690,620 A | 11/1997 | Knott |
| 5,697,905 A | 12/1997 | D'Ambrosio |
| 5,700,252 A | 12/1997 | Klingenstein |
| 5,702,359 A | 12/1997 | Hofmann |
| 5,707,332 A | 1/1998 | Weinberger |
| 5,718,246 A | 2/1998 | Vona |
| 5,720,921 A | 2/1998 | Meserol |
| 5,728,143 A | 3/1998 | Gough |
| 5,735,847 A | 4/1998 | Gough et al. |
| 5,749,914 A | 5/1998 | Janssen |
| 5,752,939 A | 5/1998 | Makoto |
| 5,759,158 A * | 6/1998 | Swanson ............... A61B 5/6858 |
| | | | 600/508 |
| 5,778,894 A | 7/1998 | Dorogi |
| 5,782,827 A | 7/1998 | Gough et al. |
| 5,782,882 A | 7/1998 | Lerman |
| 5,800,378 A | 9/1998 | Edwards |
| 5,800,484 A | 9/1998 | Gough et al. |
| 5,807,272 A | 9/1998 | Kun et al. |
| 5,807,306 A | 9/1998 | Shapland |
| 5,807,395 A | 9/1998 | Mulier |
| 5,810,742 A | 9/1998 | Pearlman |
| 5,810,762 A | 9/1998 | Hofmann |
| 5,810,804 A | 9/1998 | Gough |
| 5,830,184 A | 11/1998 | Basta |
| 5,836,897 A | 11/1998 | Sakurai et al. |
| 5,836,905 A | 11/1998 | Lemelson |
| 5,843,026 A | 12/1998 | Edwards |
| 5,843,182 A | 12/1998 | Goldstein |
| 5,856,081 A | 1/1999 | Fahy |
| 5,863,290 A | 1/1999 | Gough et al. |
| 5,865,787 A | 2/1999 | Shapland et al. |
| 5,866,756 A | 2/1999 | Giros et al. |
| 5,868,708 A | 2/1999 | Hart |
| 5,873,849 A | 2/1999 | Bernard |
| 5,873,877 A | 2/1999 | McGaffigan |
| 5,904,648 A | 5/1999 | Arndt et al. |
| 5,913,855 A | 6/1999 | Gough et al. |
| 5,919,142 A | 7/1999 | Boone |
| 5,919,191 A | 7/1999 | Lennox et al. |
| 5,921,982 A | 7/1999 | Lesh |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler |
| 5,957,963 A | 9/1999 | Dobak, III |
| 5,968,006 A | 10/1999 | Hofmann |
| 5,983,131 A | 11/1999 | Weaver |
| 5,983,140 A | 11/1999 | Smith |
| 5,984,896 A | 11/1999 | Boyd |
| 5,991,697 A | 11/1999 | Nelson |
| 5,993,466 A | 11/1999 | Yoon |
| 5,999,847 A | 12/1999 | Elstrom |
| 6,004,339 A | 12/1999 | Wijay |
| 6,009,347 A | 12/1999 | Hofmann |
| 6,009,647 A | 1/2000 | Feingold |
| 6,010,452 A | 1/2000 | Harcourt |
| 6,010,613 A | 1/2000 | Walters |
| 6,010,616 A | 1/2000 | Lewis |
| 6,012,885 A | 1/2000 | Taylor |
| 6,016,452 A | 1/2000 | Kasevich |
| 6,023,638 A | 2/2000 | Swanson |
| 6,029,090 A | 2/2000 | Herbst |
| 6,033,402 A | 3/2000 | Tu |
| 6,041,252 A | 3/2000 | Walker et al. |
| 6,043,066 A | 3/2000 | Mangano |
| 6,050,994 A | 4/2000 | Sherman |
| 6,055,453 A | 4/2000 | Hofmann |
| 6,055,456 A | 4/2000 | Gerber |
| 6,059,780 A | 5/2000 | Gough |
| 6,066,134 A | 5/2000 | Eggers et al. |
| 6,068,121 A | 5/2000 | McGlinch |
| 6,068,650 A | 5/2000 | Hofmann |
| 6,071,281 A | 6/2000 | Burnside |
| 6,074,374 A | 6/2000 | Fulton |
| 6,074,389 A | 6/2000 | Levine et al. |
| 6,085,115 A | 7/2000 | Weaver |
| 6,090,016 A | 7/2000 | Kuo |
| 6,090,105 A | 7/2000 | Zepeda et al. |
| 6,090,106 A | 7/2000 | Goble |
| D430,015 S | 8/2000 | Himbert |
| 6,096,035 A | 8/2000 | Sodhi |
| 6,102,885 A | 8/2000 | Bass |
| 6,106,521 A | 8/2000 | Blewett |
| 6,106,524 A | 8/2000 | Eggers et al. |
| 6,109,270 A | 8/2000 | Mah et al. |
| 6,110,192 A | 8/2000 | Ravenscroft et al. |
| 6,113,593 A | 9/2000 | Tu |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton |
| 6,139,544 A | 10/2000 | Mikus |
| 6,139,545 A | 10/2000 | Utley et al. |
| 6,142,992 A | 11/2000 | Cheng |
| 6,150,148 A * | 11/2000 | Nanda ..................... C12M 35/02 |
| | | | 435/173.6 |
| 6,152,923 A | 11/2000 | Ryan |
| 6,159,163 A | 12/2000 | Strauss |
| 6,178,354 B1 | 1/2001 | Gibson |
| D437,941 S | 2/2001 | Frattini |
| 6,193,715 B1 | 2/2001 | Wrublewski et al. |
| 6,198,970 B1 * | 3/2001 | Freed .................. A61N 1/36031 |
| | | | 607/42 |
| 6,200,314 B1 | 3/2001 | Sherman |
| 6,208,893 B1 | 3/2001 | Hofmann |
| 6,210,402 B1 | 4/2001 | Olsen |
| 6,212,433 B1 | 4/2001 | Behl |
| 6,216,034 B1 | 4/2001 | Hofmann |
| 6,219,577 B1 | 4/2001 | Brown, III |
| D442,697 S | 5/2001 | Hajianpour |
| 6,233,490 B1 | 5/2001 | Kasevich |
| 6,235,023 B1 | 5/2001 | Lee |
| D443,360 S | 6/2001 | Haberland |
| 6,241,702 B1 | 6/2001 | Lundquist |
| 6,241,725 B1 | 6/2001 | Cosman |
| D445,198 S | 7/2001 | Frattini |

(56) References Cited

U.S. PATENT DOCUMENTS

| | | | |
|---|---|---|---|
| 6,258,100 B1 | 7/2001 | Alferness | |
| 6,258,249 B1 | 7/2001 | Simpson | |
| 6,261,831 B1 | 7/2001 | Agee | |
| 6,277,114 B1 | 8/2001 | Bullivant et al. | |
| 6,278,895 B1 | 8/2001 | Bernard | |
| 6,284,140 B1 | 9/2001 | Sommermeyer | |
| 6,287,293 B1 | 9/2001 | Jones et al. | |
| 6,287,304 B1 | 9/2001 | Eggers et al. | |
| 6,296,636 B1 | 10/2001 | Cheng | |
| 6,298,726 B1 | 10/2001 | Adachi | |
| 6,300,108 B1 | 10/2001 | Rubinsky et al. | |
| D450,391 S | 11/2001 | Hunt | |
| 6,312,428 B1 | 11/2001 | Eggers | |
| 6,326,177 B1 * | 12/2001 | Schoenbach | A61B 18/1206 600/12 |
| 6,328,689 B1 | 12/2001 | Gonzalez et al. | |
| 6,328,735 B1 | 12/2001 | Curley | |
| 6,330,478 B1 | 12/2001 | Lee | |
| 6,347,247 B1 | 2/2002 | Dev | |
| 6,349,233 B1 | 2/2002 | Adams | |
| 6,351,674 B2 | 2/2002 | Silverstone | |
| 6,375,634 B1 | 4/2002 | Carroll | |
| 6,387,671 B1 | 5/2002 | Rubinsky | |
| 6,398,779 B1 | 6/2002 | Buysse | |
| 6,403,347 B1 | 6/2002 | Bills | |
| 6,403,348 B1 | 6/2002 | Rubinsky | |
| 6,405,732 B1 | 6/2002 | Edwards | |
| 6,419,674 B1 | 7/2002 | Bowser | |
| 6,428,802 B1 | 8/2002 | Atala | |
| 6,437,551 B1 | 8/2002 | Krulevitch | |
| 6,443,952 B1 | 9/2002 | Mulier et al. | |
| 6,463,331 B1 | 10/2002 | Edwards | |
| 6,470,211 B1 | 10/2002 | Ideker | |
| 6,478,793 B1 | 11/2002 | Cosman | |
| 6,482,221 B1 | 11/2002 | Hebert et al. | |
| 6,482,619 B1 | 11/2002 | Rubinsky et al. | |
| 6,485,487 B1 | 11/2002 | Sherman | |
| 6,488,678 B2 | 12/2002 | Sherman | |
| 6,488,680 B1 | 12/2002 | Francischelli et al. | |
| 6,491,706 B1 | 12/2002 | Alferness | |
| 6,493,569 B2 | 12/2002 | Foo | |
| 6,493,592 B1 | 12/2002 | Leonard | |
| 6,497,704 B2 | 12/2002 | Ein-Gal | |
| 6,500,173 B2 | 12/2002 | Underwood | |
| 6,503,248 B1 | 1/2003 | Levine | |
| 6,506,189 B1 | 1/2003 | Rittman, III et al. | |
| 6,520,183 B2 | 2/2003 | Amar | |
| 6,526,320 B2 | 2/2003 | Mitchell | |
| D471,640 S | 3/2003 | McMichael | |
| D471,641 S | 3/2003 | McMichael | |
| 6,530,922 B2 | 3/2003 | Cosman | |
| 6,533,784 B2 | 3/2003 | Truckai | |
| 6,537,976 B1 | 3/2003 | Gupta | |
| 6,540,695 B1 | 4/2003 | Burbank | |
| 6,558,378 B2 | 5/2003 | Sherman | |
| 6,562,604 B2 | 5/2003 | Rubinsky | |
| 6,569,162 B2 | 5/2003 | He | |
| 6,575,967 B1 | 6/2003 | Leveen | |
| 6,575,969 B1 | 6/2003 | Rittman, III | |
| 6,589,161 B2 | 7/2003 | Corcoran | |
| 6,589,174 B1 | 7/2003 | College | |
| 6,592,594 B2 | 7/2003 | Rimbaugh et al. | |
| 6,607,529 B1 | 8/2003 | Jones | |
| 6,610,054 B1 | 8/2003 | Edwards | |
| 6,611,706 B2 | 8/2003 | Avrahami | |
| 6,613,211 B1 | 9/2003 | McCormick et al. | |
| 6,616,657 B2 | 9/2003 | Simpson | |
| 6,627,421 B1 | 9/2003 | Unger et al. | |
| D480,816 S | 10/2003 | McMichael | |
| 6,638,253 B2 | 10/2003 | Breznock | |
| 6,638,275 B1 | 10/2003 | McGaffigan | |
| 6,653,091 B1 | 11/2003 | Dunn | |
| 6,666,858 B2 | 12/2003 | Lafontaine | |
| 6,669,691 B1 | 12/2003 | Taimisto | |
| 6,673,070 B2 | 1/2004 | Edwards et al. | |
| 6,678,558 B1 | 1/2004 | Dimmer et al. | |
| 6,682,501 B1 | 1/2004 | Nelson | |
| 6,689,096 B1 | 2/2004 | Loubens et al. | |
| 6,689,127 B1 | 2/2004 | Gough et al. | |
| 6,692,493 B2 | 2/2004 | McGovern | |
| 6,694,170 B1 | 2/2004 | Mikus | |
| 6,694,964 B2 | 2/2004 | Wu | |
| 6,694,979 B2 | 2/2004 | Deem | |
| 6,694,984 B2 | 2/2004 | Habib | |
| 6,695,861 B1 | 2/2004 | Rosenberg | |
| 6,697,669 B2 | 2/2004 | Dev | |
| 6,697,670 B2 | 2/2004 | Chomenky | |
| 6,702,808 B1 | 3/2004 | Kreindel | |
| 6,712,811 B2 | 3/2004 | Underwood | |
| D489,973 S | 5/2004 | Root | |
| 6,733,516 B2 | 5/2004 | Simons | |
| 6,753,171 B2 | 6/2004 | Karube | |
| 6,761,716 B2 | 7/2004 | Kadhiresan | |
| 6,770,070 B1 | 8/2004 | Balbierz | |
| D495,807 S | 9/2004 | Agbodoe | |
| 6,795,728 B2 * | 9/2004 | Chornenky | A61N 1/328 607/2 |
| 6,801,804 B2 | 10/2004 | Miller | |
| 6,812,204 B1 | 11/2004 | McHale | |
| 6,837,886 B2 | 1/2005 | Collins | |
| 6,847,848 B2 | 1/2005 | Sterzer | |
| 6,860,847 B2 | 3/2005 | Alferness | |
| 6,865,416 B2 | 3/2005 | Dev | |
| 6,869,430 B2 | 3/2005 | Balbierz | |
| 6,881,213 B2 | 4/2005 | Ryan | |
| 6,892,099 B2 | 5/2005 | Jaafar | |
| 6,895,267 B2 | 5/2005 | Panescu | |
| 6,905,480 B2 | 6/2005 | McGuckin, Jr. | |
| 6,912,417 B1 | 6/2005 | Bernard | |
| 6,926,713 B2 | 8/2005 | Rioux | |
| 6,927,049 B2 | 8/2005 | Rubinsky | |
| 6,941,950 B2 | 9/2005 | Wilson | |
| 6,942,681 B2 | 9/2005 | Johnson | |
| 6,958,062 B1 | 10/2005 | Gough | |
| 6,960,189 B2 | 11/2005 | Bates | |
| 6,972,013 B1 | 12/2005 | Zhang | |
| 6,972,014 B2 | 12/2005 | Eum | |
| 6,994,689 B1 | 2/2006 | Zadno-Azizi | |
| 6,994,706 B2 | 2/2006 | Chornenky | |
| 7,008,421 B2 | 3/2006 | Daniel | |
| 7,011,094 B2 | 3/2006 | Rapacki | |
| 7,012,061 B1 | 3/2006 | Reiss | |
| 7,036,510 B2 | 5/2006 | Zgoda | |
| 7,053,063 B2 | 5/2006 | Rubinsky | |
| 7,054,665 B2 | 5/2006 | Turner | |
| 7,054,685 B2 | 5/2006 | Dimmer | |
| 7,063,698 B2 | 6/2006 | Whayne | |
| 7,087,040 B2 | 8/2006 | McGuckin, Jr. | |
| 7,097,612 B2 | 8/2006 | Bertolero | |
| 7,100,616 B2 | 9/2006 | Springmeyer | |
| 7,113,821 B1 * | 9/2006 | Sun | A61B 5/14514 606/29 |
| 7,130,697 B2 | 10/2006 | Chornenky | |
| 7,162,303 B2 | 1/2007 | Levin | |
| 7,169,107 B2 | 1/2007 | Jersey-Willuhn | |
| 7,211,083 B2 | 5/2007 | Chornenky | |
| 7,232,437 B2 | 6/2007 | Berman | |
| D549,332 S | 8/2007 | Matsumoto | |
| 7,257,450 B2 | 8/2007 | Auth | |
| 7,267,676 B2 | 9/2007 | Chornenky et al. | |
| 7,291,146 B2 | 11/2007 | Steinke | |
| 7,331,940 B2 | 2/2008 | Sommerich | |
| 7,331,949 B2 | 2/2008 | Marisi | |
| 7,341,558 B2 | 3/2008 | De La Torre | |
| 7,344,533 B2 | 3/2008 | Pearson | |
| D565,743 S | 4/2008 | Phillips | |
| D571,478 S | 6/2008 | Horacek | |
| 7,387,626 B2 | 6/2008 | Edwards | |
| 7,399,747 B1 | 7/2008 | Clair | |
| D575,399 S | 8/2008 | Matsumoto | |
| D575,402 S | 8/2008 | Sandor | |
| 7,412,977 B2 | 8/2008 | Fields | |
| 7,419,487 B2 | 9/2008 | Johnson | |
| 7,434,578 B2 | 10/2008 | Dillard | |

(56) References Cited

U.S. PATENT DOCUMENTS

| | | | |
|---|---|---|---|
| 7,437,194 B2 | 10/2008 | Skwarek |
| 7,449,019 B2 | 11/2008 | Uchida |
| 7,451,765 B2 | 11/2008 | Adler |
| 7,455,675 B2 | 11/2008 | Schur |
| 7,476,203 B2 | 1/2009 | Devore |
| 7,488,292 B2 | 2/2009 | Adachi |
| 7,520,877 B2 | 4/2009 | Lee, Jr. |
| 7,533,671 B2 | 5/2009 | Gonzalez |
| D595,422 S | 6/2009 | Mustapha |
| 7,544,301 B2 | 6/2009 | Shah |
| 7,549,984 B2 | 6/2009 | Mathis |
| 7,553,309 B2 | 6/2009 | Buysse |
| 7,565,208 B2 | 7/2009 | Harris |
| 7,571,729 B2 | 8/2009 | Saadat |
| 7,617,005 B2 | 11/2009 | Demarais |
| 7,620,451 B2 | 11/2009 | Demarais |
| 7,620,507 B2 | 11/2009 | Richardson |
| 7,632,291 B2 | 12/2009 | Stephens |
| 7,647,115 B2 | 1/2010 | Levin |
| 7,653,438 B2 | 1/2010 | Deem |
| 7,655,004 B2 * | 2/2010 | Long ............... A61B 1/06 600/103 |
| 7,670,333 B2 | 3/2010 | Schatzberger |
| 7,674,249 B2 | 3/2010 | Ivorra |
| 7,680,543 B2 | 3/2010 | Azure |
| D613,418 S | 4/2010 | Ryan |
| 7,699,842 B2 | 4/2010 | Buysse |
| 7,706,865 B1 | 4/2010 | Snell |
| 7,717,948 B2 | 5/2010 | Demarais |
| 7,718,409 B2 | 5/2010 | Rubinsky |
| 7,722,606 B2 | 5/2010 | Azure |
| 7,742,795 B2 | 6/2010 | Stone |
| 7,763,018 B2 | 7/2010 | DeCarlo |
| 7,765,010 B2 | 7/2010 | Chornenky |
| 7,771,401 B2 | 8/2010 | Hekmat |
| 7,776,035 B2 | 8/2010 | Rick |
| 7,815,571 B2 | 10/2010 | Deckman |
| 7,815,662 B2 | 10/2010 | Spivey |
| 7,824,870 B2 | 11/2010 | Kovalcheck |
| RE42,016 E | 12/2010 | Chornenky et al. |
| 7,846,108 B2 | 12/2010 | Turovskiy |
| 7,853,333 B2 | 12/2010 | Demarais |
| D630,321 S | 1/2011 | Hamilton, Jr. |
| D631,154 S | 1/2011 | Hamilton, Jr. |
| 7,874,986 B2 | 1/2011 | Deckman |
| 7,875,025 B2 | 1/2011 | Cockburn |
| 7,879,031 B2 | 2/2011 | Peterson |
| RE42,277 E | 4/2011 | Jaafar et al. |
| 7,918,852 B2 | 4/2011 | Tullis |
| 7,937,143 B2 | 5/2011 | Demarais |
| 7,938,824 B2 | 5/2011 | Chornenky |
| 7,951,582 B2 | 5/2011 | Gazit |
| 7,955,827 B2 | 6/2011 | Rubinsky |
| RE42,835 E | 10/2011 | Chornenky et al. |
| D647,628 S | 10/2011 | Helfteren |
| 8,029,504 B2 * | 10/2011 | Long ............... A61B 1/018 600/103 |
| 8,037,591 B2 | 10/2011 | Spivey |
| 8,048,067 B2 | 11/2011 | Davalos |
| 8,052,604 B2 | 11/2011 | Lau |
| 8,057,391 B2 | 11/2011 | Lau |
| 8,062,290 B2 | 11/2011 | Buysse |
| RE43,009 E | 12/2011 | Chornenky |
| 8,070,759 B2 | 12/2011 | Stefanchik |
| 8,075,572 B2 | 12/2011 | Stefanchik |
| 8,088,072 B2 | 1/2012 | Munrow |
| 8,100,922 B2 | 1/2012 | Griffith |
| 8,109,926 B2 | 2/2012 | Azure |
| 8,114,070 B2 | 2/2012 | Rubinsky |
| 8,114,072 B2 | 2/2012 | Long |
| 8,114,119 B2 | 2/2012 | Spivey |
| 8,131,371 B2 | 3/2012 | Demarals |
| 8,131,372 B2 | 3/2012 | Levin |
| 8,145,316 B2 | 3/2012 | Deem |
| 8,145,317 B2 | 3/2012 | Demarais |
| 8,150,518 B2 | 4/2012 | Levin |
| 8,150,519 B2 | 4/2012 | Demarais |
| 8,150,520 B2 | 4/2012 | Demarais |
| 8,154,288 B2 | 4/2012 | Deimling |
| 8,157,834 B2 | 4/2012 | Conlon |
| 8,162,918 B2 | 4/2012 | Ivorra |
| 8,172,772 B2 | 5/2012 | Zwolinski |
| 8,174,267 B2 | 5/2012 | Brannan |
| 8,175,711 B2 | 5/2012 | Demarais |
| 8,180,433 B2 | 5/2012 | Brannan |
| 8,181,995 B2 | 5/2012 | Decarlo |
| 8,182,477 B2 | 5/2012 | Orszulak |
| 8,187,269 B2 * | 5/2012 | Shadduck ............... A61B 18/04 606/41 |
| 8,187,270 B2 | 5/2012 | Auth |
| 8,206,300 B2 | 6/2012 | Deckman |
| 8,211,097 B2 | 7/2012 | Leyh |
| 8,211,099 B2 | 7/2012 | Buysse |
| 8,211,125 B2 | 7/2012 | Spivey |
| 8,216,161 B2 | 7/2012 | Darlington |
| 8,221,411 B2 | 7/2012 | Francischelli |
| 8,231,603 B2 | 7/2012 | Hobbs |
| 8,240,468 B2 | 8/2012 | Wilkinson |
| 8,241,204 B2 | 8/2012 | Spivey |
| 8,242,782 B2 | 8/2012 | Brannan |
| 8,246,615 B2 | 8/2012 | Behnke |
| 8,248,075 B2 | 8/2012 | Brannan |
| 8,251,986 B2 * | 8/2012 | Chornenky ........ A61B 18/1206 606/41 |
| 8,252,057 B2 | 8/2012 | Fox |
| 8,262,563 B2 | 9/2012 | Bakos |
| 8,262,577 B2 | 9/2012 | Munrow |
| 8,262,655 B2 | 9/2012 | Ghabrial |
| 8,262,680 B2 | 9/2012 | Swain |
| 8,267,884 B1 | 9/2012 | Hicks |
| 8,267,927 B2 | 9/2012 | Dalal |
| 8,267,936 B2 | 9/2012 | Hushka |
| 8,277,379 B2 | 10/2012 | Lau |
| 8,282,631 B2 | 10/2012 | Davalos |
| 8,287,527 B2 | 10/2012 | Brannan |
| 8,292,880 B2 | 10/2012 | Prakash |
| 8,298,222 B2 | 10/2012 | Rubinsky |
| 8,303,516 B2 | 11/2012 | Schmitz |
| 8,317,806 B2 | 11/2012 | Coe |
| 8,337,394 B2 | 12/2012 | Vakharia |
| 8,343,144 B2 | 1/2013 | Kleyman |
| 8,346,370 B2 | 1/2013 | Haley |
| 8,347,891 B2 | 1/2013 | Demarais |
| 8,348,921 B2 | 1/2013 | Ivorra |
| 8,348,938 B2 | 1/2013 | Blomgren |
| 8,353,487 B2 | 1/2013 | Trusty |
| 8,353,902 B2 | 1/2013 | Prakash |
| 8,361,006 B2 | 1/2013 | Kraemer |
| 8,361,066 B2 | 1/2013 | Long |
| 8,361,112 B2 | 1/2013 | Carroll, II |
| 8,366,712 B2 | 2/2013 | Bleich |
| 8,377,057 B2 | 2/2013 | Rick |
| 8,380,283 B2 | 2/2013 | Krieg |
| D677,798 S | 3/2013 | Hart |
| 8,394,092 B2 | 3/2013 | Brannan |
| 8,394,102 B2 | 3/2013 | Garabedian |
| 8,398,626 B2 | 3/2013 | Buysse |
| 8,398,641 B2 | 3/2013 | Wallace |
| 8,403,924 B2 | 3/2013 | Behnke |
| 8,403,926 B2 | 3/2013 | Nobis |
| 8,409,200 B2 | 4/2013 | Holcomb |
| 8,409,206 B2 | 4/2013 | Wallace |
| 8,417,328 B2 | 4/2013 | Sarfaty |
| 8,425,455 B2 | 4/2013 | Nentwick |
| 8,425,505 B2 | 4/2013 | Long |
| 8,433,423 B2 | 4/2013 | Demarais |
| 8,437,845 B2 | 5/2013 | Sarfaty |
| 8,439,907 B2 | 5/2013 | Auth |
| 8,444,640 B2 | 5/2013 | Demarais |
| 8,449,538 B2 | 5/2013 | Long |
| 8,454,594 B2 | 6/2013 | Demarais |
| 8,465,464 B2 | 6/2013 | Travis |
| 8,465,484 B2 | 6/2013 | Davalos |
| 8,469,716 B2 | 6/2013 | Fedotov |

(56) References Cited

U.S. PATENT DOCUMENTS

| | | |
|---|---|---|
| 8,473,067 B2 | 6/2013 | Hastings |
| 8,480,657 B2 | 7/2013 | Bakos |
| 8,480,665 B2 | 7/2013 | Decarlo |
| 8,480,666 B2 | 7/2013 | Buysse |
| 8,480,689 B2 | 7/2013 | Spivey |
| 8,489,192 B1 | 7/2013 | Hlavka |
| 8,496,574 B2 | 7/2013 | Trusty |
| 8,506,485 B2 | 8/2013 | Deckman |
| 8,506,564 B2 | 8/2013 | Long |
| 8,511,317 B2 | 8/2013 | Thapliyal |
| 8,512,329 B2 | 8/2013 | Paulus |
| 8,512,330 B2 | 8/2013 | Epstein |
| 8,518,031 B2 | 8/2013 | Boyden |
| 8,529,563 B2 | 9/2013 | Long |
| 8,542,019 B2 | 9/2013 | Brannan |
| 8,546,979 B2 | 10/2013 | Heeren |
| 8,548,600 B2 | 10/2013 | Deem |
| 8,551,069 B2 | 10/2013 | Demarais |
| 8,551,088 B2 | 10/2013 | Falkenstein |
| 8,551,097 B2 | 10/2013 | Schmitz |
| 8,562,588 B2 | 10/2013 | Hobbs |
| 8,562,598 B2 | 10/2013 | Falkenstein |
| 8,562,599 B2 | 10/2013 | Leyh |
| 8,562,602 B2 | 10/2013 | Azure |
| 8,568,401 B2 | 10/2013 | Brannan |
| 8,568,402 B2 | 10/2013 | Buysse |
| 8,568,404 B2 | 10/2013 | Brannan |
| 8,568,410 B2 | 10/2013 | Vakharia |
| 8,568,411 B2 | 10/2013 | Falkenstein |
| 8,579,894 B2 | 11/2013 | Falkenstein |
| 8,579,897 B2 | 11/2013 | Vakharia |
| 8,579,902 B2 | 11/2013 | Bleich |
| 8,585,704 B2 | 11/2013 | Schmitz |
| 8,603,087 B2 | 12/2013 | Rubinsky |
| 8,608,652 B2 | 12/2013 | Voegele |
| 8,608,739 B2 | 12/2013 | Sartor |
| 8,613,745 B2 | 12/2013 | Bleich |
| 8,617,163 B2 | 12/2013 | Bleich |
| 8,620,423 B2 | 12/2013 | Demarais |
| 8,626,300 B2 | 1/2014 | Demarais |
| 8,632,534 B2 | 1/2014 | Pearson |
| 8,634,929 B2 | 1/2014 | Chornenky |
| 8,647,338 B2 | 2/2014 | Chornenky |
| 8,647,346 B2 | 2/2014 | Bleich |
| 8,652,130 B2 | 2/2014 | Kreindel |
| 8,652,138 B2 | 2/2014 | Bleich |
| 8,652,150 B2 | 2/2014 | Swain |
| 8,663,210 B2 | 3/2014 | Tomasello |
| 8,663,228 B2 | 3/2014 | Schmitz |
| 8,668,688 B2 | 3/2014 | Rusin |
| 8,672,937 B2 | 3/2014 | Decarlo |
| 8,679,003 B2 | 3/2014 | Spivey |
| 8,684,998 B2 | 4/2014 | Demarais |
| 8,702,697 B2 | 4/2014 | Curley |
| 8,706,258 B2 | 4/2014 | Nabors, Sr. |
| 8,712,500 B2 | 4/2014 | Schmidt |
| 8,715,276 B2 | 5/2014 | Thompson |
| 8,721,637 B2 | 5/2014 | Zarins |
| 8,725,249 B2 | 5/2014 | Bar-Yoseph |
| 8,728,137 B2 | 5/2014 | Zarins |
| 8,728,138 B2 | 5/2014 | Zarins |
| 8,728,139 B2 | 5/2014 | Azure |
| 8,731,672 B2 | 5/2014 | Hlavka |
| 8,740,895 B2 | 6/2014 | Mayse |
| 8,740,896 B2 | 6/2014 | Zarins |
| 8,753,335 B2 | 6/2014 | Moshe |
| 8,768,470 B2 | 7/2014 | Deem |
| 8,771,252 B2 | 7/2014 | Gelfand |
| 8,771,260 B2 | 7/2014 | Conlon |
| 8,774,913 B2 | 7/2014 | Demarais |
| 8,774,922 B2 | 7/2014 | Zarins |
| 8,777,943 B2 | 7/2014 | Mayse |
| 8,784,463 B2 | 7/2014 | Zarins |
| 8,797,039 B2 | 8/2014 | Brannan |
| 8,801,626 B2 | 8/2014 | Sun |
| 8,805,545 B2 | 8/2014 | Zarins |
| 8,808,280 B2 | 8/2014 | Mayse |
| 8,814,860 B2 | 8/2014 | Davalos |
| 8,818,514 B2 | 8/2014 | Zarins |
| 8,821,489 B2 | 9/2014 | Mayse |
| 8,828,031 B2 | 9/2014 | Fox |
| 8,835,166 B2 | 9/2014 | Phillips |
| 8,845,559 B2 | 9/2014 | Darlington |
| 8,845,629 B2 | 9/2014 | Demarais |
| 8,845,635 B2 | 9/2014 | Daniel |
| 8,845,639 B2 | 9/2014 | Wallace |
| 8,852,163 B2 | 10/2014 | Deem |
| 8,858,550 B2 | 10/2014 | Busch-Madsen |
| 8,865,076 B2 | 10/2014 | Sarfaty |
| 8,880,185 B2 | 11/2014 | Hastings |
| 8,880,186 B2 | 11/2014 | Levin |
| 8,880,195 B2 | 11/2014 | Azure |
| 8,882,759 B2 | 11/2014 | Manley |
| 8,888,792 B2 | 11/2014 | Harris |
| 8,894,641 B2 | 11/2014 | Brannan |
| 8,903,488 B2 | 12/2014 | Callas |
| 8,906,006 B2 | 12/2014 | Chornenky |
| 8,906,011 B2 | 12/2014 | Gelbart |
| 8,906,035 B2 | 12/2014 | Zwolinski |
| 8,911,439 B2 | 12/2014 | Mayse |
| 8,915,910 B2 | 12/2014 | Falkenstein |
| 8,915,911 B2 | 12/2014 | Azure |
| 8,920,411 B2 | 12/2014 | Gelbart |
| 8,923,970 B2 | 12/2014 | Bar-Yoseph |
| 8,926,606 B2 | 1/2015 | Davalos |
| 8,932,287 B2 | 1/2015 | Gelbart |
| 8,932,289 B2 | 1/2015 | Mayse |
| 8,934,978 B2 | 1/2015 | Deem |
| 8,939,897 B2 | 1/2015 | Nobis |
| 8,939,970 B2 | 1/2015 | Stone |
| 8,945,121 B2 | 2/2015 | Curley |
| 8,948,865 B2 | 2/2015 | Zarins |
| 8,956,350 B2 | 2/2015 | Buysse |
| 8,958,871 B2 | 2/2015 | Demarais |
| 8,958,888 B2 | 2/2015 | Chornenky |
| 8,961,507 B2 | 2/2015 | Mayse |
| 8,961,508 B2 | 2/2015 | Mayse |
| 8,968,542 B2 | 3/2015 | Davalos |
| 8,974,451 B2 | 3/2015 | Smith |
| 8,983,595 B2 | 3/2015 | Levin |
| 8,986,294 B2 | 3/2015 | Demarais |
| 8,992,517 B2 | 3/2015 | Davalos |
| 9,005,189 B2 | 4/2015 | Davalos |
| 9,005,195 B2 | 4/2015 | Mayse |
| 9,005,198 B2 | 4/2015 | Long |
| 9,011,431 B2 | 4/2015 | Long |
| 9,017,323 B2 | 4/2015 | Miller |
| 9,017,324 B2 | 4/2015 | Mayse |
| 9,023,034 B2 | 5/2015 | Jenson |
| 9,023,037 B2 | 5/2015 | Zarins |
| 9,028,483 B2 | 5/2015 | Long |
| 9,028,485 B2 | 5/2015 | Edmunds |
| 9,039,702 B2 | 5/2015 | Miller |
| 9,049,987 B2 | 6/2015 | Conlon |
| 9,050,449 B2 | 6/2015 | Darlington |
| 9,060,761 B2 | 6/2015 | Hastings |
| 9,072,518 B2 | 7/2015 | Swanson |
| 9,072,527 B2 | 7/2015 | Deem |
| 9,078,665 B2 | 7/2015 | Moss |
| 9,084,609 B2 | 7/2015 | Smith |
| 9,089,350 B2 | 7/2015 | Willard |
| 9,101,386 B2 | 8/2015 | Wallace |
| 9,108,040 B2 | 8/2015 | Zarins |
| 9,113,888 B2 | 8/2015 | Orszulak |
| 9,119,633 B2 | 9/2015 | Gelbart |
| 9,119,634 B2 | 9/2015 | Gelbart |
| 9,125,643 B2 | 9/2015 | Hlavka |
| 9,125,661 B2 | 9/2015 | Deem |
| 9,125,666 B2 | 9/2015 | Steinke |
| 9,125,667 B2 | 9/2015 | Stone |
| 9,131,978 B2 | 9/2015 | Zarins |
| 9,138,281 B2 | 9/2015 | Zarins |
| 9,138,287 B2 | 9/2015 | Curley |
| 9,138,288 B2 | 9/2015 | Curley |

(56) References Cited

U.S. PATENT DOCUMENTS

| | | |
|---|---|---|
| 9,149,328 B2 | 10/2015 | Dimmer |
| 9,149,331 B2 | 10/2015 | Deem |
| 9,155,589 B2 | 10/2015 | Jenson |
| 9,173,704 B2 | 11/2015 | Hobbs |
| 9,186,198 B2 | 11/2015 | Demarais |
| 9,186,209 B2 | 11/2015 | Weber |
| 9,186,213 B2 | 11/2015 | Deem |
| 9,192,435 B2 | 11/2015 | Jenson |
| 9,192,715 B2 | 11/2015 | Gelfand |
| 9,192,790 B2 | 11/2015 | Hastings |
| 9,198,733 B2 | 12/2015 | Neal, II |
| 9,220,526 B2 | 12/2015 | Conlon |
| 9,220,558 B2 | 12/2015 | Willard |
| 9,220,561 B2 | 12/2015 | Crow |
| 9,226,772 B2 | 1/2016 | Fox |
| 9,226,790 B2 | 1/2016 | Zemel |
| 9,233,241 B2 | 1/2016 | Long |
| 9,247,952 B2 | 2/2016 | Bleich |
| 9,248,318 B2 | 2/2016 | Darlington |
| 9,254,169 B2 | 2/2016 | Long |
| 9,254,172 B2 | 2/2016 | Behnke, II |
| 9,265,557 B2 | 2/2016 | Sherman |
| 9,265,558 B2 | 2/2016 | Zarins |
| 9,276,367 B2 | 3/2016 | Brannan |
| 9,277,955 B2 | 3/2016 | Herscher |
| 9,277,969 B2 | 3/2016 | Brannan |
| 9,283,051 B2 | 3/2016 | Garcia |
| 9,289,255 B2 | 3/2016 | Deem |
| 9,295,516 B2 | 3/2016 | Pearson |
| 9,307,935 B2 | 4/2016 | Pluta |
| 9,308,039 B2 | 4/2016 | Azure |
| 9,308,043 B2 | 4/2016 | Zarins |
| 9,308,044 B2 | 4/2016 | Zarins |
| 9,314,620 B2 | 4/2016 | Long |
| 9,314,630 B2 | 4/2016 | Levin |
| 9,320,561 B2 | 4/2016 | Zarins |
| 9,320,563 B2 | 4/2016 | Brustad |
| 9,326,751 B2 | 5/2016 | Hastings |
| 9,326,817 B2 | 5/2016 | Zarins |
| 9,327,100 B2 | 5/2016 | Perry |
| 9,327,122 B2 | 5/2016 | Zarins |
| 9,339,618 B2 | 5/2016 | Deem |
| 9,351,790 B2 | 5/2016 | Zemel |
| 9,414,881 B2 | 8/2016 | Callas |
| 9,598,691 B2 | 3/2017 | Davalos |
| 9,700,368 B2 | 7/2017 | Callas |
| 9,764,145 B2 | 9/2017 | Callas |
| 9,867,652 B2 | 1/2018 | Sano |
| 9,943,599 B2 | 4/2018 | Gehl |
| 10,010,666 B2 | 7/2018 | Rubinsky |
| 10,117,701 B2 | 11/2018 | Davalos |
| 10,117,707 B2 | 11/2018 | Garcia |
| 10,143,512 B2 | 12/2018 | Rubinsky |
| 10,154,874 B2 | 12/2018 | Davalos |
| 10,238,447 B2 | 3/2019 | Neal, II |
| 10,245,098 B2 | 4/2019 | Davalos |
| 10,245,105 B2 | 4/2019 | Davalos |
| 10,272,178 B2 | 4/2019 | Davalos |
| 10,286,108 B2 | 5/2019 | Davalos |
| 10,292,755 B2* | 5/2019 | Arena ............. A61B 18/14 |
| 10,342,600 B2 | 7/2019 | Callas |
| 10,448,989 B2 | 10/2019 | Arena |
| 10,470,822 B2 | 11/2019 | Garcia |
| 10,471,254 B2 | 11/2019 | Sano |
| 10,537,379 B2 | 1/2020 | Sano |
| 10,668,208 B2 | 6/2020 | Rubinsky |
| 10,694,972 B2 | 6/2020 | Davalos |
| 10,702,326 B2 | 7/2020 | Neal, II |
| 10,828,085 B2 | 11/2020 | Davalos |
| 10,828,086 B2 | 11/2020 | Davalos |
| 10,905,492 B2 | 2/2021 | Neal, II |
| 10,959,772 B2 | 3/2021 | Davalos |
| 11,254,926 B2 | 2/2022 | Garcia |
| 11,272,979 B2 | 3/2022 | Garcia |
| 11,311,329 B2 | 4/2022 | Davalos |
| 11,382,681 B2 | 7/2022 | Arena |
| 11,406,820 B2 | 8/2022 | Sano |
| 11,453,873 B2 | 9/2022 | Davalos |
| 11,607,271 B2 | 3/2023 | Garcia |
| 11,607,537 B2 | 3/2023 | Latouche |
| 11,638,603 B2 | 5/2023 | Sano |
| 11,655,466 B2 | 5/2023 | Neal, II |
| 11,723,710 B2 | 8/2023 | Neal, II |
| 11,737,810 B2 | 8/2023 | Davalos |
| 11,890,046 B2 | 2/2024 | Neal |
| 11,903,690 B2 | 2/2024 | Davalos |
| 11,925,405 B2 | 3/2024 | Davalos |
| 11,974,800 B2 | 5/2024 | Sano |
| 2001/0014819 A1 | 8/2001 | Ingle |
| 2001/0039393 A1 | 11/2001 | Mori |
| 2001/0043706 A1 | 11/2001 | Masuda |
| 2001/0044596 A1 | 11/2001 | Jaafar |
| 2001/0046706 A1 | 11/2001 | Rubinsky |
| 2001/0047167 A1 | 11/2001 | Heggeness |
| 2001/0051366 A1 | 12/2001 | Rubinsky |
| 2002/0002393 A1 | 1/2002 | Mitchell |
| 2002/0010491 A1 | 1/2002 | Schoenbach |
| 2002/0022864 A1 | 2/2002 | Mahvi |
| 2002/0040204 A1 | 4/2002 | Dev |
| 2002/0049370 A1 | 4/2002 | Laufer |
| 2002/0052601 A1 | 5/2002 | Goldberg |
| 2002/0055731 A1 | 5/2002 | Atala |
| 2002/0065541 A1 | 5/2002 | Fredricks |
| 2002/0072742 A1 | 6/2002 | Schaefer |
| 2002/0077314 A1 | 6/2002 | Falk |
| 2002/0077627 A1 | 6/2002 | Johnson |
| 2002/0077676 A1 | 6/2002 | Schroeppel |
| 2002/0082543 A1 | 6/2002 | Park |
| 2002/0091362 A1 | 7/2002 | Maginot |
| 2002/0095197 A1 | 7/2002 | Lardo |
| 2002/0099323 A1 | 7/2002 | Dev |
| 2002/0104318 A1 | 8/2002 | Jaafar |
| 2002/0111615 A1 | 8/2002 | Cosman |
| 2002/0112729 A1 | 8/2002 | Devore |
| 2002/0115208 A1 | 8/2002 | Mitchell |
| 2002/0119437 A1 | 8/2002 | Grooms |
| 2002/0120261 A1 | 8/2002 | Morris |
| 2002/0133324 A1 | 9/2002 | Weaver |
| 2002/0137121 A1 | 9/2002 | Rubinsky |
| 2002/0138075 A1 | 9/2002 | Edwards |
| 2002/0138117 A1 | 9/2002 | Son |
| 2002/0143365 A1 | 10/2002 | Herbst |
| 2002/0147462 A1 | 10/2002 | Mair |
| 2002/0156472 A1 | 10/2002 | Lee |
| 2002/0161361 A1 | 10/2002 | Sherman |
| 2002/0183684 A1 | 12/2002 | Dev |
| 2002/0183735 A1 | 12/2002 | Edwards |
| 2002/0183740 A1 | 12/2002 | Edwards |
| 2002/0188242 A1 | 12/2002 | Wu |
| 2002/0193784 A1 | 12/2002 | McHale |
| 2002/0193831 A1 | 12/2002 | Dewey |
| 2003/0009110 A1 | 1/2003 | Tu |
| 2003/0009165 A1 | 1/2003 | Edwards |
| 2003/0014047 A1 | 1/2003 | Woloszko |
| 2003/0016168 A1 | 1/2003 | Jandrell |
| 2003/0055220 A1 | 3/2003 | Legrain |
| 2003/0055420 A1 | 3/2003 | Kadhiresan |
| 2003/0059945 A1 | 3/2003 | Dzekunov |
| 2003/0060856 A1 | 3/2003 | Chornenky |
| 2003/0074039 A1 | 4/2003 | Puskas |
| 2003/0078490 A1 | 4/2003 | Damasco |
| 2003/0088189 A1 | 5/2003 | Tu |
| 2003/0088199 A1 | 5/2003 | Kawaji |
| 2003/0096407 A1 | 5/2003 | Atala |
| 2003/0105454 A1 | 6/2003 | Cucin |
| 2003/0109871 A1 | 6/2003 | Johnson |
| 2003/0127090 A1 | 7/2003 | Gifford |
| 2003/0130711 A1 | 7/2003 | Pearson |
| 2003/0135242 A1 | 7/2003 | Mongeon |
| 2003/0149451 A1 | 8/2003 | Chomenky |
| 2003/0153960 A1* | 8/2003 | Chornenky ............. A61N 1/327 607/72 |
| 2003/0154988 A1 | 8/2003 | Devore |
| 2003/0164168 A1 | 9/2003 | Shaw |

(56) References Cited

U.S. PATENT DOCUMENTS

| | | |
|---|---|---|
| 2003/0166181 A1 | 9/2003 | Rubinsky |
| 2003/0170898 A1 | 9/2003 | Gundersen |
| 2003/0194808 A1 | 10/2003 | Rubinsky |
| 2003/0195385 A1 | 10/2003 | Devore |
| 2003/0195406 A1 | 10/2003 | Jenkins |
| 2003/0199050 A1 | 10/2003 | Mangano |
| 2003/0208200 A1 | 11/2003 | Palanker |
| 2003/0208236 A1 | 11/2003 | Heil |
| 2003/0212394 A1* | 11/2003 | Pearson .............. A61B 18/1477 606/41 |
| 2003/0212412 A1 | 11/2003 | Dillard |
| 2003/0225360 A1 | 12/2003 | Eppstein |
| 2003/0228344 A1 | 12/2003 | Fields |
| 2003/0233091 A1 | 12/2003 | Whayne |
| 2004/0009459 A1 | 1/2004 | Anderson |
| 2004/0019371 A1 | 1/2004 | Jaafar |
| 2004/0055606 A1 | 3/2004 | Hendricksen |
| 2004/0059328 A1 | 3/2004 | Daniel |
| 2004/0059389 A1 | 3/2004 | Chornenky |
| 2004/0068228 A1 | 4/2004 | Cunningham |
| 2004/0116935 A1 | 6/2004 | Lechot |
| 2004/0116965 A1 | 6/2004 | Falkenberg |
| 2004/0133194 A1 | 7/2004 | Eum |
| 2004/0138715 A1 | 7/2004 | Van Groeningen |
| 2004/0146877 A1 | 7/2004 | Diss |
| 2004/0153057 A1 | 8/2004 | Davison |
| 2004/0167458 A1 | 8/2004 | Draghia-Akli |
| 2004/0172136 A1 | 9/2004 | Ralph |
| 2004/0176855 A1 | 9/2004 | Badylak |
| 2004/0187875 A1 | 9/2004 | He |
| 2004/0193042 A1 | 9/2004 | Scampini |
| 2004/0193097 A1 | 9/2004 | Hofmann |
| 2004/0199159 A1 | 10/2004 | Lee |
| 2004/0200484 A1 | 10/2004 | Springmeyer |
| 2004/0206349 A1 | 10/2004 | Alferness |
| 2004/0210248 A1 | 10/2004 | Gordon |
| 2004/0230187 A1 | 11/2004 | Lee |
| 2004/0236376 A1 | 11/2004 | Miklavcic |
| 2004/0237340 A1 | 12/2004 | Rembrandt |
| 2004/0243107 A1 | 12/2004 | Macoviak |
| 2004/0267189 A1 | 12/2004 | Mavor |
| 2004/0267256 A1 | 12/2004 | Garabedian |
| 2004/0267340 A1 | 12/2004 | Cioanta |
| 2005/0004507 A1 | 1/2005 | Schroeppel |
| 2005/0004567 A1 | 1/2005 | Daniel |
| 2005/0010209 A1 | 1/2005 | Lee |
| 2005/0010259 A1 | 1/2005 | Gerber |
| 2005/0013726 A1 | 1/2005 | Hill |
| 2005/0013870 A1 | 1/2005 | Freyman |
| 2005/0019830 A1 | 1/2005 | Penner |
| 2005/0033276 A1 | 2/2005 | Adachi |
| 2005/0043726 A1 | 2/2005 | McHale |
| 2005/0048651 A1 | 3/2005 | Ryttsen |
| 2005/0049541 A1 | 3/2005 | Behar |
| 2005/0054978 A1 | 3/2005 | Segal |
| 2005/0061322 A1 | 3/2005 | Freitag |
| 2005/0063974 A1 | 3/2005 | Reinhard |
| 2005/0066974 A1 | 3/2005 | Fields |
| 2005/0096537 A1 | 5/2005 | Parel |
| 2005/0096709 A1 | 5/2005 | Skwarek |
| 2005/0107781 A1 | 5/2005 | Ostrovsky |
| 2005/0112141 A1 | 5/2005 | Terman |
| 2005/0135393 A1 | 6/2005 | Benco |
| 2005/0143817 A1 | 6/2005 | Hunter |
| 2005/0165393 A1 | 7/2005 | Eppstein |
| 2005/0171522 A1 | 8/2005 | Christopherson |
| 2005/0171523 A1 | 8/2005 | Rubinsky |
| 2005/0171571 A1 | 8/2005 | Goodin |
| 2005/0171574 A1 | 8/2005 | Rubinsky |
| 2005/0182462 A1 | 8/2005 | Chornenky |
| 2005/0197619 A1 | 9/2005 | Rule |
| 2005/0203489 A1 | 9/2005 | Saadat |
| 2005/0216047 A1 | 9/2005 | Kumoyama |
| 2005/0228373 A1 | 10/2005 | Kelly |
| 2005/0228459 A1 | 10/2005 | Levin |
| 2005/0228460 A1 | 10/2005 | Levin |
| 2005/0234445 A1 | 10/2005 | Conquergood |
| 2005/0234523 A1 | 10/2005 | Levin |
| 2005/0261672 A1* | 11/2005 | Deem ................ A61B 18/1492 606/41 |
| 2005/0261707 A1 | 11/2005 | Schatzberger |
| 2005/0267407 A1 | 12/2005 | Goldman |
| 2005/0282284 A1 | 12/2005 | Rubinsky |
| 2005/0283149 A1 | 12/2005 | Thorne |
| 2005/0288684 A1 | 12/2005 | Aronson |
| 2005/0288702 A1 | 12/2005 | McGurk |
| 2005/0288730 A1 | 12/2005 | Deem |
| 2006/0004356 A1 | 1/2006 | Bilski |
| 2006/0004400 A1 | 1/2006 | McGurk |
| 2006/0009748 A1 | 1/2006 | Mathis |
| 2006/0015147 A1 | 1/2006 | Persson |
| 2006/0020347 A1 | 1/2006 | Barrett |
| 2006/0024359 A1 | 2/2006 | Walker |
| 2006/0025760 A1 | 2/2006 | Podhajsky |
| 2006/0025821 A1 | 2/2006 | Gelfand |
| 2006/0030810 A1 | 2/2006 | Mandrusov |
| 2006/0074413 A1 | 4/2006 | Behzadian |
| 2006/0079838 A1 | 4/2006 | Walker |
| 2006/0079845 A1 | 4/2006 | Howard |
| 2006/0079883 A1 | 4/2006 | Elmouelhi |
| 2006/0085054 A1 | 4/2006 | Zikorus |
| 2006/0089635 A1 | 4/2006 | Young |
| 2006/0106379 A1 | 5/2006 | O'Brien |
| 2006/0121610 A1 | 6/2006 | Rubinsky |
| 2006/0127703 A1 | 6/2006 | Takekuma |
| 2006/0142801 A1 | 6/2006 | Demarais |
| 2006/0149123 A1 | 7/2006 | Mdlund |
| 2006/0173490 A1 | 8/2006 | Lafontaine |
| 2006/0182684 A1 | 8/2006 | Beliveau |
| 2006/0184163 A1 | 8/2006 | Breen |
| 2006/0195146 A1 | 8/2006 | Tracey |
| 2006/0206150 A1 | 9/2006 | Demarais |
| 2006/0212032 A1 | 9/2006 | Daniel |
| 2006/0212076 A1 | 9/2006 | Demarais |
| 2006/0212078 A1 | 9/2006 | Demarais |
| 2006/0217702 A1 | 9/2006 | Young |
| 2006/0217703 A1 | 9/2006 | Chornenky |
| 2006/0217704 A1 | 9/2006 | Cockburn |
| 2006/0224188 A1 | 10/2006 | Libbus |
| 2006/0224192 A1 | 10/2006 | Dimmer |
| 2006/0234752 A1 | 10/2006 | Mese |
| 2006/0235474 A1 | 10/2006 | Demarais |
| 2006/0241366 A1 | 10/2006 | Falwell |
| 2006/0264752 A1 | 11/2006 | Rubinsky |
| 2006/0264807 A1 | 11/2006 | Westersten |
| 2006/0269531 A1* | 11/2006 | Beebe .................. C12N 13/00 424/155.1 |
| 2006/0271111 A1 | 11/2006 | Demarais |
| 2006/0276710 A1 | 12/2006 | Krishnan |
| 2006/0278241 A1 | 12/2006 | Ruano |
| 2006/0283462 A1 | 12/2006 | Fields |
| 2006/0293713 A1 | 12/2006 | Rubinsky |
| 2006/0293725 A1* | 12/2006 | Rubinsky .............. A61N 1/0412 607/72 |
| 2006/0293730 A1 | 12/2006 | Rubinsky |
| 2006/0293731 A1 | 12/2006 | Rubinsky |
| 2006/0293734 A1 | 12/2006 | Scott |
| 2007/0010805 A1 | 1/2007 | Fedewa |
| 2007/0016125 A1 | 1/2007 | Wong |
| 2007/0016183 A1 | 1/2007 | Lee |
| 2007/0016185 A1 | 1/2007 | Tullis |
| 2007/0021803 A1 | 1/2007 | Deem |
| 2007/0025919 A1 | 2/2007 | Deem |
| 2007/0043345 A1 | 2/2007 | Davalos |
| 2007/0055142 A1 | 3/2007 | Webler |
| 2007/0055225 A1 | 3/2007 | Dodd |
| 2007/0060989 A1 | 3/2007 | Deem |
| 2007/0066957 A1 | 3/2007 | Demarais |
| 2007/0066971 A1 | 3/2007 | Podhajsky |
| 2007/0078391 A1 | 4/2007 | Wortley |
| 2007/0078453 A1 | 4/2007 | Johnson |
| 2007/0083239 A1 | 4/2007 | Demarais |
| 2007/0088347 A1 | 4/2007 | Young |
| 2007/0093789 A1 | 4/2007 | Smith |

(56) References Cited

U.S. PATENT DOCUMENTS

| | | | |
|---|---|---|---|
| 2007/0096048 A1 | 5/2007 | Clerc | |
| 2007/0118069 A1 | 5/2007 | Persson | |
| 2007/0129711 A1 | 6/2007 | Altshuler | |
| 2007/0129720 A1 | 6/2007 | Demarais | |
| 2007/0129760 A1 | 6/2007 | Demarais | |
| 2007/0137567 A1 | 6/2007 | Shimizu | |
| 2007/0151848 A1 | 7/2007 | Novak | |
| 2007/0153135 A1 | 7/2007 | Han | |
| 2007/0156129 A1 | 7/2007 | Kovalcheck | |
| 2007/0156135 A1* | 7/2007 | Rubinsky | A61B 18/1482 606/41 |
| 2007/0156136 A1 | 7/2007 | Godara | |
| 2007/0173899 A1 | 7/2007 | Levin | |
| 2007/0179380 A1 | 8/2007 | Grossman | |
| 2007/0191589 A1 | 8/2007 | Hirota | |
| 2007/0191889 A1 | 8/2007 | Lang | |
| 2007/0197895 A1 | 8/2007 | Nycz | |
| 2007/0203486 A1 | 8/2007 | Young | |
| 2007/0203537 A1 | 8/2007 | Goetz | |
| 2007/0203549 A1 | 8/2007 | Demarais | |
| 2007/0230757 A1 | 10/2007 | Trachtenberg | |
| 2007/0239099 A1 | 10/2007 | Goldfarb | |
| 2007/0244521 A1 | 10/2007 | Bornzin | |
| 2007/0249939 A1 | 10/2007 | Gerbi | |
| 2007/0282407 A1 | 12/2007 | Demarais | |
| 2007/0287950 A1 | 12/2007 | Kjeken | |
| 2007/0295336 A1 | 12/2007 | Nelson | |
| 2007/0295337 A1 | 12/2007 | Nelson | |
| 2008/0015571 A1* | 1/2008 | Rubinsky | A61B 18/1477 606/42 |
| 2008/0015628 A1 | 1/2008 | Dubrul | |
| 2008/0015664 A1 | 1/2008 | Podhajsky | |
| 2008/0021371 A1 | 1/2008 | Rubinsky | |
| 2008/0027314 A1 | 1/2008 | Miyazaki | |
| 2008/0027343 A1 | 1/2008 | Fields | |
| 2008/0033340 A1 | 2/2008 | Heller | |
| 2008/0033417 A1 | 2/2008 | Nields | |
| 2008/0045880 A1 | 2/2008 | Rune | |
| 2008/0052786 A1 | 2/2008 | Lin | |
| 2008/0065062 A1 | 3/2008 | Leung | |
| 2008/0071262 A1 | 3/2008 | Azure | |
| 2008/0071264 A1 | 3/2008 | Azure | |
| 2008/0071265 A1 | 3/2008 | Azure | |
| 2008/0082145 A1 | 4/2008 | Skwarek | |
| 2008/0086115 A1 | 4/2008 | Stoklund | |
| 2008/0091135 A1 | 4/2008 | Draghia-Akli | |
| 2008/0097139 A1* | 4/2008 | Clerc | A61B 18/0218 600/7 |
| 2008/0097422 A1 | 4/2008 | Edwards | |
| 2008/0103529 A1 | 5/2008 | Schoenbach | |
| 2008/0121375 A1 | 5/2008 | Richason | |
| 2008/0125772 A1 | 5/2008 | Stone | |
| 2008/0125775 A1 | 5/2008 | Morris | |
| 2008/0132826 A1* | 6/2008 | Shadduck | A61B 18/04 604/114 |
| 2008/0132884 A1 | 6/2008 | Rubinsky | |
| 2008/0132885 A1 | 6/2008 | Rubinsky | |
| 2008/0140064 A1 | 6/2008 | Vegesna | |
| 2008/0146931 A1 | 6/2008 | Zhang | |
| 2008/0146934 A1 | 6/2008 | Czygan | |
| 2008/0147056 A1 | 6/2008 | Van Der Weide | |
| 2008/0154259 A1 | 6/2008 | Gough | |
| 2008/0167649 A1 | 7/2008 | Edwards | |
| 2008/0171985 A1 | 7/2008 | Karakoca | |
| 2008/0172104 A1* | 7/2008 | Kieval | A61N 1/0556 607/46 |
| 2008/0183256 A1 | 7/2008 | Keacher | |
| 2008/0190434 A1 | 8/2008 | Tjong Joe Wai | |
| 2008/0200911 A1* | 8/2008 | Long | A61B 18/1477 606/34 |
| 2008/0200912 A1 | 8/2008 | Long | |
| 2008/0208052 A1 | 8/2008 | LePivert | |
| 2008/0210243 A1 | 9/2008 | Clayton | |
| 2008/0213331 A1 | 9/2008 | Gelfand | |
| 2008/0214986 A1 | 9/2008 | Ivorra | |
| 2008/0224188 A1 | 9/2008 | Han | |
| 2008/0234708 A1 | 9/2008 | Houser | |
| 2008/0236593 A1 | 10/2008 | Nelson | |
| 2008/0249503 A1 | 10/2008 | Fields | |
| 2008/0255553 A1 | 10/2008 | Young | |
| 2008/0262489 A1 | 10/2008 | Steinke | |
| 2008/0269586 A1 | 10/2008 | Rubinsky | |
| 2008/0269838 A1 | 10/2008 | Brighton | |
| 2008/0275465 A1 | 11/2008 | Paul | |
| 2008/0279995 A1 | 11/2008 | Schultheiss | |
| 2008/0281319 A1 | 11/2008 | Paul | |
| 2008/0283065 A1 | 11/2008 | Chang | |
| 2008/0288038 A1 | 11/2008 | Paul | |
| 2008/0294155 A1 | 11/2008 | Cronin | |
| 2008/0294358 A1 | 11/2008 | Richardson | |
| 2008/0300589 A1 | 12/2008 | Paul | |
| 2008/0306427 A1 | 12/2008 | Bailey | |
| 2008/0312599 A1 | 12/2008 | Rosenberg | |
| 2008/0319511 A1 | 12/2008 | Pless | |
| 2009/0018206 A1 | 1/2009 | Barkan | |
| 2009/0018565 A1 | 1/2009 | To | |
| 2009/0018566 A1 | 1/2009 | Escudero | |
| 2009/0018567 A1 | 1/2009 | Escudero | |
| 2009/0024075 A1 | 1/2009 | Schroeppel | |
| 2009/0024085 A1 | 1/2009 | To | |
| 2009/0029407 A1 | 1/2009 | Gazit | |
| 2009/0030336 A1 | 1/2009 | Woo | |
| 2009/0036773 A1 | 2/2009 | Lau | |
| 2009/0038752 A1 | 2/2009 | Weng | |
| 2009/0062788 A1* | 3/2009 | Long | A61B 18/14 606/41 |
| 2009/0062792 A1 | 3/2009 | Vakharia | |
| 2009/0062795 A1 | 3/2009 | Vakharia | |
| 2009/0076496 A1 | 3/2009 | Azure | |
| 2009/0076499 A1 | 3/2009 | Azure | |
| 2009/0076500 A1 | 3/2009 | Azure | |
| 2009/0076502 A1 | 3/2009 | Azure | |
| 2009/0081272 A1 | 3/2009 | Clarke | |
| 2009/0088636 A1 | 4/2009 | Lau | |
| 2009/0099544 A1 | 4/2009 | Munrow | |
| 2009/0105703 A1 | 4/2009 | Shadduck | |
| 2009/0114226 A1 | 5/2009 | Deem | |
| 2009/0118725 A1 | 5/2009 | Auth | |
| 2009/0118729 A1 | 5/2009 | Auth | |
| 2009/0125009 A1 | 5/2009 | Zikorus | |
| 2009/0138014 A1 | 5/2009 | Bonutti | |
| 2009/0157166 A1 | 6/2009 | Singhal | |
| 2009/0163904 A1 | 6/2009 | Miller | |
| 2009/0171280 A1 | 7/2009 | Samuel | |
| 2009/0177111 A1 | 7/2009 | Miller | |
| 2009/0186850 A1 | 7/2009 | Kiribayashi | |
| 2009/0198227 A1 | 8/2009 | Prakash | |
| 2009/0198231 A1 | 8/2009 | Esser | |
| 2009/0204005 A1 | 8/2009 | Keast | |
| 2009/0204112 A1 | 8/2009 | Kleyman | |
| 2009/0209955 A1 | 8/2009 | Forster | |
| 2009/0216543 A1 | 8/2009 | Pang | |
| 2009/0221939 A1 | 9/2009 | Demarais | |
| 2009/0228001 A1 | 9/2009 | Pacey | |
| 2009/0240247 A1 | 9/2009 | Rioux | |
| 2009/0247933 A1 | 10/2009 | Maor | |
| 2009/0248012 A1* | 10/2009 | Maor | A61B 18/14 606/41 |
| 2009/0269317 A1 | 10/2009 | Davalos | |
| 2009/0270756 A1 | 10/2009 | Gamache | |
| 2009/0275827 A1 | 11/2009 | Aiken | |
| 2009/0281477 A1 | 11/2009 | Mikus | |
| 2009/0281540 A1 | 11/2009 | Blomgren | |
| 2009/0287081 A1 | 11/2009 | Grossman | |
| 2009/0292342 A1 | 11/2009 | Rubinsky | |
| 2009/0301480 A1 | 12/2009 | Elsakka | |
| 2009/0306544 A1 | 12/2009 | Ng | |
| 2009/0306545 A1 | 12/2009 | Elsakka | |
| 2009/0318849 A1 | 12/2009 | Hobbs | |
| 2009/0318905 A1 | 12/2009 | Bhargav | |
| 2009/0326346 A1 | 12/2009 | Kracker | |
| 2009/0326366 A1 | 12/2009 | Krieg | |
| 2009/0326436 A1 | 12/2009 | Rubinsky | |

(56) References Cited

U.S. PATENT DOCUMENTS

| | | |
|---|---|---|
| 2009/0326561 A1 | 12/2009 | Carroll, II |
| 2009/0326570 A1 | 12/2009 | Brown |
| 2010/0004623 A1 | 1/2010 | Hamilton, Jr. |
| 2010/0006441 A1 | 1/2010 | Renaud |
| 2010/0016783 A1 | 1/2010 | Bourke, Jr. |
| 2010/0023004 A1 | 1/2010 | Francischelli |
| 2010/0030211 A1 | 2/2010 | Davalos |
| 2010/0036291 A1 | 2/2010 | Darlington |
| 2010/0049190 A1* | 2/2010 | Long .............. A61B 18/1492 606/41 |
| 2010/0056926 A1 | 3/2010 | Deckman |
| 2010/0057074 A1 | 3/2010 | Roman |
| 2010/0057076 A1 | 3/2010 | Behnke |
| 2010/0069921 A1 | 3/2010 | Miller |
| 2010/0079215 A1 | 4/2010 | Brannan |
| 2010/0082022 A1 | 4/2010 | Haley |
| 2010/0082023 A1 | 4/2010 | Brannan |
| 2010/0082024 A1 | 4/2010 | Brannan |
| 2010/0082025 A1 | 4/2010 | Brannan |
| 2010/0082083 A1 | 4/2010 | Brannan |
| 2010/0082084 A1 | 4/2010 | Brannan |
| 2010/0087813 A1 | 4/2010 | Long |
| 2010/0090696 A1 | 4/2010 | Deimling |
| 2010/0100093 A1 | 4/2010 | Azure |
| 2010/0106025 A1 | 4/2010 | Sarfaty |
| 2010/0106047 A1 | 4/2010 | Sarfaty |
| 2010/0121173 A1 | 5/2010 | Sarfaty |
| 2010/0130975 A1 | 5/2010 | Long |
| 2010/0147701 A1 | 6/2010 | Field |
| 2010/0152725 A1 | 6/2010 | Pearson |
| 2010/0160850 A1 | 6/2010 | Ivorra |
| 2010/0160906 A1 | 6/2010 | Jarrard |
| 2010/0168735 A1 | 7/2010 | Deno |
| 2010/0174282 A1 | 7/2010 | Demarais |
| 2010/0179436 A1 | 7/2010 | Sarfaty |
| 2010/0179530 A1* | 7/2010 | Long .............. A61B 18/1492 606/41 |
| 2010/0191112 A1 | 7/2010 | Demarais |
| 2010/0191235 A1 | 7/2010 | Moshe |
| 2010/0196984 A1 | 8/2010 | Rubinsky |
| 2010/0204560 A1 | 8/2010 | Salahieh |
| 2010/0204638 A1 | 8/2010 | Hobbs |
| 2010/0211061 A1 | 8/2010 | Leyh |
| 2010/0222377 A1 | 9/2010 | Crooks |
| 2010/0222677 A1 | 9/2010 | Placek |
| 2010/0228234 A1 | 9/2010 | Hyde |
| 2010/0228247 A1 | 9/2010 | Paul |
| 2010/0241117 A1 | 9/2010 | Paul |
| 2010/0249771 A1 | 9/2010 | Pearson |
| 2010/0250209 A1 | 9/2010 | Pearson |
| 2010/0255795 A1 | 10/2010 | Rubinsky |
| 2010/0256624 A1 | 10/2010 | Brannan |
| 2010/0256628 A1 | 10/2010 | Pearson |
| 2010/0256630 A1 | 10/2010 | Hamilton, Jr. |
| 2010/0261994 A1 | 10/2010 | Davalos |
| 2010/0262067 A1 | 10/2010 | Chornenky |
| 2010/0268223 A1 | 10/2010 | Coe |
| 2010/0268225 A1 | 10/2010 | Coe |
| 2010/0286690 A1 | 11/2010 | Paul |
| 2010/0292686 A1 | 11/2010 | Rick |
| 2010/0298822 A1 | 11/2010 | Behnke |
| 2010/0298823 A1 | 11/2010 | Cao |
| 2010/0298825 A1 | 11/2010 | Slizynski |
| 2010/0331758 A1 | 12/2010 | Davalos |
| 2010/0331911 A1 | 12/2010 | Kovalcheck |
| 2011/0009860 A1 | 1/2011 | Chornenky |
| 2011/0015630 A1 | 1/2011 | Azure |
| 2011/0017207 A1 | 1/2011 | Hendricksen |
| 2011/0021970 A1 | 1/2011 | Vo-Dinh |
| 2011/0034209 A1 | 2/2011 | Rubinsky |
| 2011/0054458 A1 | 3/2011 | Behnke |
| 2011/0064371 A1 | 3/2011 | Leatherman |
| 2011/0064671 A1 | 3/2011 | Bynoe |
| 2011/0082362 A1 | 4/2011 | Schmidt |
| 2011/0082414 A1 | 4/2011 | Wallace |
| 2011/0092973 A1 | 4/2011 | Nuccitelli |
| 2011/0098695 A1 | 4/2011 | Brannan |
| 2011/0105823 A1 | 5/2011 | Single, Jr. |
| 2011/0106221 A1 | 5/2011 | Neal, II |
| 2011/0112434 A1 | 5/2011 | Ghabrial |
| 2011/0112531 A1 | 5/2011 | Landis |
| 2011/0118721 A1 | 5/2011 | Brannan |
| 2011/0118727 A1 | 5/2011 | Fish |
| 2011/0118729 A1 | 5/2011 | Heeren |
| 2011/0118732 A1 | 5/2011 | Rubinsky |
| 2011/0118734 A1 | 5/2011 | Auld |
| 2011/0130834 A1 | 6/2011 | Wilson |
| 2011/0135626 A1 | 6/2011 | Kovalcheck |
| 2011/0144524 A1 | 6/2011 | Fish |
| 2011/0144562 A1 | 6/2011 | Heeren |
| 2011/0144635 A1 | 6/2011 | Harper |
| 2011/0144638 A1 | 6/2011 | Heeren |
| 2011/0144641 A1 | 6/2011 | Dimalanta, Jr. |
| 2011/0144657 A1 | 6/2011 | Fish |
| 2011/0152678 A1 | 6/2011 | Aljuri |
| 2011/0152906 A1 | 6/2011 | Escudero |
| 2011/0152907 A1 | 6/2011 | Escudero |
| 2011/0160514 A1 | 6/2011 | Long |
| 2011/0166499 A1 | 7/2011 | Demarais |
| 2011/0172659 A1 | 7/2011 | Brannan |
| 2011/0176037 A1 | 7/2011 | Benkley, III |
| 2011/0178570 A1 | 7/2011 | Demarais |
| 2011/0190851 A1 | 8/2011 | Kelly |
| 2011/0202052 A1 | 8/2011 | Gelbart |
| 2011/0202053 A1 | 8/2011 | Moss |
| 2011/0207758 A1 | 8/2011 | Sobotka |
| 2011/0208096 A1 | 8/2011 | Demarais |
| 2011/0208180 A1 | 8/2011 | Brannan |
| 2011/0217730 A1 | 9/2011 | Gazit |
| 2011/0230874 A1 | 9/2011 | Epstein |
| 2011/0238057 A1 | 9/2011 | Moss |
| 2011/0245756 A1 | 10/2011 | Arora |
| 2011/0251607 A1 | 10/2011 | Kruecker |
| 2011/0282354 A1 | 11/2011 | Schulte |
| 2011/0288545 A1 | 11/2011 | Beebe |
| 2011/0301587 A1 | 12/2011 | Deem |
| 2011/0306971 A1 | 12/2011 | Long |
| 2012/0034131 A1 | 2/2012 | Rubinsky |
| 2012/0046658 A1 | 2/2012 | Kreindel |
| 2012/0059255 A1 | 3/2012 | Paul |
| 2012/0071870 A1 | 3/2012 | Salahieh |
| 2012/0071872 A1 | 3/2012 | Rubinsky |
| 2012/0071874 A1 | 3/2012 | Davalos |
| 2012/0085649 A1 | 4/2012 | Sano |
| 2012/0089009 A1 | 4/2012 | Omary |
| 2012/0090643 A1 | 4/2012 | Bertsch |
| 2012/0090646 A1 | 4/2012 | Tanaka |
| 2012/0095459 A1 | 4/2012 | Callas |
| 2012/0101538 A1 | 4/2012 | Ballakur |
| 2012/0109122 A1 | 5/2012 | Arena |
| 2012/0130289 A1 | 5/2012 | Demarais |
| 2012/0150172 A1 | 6/2012 | Ortiz |
| 2012/0165813 A1 | 6/2012 | Lee |
| 2012/0179091 A1 | 7/2012 | Ivorra |
| 2012/0220998 A1* | 8/2012 | Long .............. A61B 18/1206 606/41 |
| 2012/0220999 A1 | 8/2012 | Long |
| 2012/0226218 A1 | 9/2012 | Phillips |
| 2012/0226271 A1 | 9/2012 | Callas |
| 2012/0265183 A1 | 10/2012 | Tulleken |
| 2012/0265186 A1 | 10/2012 | Burger |
| 2012/0277741 A1 | 11/2012 | Davalos |
| 2012/0303012 A1 | 11/2012 | Leyh |
| 2012/0303020 A1 | 11/2012 | Chornenky |
| 2012/0310236 A1 | 12/2012 | Placek |
| 2012/0310237 A1 | 12/2012 | Swanson |
| 2013/0023871 A1 | 1/2013 | Collins |
| 2013/0030239 A1 | 1/2013 | Weyh |
| 2013/0030430 A1 | 1/2013 | Stewart |
| 2013/0033977 A1 | 2/2013 | Lin |
| 2013/0035921 A1 | 2/2013 | Rodriguez-Ponce |
| 2013/0041436 A1 | 2/2013 | Ruse |
| 2013/0072858 A1 | 3/2013 | Watson |
| 2013/0090346 A1 | 4/2013 | Johns |

(56) References Cited

U.S. PATENT DOCUMENTS

| | | |
|---|---|---|
| 2013/0090646 A1 | 4/2013 | Moss |
| 2013/0108667 A1 | 5/2013 | Soikum |
| 2013/0110103 A1 | 5/2013 | Assmus |
| 2013/0110106 A1 | 5/2013 | Richardson |
| 2013/0184702 A1 | 7/2013 | Neal, II |
| 2013/0196441 A1 | 8/2013 | Rubinsky |
| 2013/0197425 A1 | 8/2013 | Golberg |
| 2013/0202766 A1 | 8/2013 | Rubinsky |
| 2013/0218157 A1 | 8/2013 | Callas |
| 2013/0230895 A1 | 9/2013 | Koblizek |
| 2013/0238062 A1 | 9/2013 | Ron Edoute |
| 2013/0253415 A1 | 9/2013 | Sano |
| 2013/0261389 A1 | 10/2013 | Long |
| 2013/0281968 A1 | 10/2013 | Davalos |
| 2013/0296679 A1 | 11/2013 | Condie |
| 2013/0338761 A1 | 12/2013 | Plowiecki |
| 2013/0345697 A1 | 12/2013 | Garcia |
| 2013/0345779 A1 | 12/2013 | Maor |
| 2014/0005664 A1 | 1/2014 | Govari |
| 2014/0017218 A1 | 1/2014 | Scott |
| 2014/0039489 A1 | 2/2014 | Davalos |
| 2014/0046322 A1 | 2/2014 | Callas |
| 2014/0052118 A1 | 2/2014 | Laske |
| 2014/0066913 A1 | 3/2014 | Sherman |
| 2014/0081255 A1 | 3/2014 | Johnson |
| 2014/0088578 A1 | 3/2014 | Rubinsky |
| 2014/0094792 A1 | 4/2014 | Sharonov |
| 2014/0094793 A1 | 4/2014 | Sharonov |
| 2014/0107643 A1 | 4/2014 | Chornenky |
| 2014/0111224 A1 | 4/2014 | Agate |
| 2014/0121663 A1 | 5/2014 | Pearson |
| 2014/0121728 A1 | 5/2014 | Dhillon |
| 2014/0163551 A1 | 6/2014 | Maor |
| 2014/0207133 A1 | 7/2014 | Model |
| 2014/0276748 A1 | 9/2014 | Ku |
| 2014/0296844 A1 | 10/2014 | Kevin |
| 2014/0309579 A1 | 10/2014 | Rubinsky |
| 2014/0378964 A1 | 12/2014 | Pearson |
| 2015/0025526 A1 | 1/2015 | Hua |
| 2015/0032105 A1 | 1/2015 | Azure |
| 2015/0066013 A1 | 3/2015 | Salahieh |
| 2015/0066020 A1 | 3/2015 | Epstein |
| 2015/0088120 A1 | 3/2015 | Garcia |
| 2015/0088220 A1 | 3/2015 | Callas |
| 2015/0112333 A1 | 4/2015 | Chorenky |
| 2015/0126922 A1 | 5/2015 | Willis |
| 2015/0134584 A1 | 5/2015 | Nakagawa |
| 2015/0141984 A1 | 5/2015 | Loomas |
| 2015/0152504 A1 | 6/2015 | Lin |
| 2015/0164584 A1 | 6/2015 | Davalos |
| 2015/0173824 A1 | 6/2015 | Davalos |
| 2015/0196351 A1 | 7/2015 | Stone |
| 2015/0201996 A1 | 7/2015 | Rubinsky |
| 2015/0265349 A1 | 9/2015 | Moss |
| 2015/0289923 A1 | 10/2015 | Davalos |
| 2015/0320478 A1 | 11/2015 | Cosman, Jr. |
| 2015/0320481 A1 | 11/2015 | Cosman, Jr. |
| 2015/0320488 A1 | 11/2015 | Moshe |
| 2015/0320999 A1 | 11/2015 | Nuccitelli |
| 2015/0327944 A1 | 11/2015 | Neal, II |
| 2016/0022957 A1 | 1/2016 | Hobbs |
| 2016/0066977 A1 | 3/2016 | Neal, II |
| 2016/0074114 A1 | 3/2016 | Pearson |
| 2016/0113708 A1 | 4/2016 | Moss |
| 2016/0143398 A1 | 5/2016 | Kim |
| 2016/0143698 A1 | 5/2016 | Garcia |
| 2016/0235470 A1 | 8/2016 | Callas |
| 2016/0287313 A1 | 10/2016 | Rubinsky |
| 2016/0287314 A1 | 10/2016 | Arena |
| 2016/0337310 A1 | 11/2016 | Faccin |
| 2016/0338758 A9 | 11/2016 | Davalos |
| 2016/0338761 A1 | 11/2016 | Chornenky |
| 2016/0354142 A1 | 12/2016 | Pearson |
| 2016/0367310 A1 | 12/2016 | Onik |
| 2017/0035501 A1 | 2/2017 | Chornenky |
| 2017/0065339 A1 | 3/2017 | Mickelsen |
| 2017/0137512 A1 | 5/2017 | Van Hoorick |
| 2017/0189579 A1 | 7/2017 | Davalos |
| 2017/0209620 A1 | 7/2017 | Davalos |
| 2017/0266438 A1 | 9/2017 | Sano |
| 2017/0319851 A1 | 11/2017 | Athos |
| 2017/0348525 A1 | 12/2017 | Sano |
| 2017/0360323 A1 | 12/2017 | Li |
| 2017/0360326 A1 | 12/2017 | Davalos |
| 2018/0036529 A1 | 2/2018 | Jaroszeski |
| 2018/0071014 A1 | 3/2018 | Neal |
| 2018/0125565 A1 | 5/2018 | Sano |
| 2018/0132922 A1 | 5/2018 | Neal, II |
| 2018/0161086 A1 | 6/2018 | Davalos |
| 2018/0198218 A1 | 7/2018 | Regan |
| 2019/0023804 A1 | 1/2019 | Onik |
| 2019/0029749 A1 | 1/2019 | Garcia |
| 2019/0046255 A1 | 2/2019 | Davalos |
| 2019/0069945 A1 | 3/2019 | Davalos |
| 2019/0076528 A1 | 3/2019 | Soden |
| 2019/0083169 A1 | 3/2019 | Single |
| 2019/0133671 A1 | 5/2019 | Davalos |
| 2019/0175248 A1 | 6/2019 | Neal, II |
| 2019/0175260 A1 | 6/2019 | Davalos |
| 2019/0223938 A1 | 7/2019 | Arena |
| 2019/0232048 A1 | 8/2019 | Latouche |
| 2019/0233809 A1 | 8/2019 | Neal, II |
| 2019/0256839 A1 | 8/2019 | Neal, II |
| 2019/0282294 A1 | 9/2019 | Davalos |
| 2019/0328445 A1 | 10/2019 | Sano |
| 2019/0351224 A1 | 11/2019 | Sano |
| 2019/0376055 A1 | 12/2019 | Davalos |
| 2020/0046432 A1 | 2/2020 | Garcia |
| 2020/0046967 A1 | 2/2020 | Ivey |
| 2020/0093541 A9 | 3/2020 | Neal et al. |
| 2020/0197073 A1 | 6/2020 | Sano |
| 2020/0260987 A1 | 8/2020 | Davalos |
| 2020/0289188 A1 | 9/2020 | Forsyth |
| 2020/0323576 A1 | 10/2020 | Neal |
| 2020/0405373 A1 | 12/2020 | O'Brien |
| 2021/0022795 A1 | 1/2021 | Davalos |
| 2021/0023362 A1 | 1/2021 | Lorenzo |
| 2021/0052882 A1 | 2/2021 | Wasson |
| 2021/0113265 A1 | 4/2021 | D'Agostino |
| 2021/0137410 A1 | 5/2021 | O'Brien |
| 2021/0186600 A1 | 6/2021 | Davalos |
| 2021/0361341 A1 | 11/2021 | Neal, II |
| 2021/0393312 A1 | 12/2021 | Davalos |
| 2022/0151688 A1 | 5/2022 | Garcia |
| 2022/0161027 A1 | 5/2022 | Aycock |
| 2022/0290183 A1 | 9/2022 | Davalos |
| 2022/0362549 A1 | 11/2022 | Sano |
| 2023/0157759 A1 | 5/2023 | Garcia |
| 2023/0212551 A1 | 7/2023 | Neal, II |
| 2023/0248414 A1 | 8/2023 | Sano |
| 2023/0355293 A1 | 11/2023 | Rafael, V |
| 2023/0355968 A1 | 11/2023 | Davalos |
| 2024/0008911 A1 | 1/2024 | Davalos |
| 2024/0074804 A1 | 3/2024 | Neal |
| 2024/0173063 A1 | 5/2024 | Neal, II |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2012255070 | 1/2014 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |

(56) References Cited

FOREIGN PATENT DOCUMENTS

| | | |
|---|---|---|
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 833111 | 3/1952 |
| DE | 863111 | 1/1953 |
| DE | 4000893 A1 | 7/1991 |
| DE | 60038026 T2 | 2/2009 |
| EP | 0218275 A1 | 4/1987 |
| EP | 0339501 A2 | 11/1989 |
| EP | 0378132 A2 | 7/1990 |
| EP | 0528891 A1 | 3/1993 |
| EP | 0533511 A1 | 3/1993 |
| EP | 0908156 | 4/1999 |
| EP | 0935482 A1 | 8/1999 |
| EP | 0998235 A1 | 5/2000 |
| EP | 1011495 A1 | 6/2000 |
| EP | 0528891 B1 | 7/2000 |
| EP | 1061983 A1 | 12/2000 |
| EP | 1196550 A2 | 4/2002 |
| EP | 1207797 A1 | 5/2002 |
| EP | 1344497 | 9/2003 |
| EP | 1406685 A1 | 4/2004 |
| EP | 1424970 A2 | 6/2004 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1791485 B1 | 6/2007 |
| EP | 1796568 A1 | 6/2007 |
| EP | 1207797 B1 | 2/2008 |
| EP | 1406685 B1 | 6/2008 |
| EP | 1962708 B1 | 9/2008 |
| EP | 1962710 B1 | 9/2008 |
| EP | 1962945 B1 | 9/2008 |
| EP | 1424970 B1 | 12/2008 |
| EP | 2280741 A1 | 2/2011 |
| EP | 2373241 B1 | 10/2011 |
| EP | 2381829 A1 | 11/2011 |
| EP | 2413833 A1 | 2/2012 |
| EP | 2429435 | 3/2012 |
| EP | 2488251 A2 | 8/2012 |
| EP | 2593179 | 5/2013 |
| EP | 2627274 | 8/2013 |
| EP | 2642937 A2 | 10/2013 |
| EP | 2651505 | 10/2013 |
| EP | 3143124 A1 | 3/2017 |
| EP | 3852868 A1 | 7/2021 |
| ES | 2300272 T3 | 6/2008 |
| ES | 2315493 | 4/2009 |
| JP | H10243947 A | 9/1998 |
| JP | 2001510702 A | 8/2001 |
| JP | 2002360712 A | 12/2002 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2007516792 | 6/2007 |
| JP | 2008508946 A | 3/2008 |
| JP | 4252316 A | 4/2009 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2010511467 A | 4/2010 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 4/2004 |
| WO | 9104014 A1 | 4/1991 |
| WO | 9614238 | 5/1996 |
| WO | 9634571 A1 | 11/1996 |
| WO | 9639531 A1 | 12/1996 |
| WO | 9810745 A1 | 3/1998 |
| WO | 9814238 A1 | 4/1998 |
| WO | 9904710 A1 | 2/1999 |
| WO | 0020554 A1 | 4/2000 |
| WO | 0107583 A1 | 2/2001 |
| WO | 0107584 A1 | 2/2001 |
| WO | 0107585 A1 | 2/2001 |
| WO | 0110319 A1 | 2/2001 |
| WO | 2001048153 A1 | 7/2001 |
| WO | 0181533 A1 | 11/2001 |
| WO | 0200554 A1 | 1/2002 |
| WO | 02078527 A2 | 10/2002 |
| WO | 02089686 A1 | 11/2002 |
| WO | 02100459 A2 | 12/2002 |
| WO | 2003020144 A1 | 3/2003 |
| WO | 2003047684 A2 | 6/2003 |
| WO | 03099382 A1 | 12/2003 |
| WO | 2004008153 | 1/2004 |
| WO | 2004037341 A2 | 5/2004 |
| WO | 2004080347 A2 | 9/2004 |
| WO | 2005065284 A2 | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2007137303 A2 | 11/2007 |
| WO | 2008034103 A3 | 3/2008 |
| WO | 2008063195 A1 | 5/2008 |
| WO | 2008101086 A2 | 8/2008 |
| WO | 2008101091 A2 | 8/2008 |
| WO | 2009036468 A1 | 3/2009 |
| WO | 2009046176 A1 | 4/2009 |
| WO | 2009134876 A1 | 11/2009 |
| WO | 2009135070 A1 | 11/2009 |
| WO | 2009137800 A2 | 11/2009 |
| WO | 2010015592 | 2/2010 |
| WO | 2010064154 A1 | 6/2010 |
| WO | 2010080974 A1 | 7/2010 |
| WO | 2010085765 | 7/2010 |
| WO | 2010117806 A1 | 10/2010 |
| WO | 2010118387 A | 10/2010 |
| WO | 2010128373 | 11/2010 |
| WO | 2010132472 A1 | 11/2010 |
| WO | 2010151277 A1 | 12/2010 |
| WO | 2011028937 | 3/2011 |
| WO | 2011047387 A2 | 4/2011 |
| WO | 2011062653 A1 | 5/2011 |
| WO | 2011072221 A1 | 6/2011 |
| WO | 2011135294 A1 | 11/2011 |
| WO | 2012006533 A1 | 1/2012 |
| WO | 2012051433 A2 | 4/2012 |
| WO | 2012054560 A1 | 4/2012 |

(56) References Cited

FOREIGN PATENT DOCUMENTS

| WO | 2012054573 A2 | 4/2012 |
|---|---|---|
| WO | 2012063266 | 5/2012 |
| WO | 2012071526 A2 | 5/2012 |
| WO | 2012088149 A2 | 6/2012 |
| WO | 2012140376 | 10/2012 |
| WO | 2013052138 | 4/2013 |
| WO | 2013176881 | 11/2013 |
| WO | 2014039320 | 3/2014 |
| WO | 2015175570 A1 | 11/2015 |
| WO | 2015192027 A1 | 12/2015 |
| WO | 2016100325 A1 | 6/2016 |
| WO | 2016164930 A1 | 10/2016 |
| WO | 2017024123 A1 | 2/2017 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |
| WO | 2024081749 A2 | 4/2024 |

OTHER PUBLICATIONS

Gowrishankar T.R., et al., "Microdosimetry for conventional and supra-electroporation in cells with organelles". Biochem Biophys Res Commun, 341(4): p. 1266-76 (2006).
Granot, Y., A. Ivorra, E. Maor, and B. Rubinsky, "In vivo imaging of irreversible electroporation by means of electrical impedance tomography," Physics in Medicine & Biology, vol. 54, No. 16, pp. 4927, 2009.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue spectroscopy with electrical impedance tomography: Computer simulations, IEEE Transactions on Biomedical Engineering, Sep. 1995, vol. 42, No. 9, pp. 948-954.
Groen, M. H. A et al., "In Vivo Analysis of the Origin and Characteristics of Gaseous Microemboli during Catheter- Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Gumerov, et al., The Dipole Approximation Method and Its Coupling with the Regular Boundary Element Method for Efficient Electrical Impedance Tomography, Boundary Element Technology XIII, 1999, 10 pp.
Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.
Hall, et al, Nanosecond pulsed electric fields have differential effects on cells in the S-phase, DNA and Cell Biology, 2007, vol. 26, No. 3, pp. 160-171.
Hall, et al, Nanosecond pulsed electric fields induce apoptosis in p53-wildtype and p53-null HCT116 colon carcinoma cells, Apoptosis, May 23, 2007, 12, pp. 1721-1731.
Hapala, Breaking the Barrier: Methods for Reversible Permeabilization of Cellular Membranes, Critical Reviews in Biotechnology, 17(2): 105-122, 1997.
Hasgall, P. et al., "IT'IS Database for thermal and electromagnetic parameters of biological tissues," 2018, it is.swiss/ database%0A%0A, 4 pages.
He, et al, Nonlinear current response of micro electroporation and resealing dynamics for human cancer cells, Bioelectrochemistry, Jan. 29, 2008, 72, pp. 161-168.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, et al., MRI study on reversible and irreversible electroporation induced blood brain barrier disruption, Aug. 10, 2012, PLOS One, vol. 7, 8, e42817, pp. 1-9.
Hjouj, M. et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, page iii 114.
Hjouj, M., et al., "MRI Study on Reversible and Irreversible Electroporation Induced Blood Brain Barrier Disruption", PLOS ONE, Aug. 2012, 7:8, e42817.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Hong, et al, Cardiac ablation via electroporation, 31st Annual International Conference of the IEEE EMBS, IEEE, Sep. 2, 2009, pp. 3381-3384.
Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
International Search Report 12002108.4 ESO dated Jun. 12, 2013.
International Search Report for 06751655 SESR dated Oct. 9, 2016. 3 pages.
International Search Report for 06751655.9 ESO dated Oct. 29, 2009.
International Search Report for 10824248.8 ESO dated Jan. 20, 2014. 3 pages.
International Search Report for 11833421 SESR dated Mar. 18, 2014. 2 pages.
International Search Report for Iprp, PCT/US2006/01645, dated Oct. 30, 2007, 5 pages.
International Search Report for PCT-US-10-053077 Isr dated Aug. 2, 2011.
International Search Report for PCT-US-10-053077 WOSA dated Aug. 2, 2011.
International Search Report for PCT/US06/16045 ISR dated Sep. 25, 2007, 1 page.
International Search Report for PCT/US2006/016045 IPRP dated Oct. 30, 2007.
International Search Report for PCT/US2007/000084 IPRP dated Jul. 8, 2008, 8 pages.
International Search Report for PCT/US2009/038661 IPRP dated Sep. 28, 2010.
International Search Report for PCT/US2009/042100 IPRP dated Nov. 2, 2010.
International Search Report for PCT/US2009/042100 WOSA dated Jul. 9, 2009.
International Search Report for PCT/US2009/047969 IPRP dated Dec. 21, 2010.
International Search Report for PCT/US2009/047969 ISR dated Jan. 21, 2010.
International Search Report for PCT/US2009/047969 WOSA dated Jan. 21, 2010.
International Search Report for PCT/US2009/048270 IPRP dated Jan. 5, 2011.

(56) References Cited

OTHER PUBLICATIONS

International Search Report for PCT/US2009/048270 ISR dated Feb. 11, 2010.
International Search Report for PCT/US2009/048270 WOSA dated Feb. 11, 2010.
International Search Report for PCT/US2009/062806 WOSA dated Jan. 19, 2010.
International Search Report for PCT/US2010/022011 IPRP dated Jul. 26, 2011.
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journa of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Thomson, Human experience with irreversible electroporation, Irreversible Electroporation, BIOMED, 2010, pp. 249-354.
Tibbitt et al., "Hydrogels as Extracellular Matrix Mimics for 3D Cell Culture", Jul. 2009, Biotechnol Bioeng, 103 (4),655-663.
Tijink, et al, How we do it: Chemo-electroporation in the head and neck for otherwise untreatable patients, Correspondence, Clinical Otolaryngology, 2006, 31, pp. 447-451.
Tracy, et al, Irreversible electroporation (Ire): A novel method for renal tissue ablation, BJU International, 107, pp. 1982-1987.
Trimmer, et al, Minimally invasive percutaneous treatment of small renal tumors with irreversible electroporation: a single-center experience, J Vasc Intery Radiol, 2015, 26: pp. 1465-1471.
Troszak, et al., Self-powered electroporation using a singularity-induced nano-electroporation configuration, Biochemical and Biophysical Research Communications, Sep. 28, 2011, 414, pp. 419-424.
Tsivian, Polascik, Recent advances in focal therapy of prostate and kidney cancer, Medicine Reports, Jan. 18, 2010, 2, 1, pp. 1-3.
Valdez, C. M. et al., "The interphase interval within a bipolar nanosecond electric pulse modulates bipolar cancellation," Bioelectromagnetics, vol. 39, No. 6, 441-450, 2018, 28 pages.
Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.
Verbridge et al., "Oxygen-Controlled Three-Dimensional Cultures to Analyze Tumor Angiogenesis." Tissue Engineering, Part A vol. 16, pp. 2133-2141 (2010).
Verma, A. et al., "Primer on Pulsed Electrical Field Ablation: Understanding the Benefits and Limitations," Circ. Arrhythmia Electrophysiol., No. September, pp. 1-16, 2021, 16 pages.
Vernier, P.T., et al., "Nanoelectropulse-driven membrane perturbation and small molecule permeabilization", Bmc Cell Biology, 7 (2006). 16 pages.
Vidamed, Inc., "Highlights from Worldwide Clinical Studies: Transurethral Needle Ablation (TUNA)," Vidamed's Office TUNA System, (4 pages) (2001).
Vizintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Voyer, D., A. Silve, L. M. Mir, R. Scorretti, and C. Poignard, "Dynamical modeling of tissue electroporation," Bioelectrochemistry, vol. 119, pp. 98-110, 2018.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEETrns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011) 2 pages.
Wittkampf, et al, Myocardial lesion depth with circular electroporation ablation, Circ Arrhythm Electrophysiol, 2012, 5, pp. 581-586.
Wmmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi : 10.1007/S00270-014-0905-2.
Wood et al., Technologies for Guidance of Radiofrequency Ablation in the Multimodality Interventional Suite of the Future, Jan. 2007, National Institutes of Health, pp. 1-26.
Wright, On a relationship between the arrhenius parameters from thermal damage studies, Technical Brief, Journalof Biomechanical Engineering, Transactions of the ASME, Apr. 2003, vol. 125, pp. 300-304.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sol, 2007. 35(5): p. 1541-1549.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Ybarra, Gary A, et al. "Breast Imaging using Electrical Impedance Tomography." in Suri, U.S., R.M. Rangayyan, and S. Laxminarayan, Emerging Technologies in Breast Imaging and Mammography2008: American Scientific Publishers.
Zhang, Y., et al., MR imaging to assess immediate response to irreversible electroporation for targeted ablation of liver tissues: preclinical feasibility studies in a rodent model. Radiology, 2010. 256(2): p. 424-32.
Zhao, J. et al. "Irreversible electroporation reverses resistance to immune checkpoint blockade in pancreatic cancer". Nature Communications (2019) 10:899, 14 pages.
Zhao, Y. et al., "Characterization of conductivity changes during high-frequency irreversible electroporation for treatment planning," IEEE Transactions on Biomedical Engineering, vol. 65, No. 8, pp. 1810-1819, 2017.
Zhou, et al, Electroporation-mediated transfer of plasmids to the lung results in reduced TLR9 signaling and Inflammation, Gene Therapy, Mar. 8, 2007, 14, pp. 775-780.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic

(56) References Cited

OTHER PUBLICATIONS

Hyperplasia (BPH): Clinical Outcome After 5 Years. (Abstract) Presented at 2001 AUA National Meeting, Anaheim, CA—Jun. 5, 2001. 1 page.

Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.

Onik, and Rubinsky, Irreversible electroporation: First patient experience focal therapy of prostate cancer, Irreversible Electroporation, BIOMED, pp. 235-247.

Onik, et al, Irreversible electroporation: Implications for prostate ablation, Technology in Cancer Research and Treatment, Aug. 2007, vol. 6, No. 4, pp. 295-300.

Onik, et al., Sonographic Monitoring of Hepatic Cryosurgery in an Experimental Animal Model, AJR American J. of vol. 144, pp. 1043-1047, May 1985.

Onik, et al., Ultrasonic Characteristics of Frozen Liver, Cryobiology, vol. 21, pp. 321-328, 1984.

Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.

Onik, G., P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Apply. Neurophysiol., 1976. 39: p. 69-76.

Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

Pakhomova, O. N., Gregory, B., Semenov I., and Pakhomov, A. G., BBA—Biomembr., 2014, 1838, 2547-2554.

Partridge, B. R. et al., "High-Frequency Irreversible Electroporation for treatment of Primary Liver Cancer: A Proof-of-Principle Study in Canine Hepatocellular Carcinoma," J. Vase. Interv. Radiol., vol. 31, No. 3, 482-491.e4, Mar. 2020, 19 pages.

Paszek et al., "Tensional homeostasis and the malignant phenotype." Cancer Cell, vol. 8, pp. 241-254 (2005).

Pavselj, N. et al. The course of tissue permeabilization studied on a mathematical model of a subcutaneous tumor in small animals. IEEE Trans Biomed Eng 52, 1373-1381 (2005).

Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).

PCT Application No. PCT/2011/062067, International Preliminary Report on Patentability dated May 28, 2013. 7 pages.

PCT Application No. PCT/2011/066239, International Preliminary Report on Patentability dated Jun. 25, 2013. 7 pages.

PCT Application No. PCT/US09/62806, International Search Report (Jan. 19, 2010), Written Opinion (Jan. 19, 2010), International Preliminary Report on Patentability (Jan. 4, 2010), 15 pgs.

PCT Application No. PCT/US10/53077, International Search Report (Aug. 2, 2011), Written Opinion (Aug. 2, 2011). and International Preliminary Report on Patentability (Apr. 17, 2012).

PCT Application No. PCT/US15/30429, International Search Report and Written Opinion dated Oct. 16, 2015, 19 pages.

PCT Application No. PCT/US15/30429, International Report on Patentability dated Nov. 15, 2016. 7 pages.

PCT Application No. PCT/US15/65792, International Search Report (Feb. 9, 2016), Written (Feb. 9, 2016), and International Preliminary Report on Patentability (Jun. 20, 2017), 15 pages.

PCT Application No. PCT/US19/51731, International Preliminary Report on Patentability dated Mar. 23, 2021, 13 pages.

PCT Application No. PCT/US19/51731, International Search Report and Written Opinion dated Feb. 20, 2020, 19 pgs.

PCT Application No. PCT/US2004/043477, International Search Report (Aug. 26, 2005), Written Opinion (Aug. 26, 2005), and International Preliminary Report on Patentability (Jun. 26, 2006). 10 pages.

PCT Application No. PCT/US2009/042100, International Search Report (Jul. 9, 2009), Written Opinion (Jul. 9, 2009), International Preliminary Report on Patentability (Nov. 2, 2010).

PCT Application No. PCT/US2010/030629, International Search Report (Jul. 15, 2010), Written Opinion (Jul. 15, 2010), and International Preliminary Report on Patentability (Oct. 11, 2011).

PCT Application No. PCT/US2011/062067, International Search Report and Written Opinion dated Jul. 25, 2012.

PCT Application No. PCT/US2011/066239, International Search Report (Aug. 22, 2012), and Written Opinion (Aug. 22, 2012).

PCT International Search Report and Written Opinion from PCT/US2010/053077, dated Aug. 2, 2011.

PCT International Search Report for PCT/US10/29243 dated Jul. 30, 2010, 4 pages.

PCT International Search Report for WO 2012/051433 mailed May 30, 2012. 6 pages.

Pech, et al, Irreversible electroporation of renal cell carcinoma: A first-in-man phase I clinical study, Cardiovasc Intervent Radiol, Aug. 15, 2010.

Pending Application No. PCT/US21/51551, International Search Report and Written Opinion dated Dec. 29, 2021, 14 pages.

Pending Application No. PCT/US23/15118, International Search Report and Written Opinion dated Jul. 31, 2023, 18 pages.

Pending Application No. PCT/US23/76626, International Search Report and Written Opinion, dated Apr. 17, 2024, 12 pages.

Persichetti F. et al, "Normal and Expanded Huntington's Disease Gene Alleles Produce Distinguishable Proteins Due To Translation Across the Cag Repeat", Molecular Medicine, Feinstein Institute for Medical Research, Washington, DC; US, (19950501), vol. 1, No. 4, ISSN 1076-1551, pp. 374-383, XP000997528.

Philips, IntelliVue Patient Monitor, Jan. 2008, Philips, pp. 1-532 (Year: 2008).

Phillips, et al, Irreversible electroporation on the small intestine, British Journal of Cancer, 2012, pp. 1-6.

Phillips, M., Maor, E. & Rubinsky, B. Nonthermal Irreversible Electroporation for Tissue Decellularization. J. Biomech. Eng, doi: : 10.1115/1.4001882 (2010). 8 pages.

Pinero, et al., Apoptotic and Necrotic Cell Death Are Both Induced by Electroporation in HL60 Human Promyeloid Leukaemia Cells, Apoptosis, vol. 2, No. 3, 330-336, Aug. 1997.

Polajzer, T. et al., "Cancellation effect is present in high-frequency reversible and irreversible electroporation," Bioelectrochemistry, vol. 132, 2020, 11 pages.

Polak et al., "On the Electroporation Thresholds of Lipid Bilayers: Molecular Dynamics Simulation Investigations." The Journal of Membrane Biology, vol. 246, pp. 843-850 (2013).

Precision Office Tuna System, "When Patient Satisfaction is Your Goal." Product Literature Published by VidaMed, Inc., 11 pages (2001).

Pucihar et al., "Numerical determination of transmembrane voltage induced on irregularly shaped cells." Annals of Biomedical Engineering, vol. 34, pp. 642-652 (2006).

Qiao et al. Electrical properties of breast cancer cells from impedance measurement of cell suspensions, 2010, Journal of Physics, 224, 1-4 (2010).

Radeva, et al, Induction of apoptosis and necrosis in cancer cells by electric fields, electromagnetic fields, and photodynamically active quinoids, Electromagnetic Biology and Medicine, 2003, 23, pp. 185-200.

Rajagopal, V. and S.G. Rockson, Coronary restenosis: a review of mechanisms and management, The American Journal of Medicine, 2003, 115(7): p. 547-553.

Rebersek, M. and D. Miklavcic, "Advantages and Disadvantages of Different Concepts of Electroporation Pulse Generation," Automatika 52(2011) 1, 12-19.

Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.

(56) References Cited

OTHER PUBLICATIONS

Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
"TUNA—Suggested Local Anesthesia Guidelines." Published by VidaMed, Inc. (1 page) (2001).
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Adeyanju, et al., The improvement irreversible electroporation therapy using saline-irrigated electrodes: A theoretical study, Technology in Cancer Researchand Treatment, Aug. 2011, vol. 10, No. 4, pp. 347-360.
Agerholm-Larsen, B., et al., "Preclinical Validation of Electrochemotherapy as an Effective Treatment for Brain Tumors", Cancer Research 71: 3753-3762 (2011).
Al-Khadra, et al, The role of electroporation in defibrillation, Circulation Research, Oct. 27, 2000, 87, pp. 797-804.
Al-Sakere et al., "Tumor ablation with irreversible electroporation." PLoS ONE, Issue 11, e1135, 8 pages, 2007.
Al-Sakere, et al, A study of the immunological response to tumor ablation with irreversible electroporation, Technology in Cancer Research and Treatment, Aug. 2007, vol. 6, No. 4, pp. 301-305.
Alberts et al., "Molecular Biology of the Cell," 3rd edition, Garland Science, New York, 1994, 1 page.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Alinezhadbalalami, N. et al., "Generation of Tumor-activated T cells Using Electroporation", Bioelectrochemistry 142 (2021) 107886, Jul. 13, 2021, 11 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C. B. et al., "Theoretical Considerations of Tissue Electroporation Wth High-Frequency Bipolar Pulses," IEEE Trans. Biomed. Eng., vol. 58, No. 5, 1474-1482, 2011, 9 pages.
Arena, C.B., et al., "A three-dimensional in vitro tumor platform for modeling therapeutic irreversible electroporation." Biophysical Journal, 2012.103(9): p. 2033-2042.
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Arena, et al, Theoretical considerations of tissue electropration with high frequency biopolar pulses, IEEEE, pp. 1-7, (2010).
Arena, et al, Towards the development of latent heat storage electrodes for electroporation-based therapies, Applied Physics Letters, 2012, 101, 083902, pp. 1-4.
Asami et al., "Dielectric properties of mouse lymphocytes and erythrocytes." Biochimica et Biophysica Acta (BBA)—Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).

Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Bayazitoglu, et al, An overview of nanoparticle assisted laser therapy, International Journal of Heat and Mass Transfer, Sep. 11, 2013, 67, pp. 469-486.
Beebe, S.J., et al., "Diverse effects of nanosecond pulsed electric fields on cells and tissues", DNA and Cell Biology, 22(12): 785-796(2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1,2001, pp. 211-215, vol. I, Piscataway, NJ, USA.
Beebe, S.J., et al.,, "Nanosecond, high-intensity pulsed electric fields induce apoptosis in human cells", FASEB J, 17(9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E., et al., "Characterization of Irreversible Electroporation Ablation in In Vivo Procine Liver" Am. J. Roentgenol. 198(1), W62-W68 (2012).
Benz. R., et al. "Reversible electrical breakdown of lipid bilayer membranes: a charge-pulse relaxation study". J Membr Biol, 48(2): p. 181-204 (1979).
Bertacchini, et al., Design of an irreversible electroporation system for clinical use, Technology in Cancer Research and Treatment, Aug. 2007, vol. 6, No. 4, pp. 313-320.
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17(1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.

(56) References Cited

OTHER PUBLICATIONS

Bondarenko, A. and G. Ragoisha, Eis spectrum analyser (the program is available online at http://www.abc.chemistrybsu.by/vi/analyser/) (Accessed Aug. 28, 2020).
Boone, K., Barber, D. & Brown, B. Review—Imaging with electricity: report of the European Concerted Action on Impedance Tomography. J. Med. Eng. Technol. 21, 201-232 (1997).
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bower et al., "Irreversible electroporation of the pancreas: definitive local therapy without systemic effects." Journal of surgical oncology, 2011. 104(1): p. 22-28.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Buist et al., "Efficacy of multi-electrode linear irreversible electroporation," Europace, vol. 23, No. 3, pp. 464-468, 2021, 5 pages.
Mazurek, et al, Effect of Short HV Pulses in Bacteria and Fungi, 1995, vol. 2, No. 3, pp. 418-425.
McCall, Nanoknife, liposomal doxorubicin show efficacy against liver cancer, European Congress of Radiology, Mar. 1, 2011, pp. 1-2.
McCarley, and Soulen, Percutaneous ablation of hepatic tumors, Seminars in Interventional Radiology, 2010, vol. 27, No. 3, pp. 255-260.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
McWilliams, et al, Image-guided tumor ablation: Emerging technologies and future directions, Seminars in Interventional Radiology, 2010, vol. 27, No. 3, pp. 302-313.
Mercadal, B. et al., "Avoiding nerve stimulation in irreversible electroporation: A numerical modeling study," Phys. Med. Biol., vol. 62, No. 20, 8060-8079, 2017, 28 pages.
Mercadal, Borja et al. "Dynamics of Cell Death After Conventional IRE and H-FIRE Treatments", Annals of Biomedical Engineering, vol. 48, No. 5, 2020, p. 1451-1462.
Miklavcic, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Miklavcic, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavcic, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Mir et al., "Mechanisms of Electrochemotherapy" Advanced Drug Delivery Reviews 35:107-118 (1999).

Mir, Chapter 1 application of electroporation gene therapy: Past, current and future, Electroporation Protocols: Preclinical and Clinical Gene Medicine, Methods in Molecular Biology, vol. 423, 2008, pp. 3-17.
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Orlowski, Introduction: Electropermeabilization as a new drug delivery approach, Methods in Molecular Medicine, 2000, vol. 37, pp. 99-117.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001. 1 page.
Naslund, Michael J., Transurethral Needle Ablation of the Prostate, Urology, vol. 50, No. 2, Aug. 1997, 6 pages.
Nath, S., Dimarco, J. P. and Haines, D. E. (1994), Basic Aspects of Radiofrequency Catheter Ablation. Journal of Cardiovascular Electrophysiology, 5: 863-876.
Neal II, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.
Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer Other Heterogeneous Systems, Ann Biomed Eng, 2009, 37(12): p. 2615-2625.
Neal II et al., "A Case Report on the Successful Treatment of a Large Soft-Tissue Sarcoma with Irreversible Electroporation," Journal of Clinical Oncology, 29, pp. 1-6, 2011.
Neal Re II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Neal, et al, A study using irreversible electroporation to treat large, irregular tumors in a canine patient, 32nd Annual International Conference of the IEEE EMBS, IEEE, Aug. 2010, pp. 2747-2750.
Neal, et al, An "Off-the-Shelf" system for intraprocedural electrical current evaluation and monitoring of irreversible electroporation therapy, Cardiovasc Intervent Radiol, Feb. 27, 2014. 6 pages.

(56) References Cited

OTHER PUBLICATIONS

Nesin et al., "Manipulation of cell vol. and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, 7, pp. 841-845, 1982.
Neumann, et al., Permeability Changes Induced by Electric Impulses in Vesicular Membranes, J. Membrane Biol., vol. 10, pp. 279-290, 1972.
Neven et al., Epicardial Linear Electroporation Ablation and Lesion Size, Department of Cardiology, University of Medical Utrecht, Aug. 2014, vol. 11, No. 8.
Nikolova, B., et al., "Treatment of Melanoma by Electroporation of Bacillus Calmette-Guerin". Biotechnology & Biotechnological Equipment, 25(3): p. 2522-2524 (2011).
Nikolski, et al., Electroporation of the heart, Europace, 2005, 7, pp. S146-S154.
Notice of Allowance dated Jul. 24, 2024 for U.S. Appl. No. 16/938,778 (pp. 1-2).
Nuccitelli, R., et al., "A new pulsed electric field therapy for melanoma disrupts the tumor's blood supply and causes complete remission without recurrence", Int J Cancer, 125(2): p. 438-45 (2009).
O'Brien, T. J. et al., "Effects of internal electrode cooling on irreversible electroporation using a perfused organ model," Int. J. Hyperth., vol. 35, No. 1, pp. 44-55, 2018.
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Ohio Environmental Protection Agency, Ground Water Flow and Fate and Transport Modeling, State of Ohio Environmental Protection Agency, 2007, pp. 14-1-14-32.
Okino, et al., Effects of High-Voltage Electrical Impulse and an Anticancer Drug on In Vivo Growing Tumors, Journal of Cancer Research, vol. 78, pp. 1319-1321, 1987.
Rols, M.P., et al., Highly Efficient Transfection of Mammalian Cells by Electric Field Pulses: Application to Large Volume of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rowland, et al, Transvenous ablation of atrioventricular conduction with a low energy power source, Br Heart J, 1989, 62, pp. 361-366.
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Rubinsky, L. et al., "Electrolytic Effects During Tissue Ablation by Electroporation," Technol. Cancer Res. Treat., vol. 15, No. 5, NP95-103, 2016, 9 pages.
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Saldanha, et al., Current tumor ablation technologies: Basic science and device review, Seminars in Interventional Radiology, 2010, vol. 27, No. 3, pp. 247-254.
Salford, L.G., et al., "A new brain tumour therapy combining bleomycin with in vivo electropermeabilization", Biochem. Biophys. Res. Commun., 194(2): 938-943 (1993).
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Salmanzadeh et al., "Investigating dielectric properties of different stages of syngeneic murine ovarian cancer cells" Biomicrofiuidics 7, 011809 (2013), 12 pages.
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spectroscopy," Measurement Science and Technology, vol. 22, No. 11, p. 115601,2011.
Sanders, et al., Nanosecond pulse generator with scalable pulse amplitude, IEEE, 2008, pp. 65-68.
Sankaranarayanan, et al., Effect of irreversible electroporation on cell proliferation in fibroblasts, Proc. ESA Annual Meeting on Electrostatics, 2011, pp. 1-8.
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort cancer Cells from Dilute Whole Blood Samples." Biosensors & Bioelectronics, 8 pages (2011).
Sano, M. B. et al., "Burst and continuous high frequency irreversible electroporation protocols evaluated in a 3D tumor model," Phys. Med. Biol., vol. 63, No. 13, 2018, 17 pages.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
Sano, M. B., et al., "Towards the creation of decellularized organ constructs using irreversible electroporation and active mechanical perfusion", Biomedical Engineering Online, Biomed Central LTD, London, GB, vol. 9, No. 1,Dec. 10, 2010, p. 83.
Saur et al., "CXCR4 expression increases liver and lung metastasis in a mouse model of pancreatic cancer." Gastroenterology, vol. 129, pp. 1237-1250 (2005).
Savader, et al."Treatment of Hemodialysis Catheter-associated Fibrin Sheaths by rt-PA Infusion: Critical Analysis of 124 Procedures," J Vasc Intery Radiol 2001; 12:711-715.
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Schoenbach, et al, Bioelectric effects of intense nanosecond pulses, IEEE Transactions on Dielectric and Electrical Insulation, 2007, vol. 14, Iss. 5, pp. 1088-1109.

(56) References Cited

OTHER PUBLICATIONS

Seibert et al., "Clonal variation of MCF-7 breast cancer cells in vitro and in athymic nude mice." Cancer Research, vol. 43, pp. 2223-2239 (1983).
Seidler et al., "A Cre-OoxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi: 10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al, Tumor blood flow modifying effect of electrochemotherapy with Bleomycin, Anticancer Research, 1999, 19, pp. 4017-4022.
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Shafiee, et al, A preliminary study to delineate irreversible electroporation from thermal damage using the Arrhenius equation, Journal of Biomedical Engineering, Jul. 2009, vol. 131, 074509, pp. 1-5.
Shao, Qi et al. Engineering T cell response to cancer antigens by choice of focal therapeutic conditions, International Journal of Hyperthermia, 2019, DOI: 10.1080/02656736.2018.1539253. 10 pages.
Sharma, A. et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, et al, Percutaneous ethanol injection therapy for hepatocellular carcinoma: Results in 146 patients, AJR, May 1993, 160, pp. 1023-1028.
Soden, et al, Successful application of targeted electrochemotherapy using novel flexible electrodes and low dose bleomycin to solid tumors, Cancer Letters, 2006, 232 pp. 300-310.
Son, et al, Basic features of a cell electroporation model: illustrative behavior for tw overy different pulses, J Membrane Biol, Jul. 22, 2014, 247, pp. 1209-1228.
Song, Z.Q., et al., Mechanisms for steep pulse irreversible electroporation technology to kill human large cell lung cancer cells L9981. International Journal of Clinical and Experimental Medicine, 2014. 7(8): p. 2386-2394.
Szot et al., "3D in vitro bioengineered tumors based on collagen 1 hydrogels." Biomaterials vol. 32, pp. 7905-7912 (2011).
Talele, S. and P. Gaynor, "Non-linear time domain model of electropermeabilization: Effect of extracellular conductivity and applied electric field parameters", Journal of Electrostatics, 66(5-6): p. 328-334 (2008).
Duck, F. A., Physical Properties of Tissue: A Comprehensive Reference Book. London: Harcourt Brace Jovanovich, 1990, 358 pages.
Dunki-Jacobs, et al., Evaluation of resistance as a measure of successful tumor ablation during irreversible electroporation of the pancreas, American College of Surgeons, Feb. 2014, vol. 218, No. 2, pp. 179-187.
Dupuy, and Shulman, Current status of thermal ablation treatments for lung malignancies, Seminars in Interventional Radiology, 2010, vol. 27, No. 3, pp. 268-275. Radiol, Dec. 30, 2010, 34, pp. 268-275.
Dupuy, et al, Irreversible electroporation in a swine lung model, Cardiovasc Intervent Radiol, Dec. 30, 2010, 34, pp. 391-395.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980, pp. 42-49.
Ermolina et al., "Study of normal and malignant white blood cells by time domain dielectric spectroscopy." IEEE Transactions on Dielectrics and Electrical Insulation, 8 (2001) pp. 253-261.
Esser, At., et al., "Towards solid tumor treatment by irreversible electroporation: intrinsic redistribution of fields and currents in tissue". Technol Cancer Res Treat, 6(4): p. 261-74 (2007).
Esser, At., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997, 9 pages.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Gabriel, C, Dielectric properties of biological tissue: variation with age. Bioelectromagnetics, 2005. Suppl 7: p. S12-8.
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.

(56) References Cited

OTHER PUBLICATIONS

Garcia, et al, Irreversible electroporation (IRE) to treat brain tumors, Proceedings of the ASME 2008 Summer Bioengineering Conference (SBC2008), Jun. 25, 2008, pp. 6-7.

Garcia, et al, Non-thermal irreversible electroporation for deep intracranial disorders, 32nd Annual International Conference of the IEEE EMBS, IEEE, Aug. 2010, pp. 2747463.

Garcia, et al, Position paper concerning the use of Angiodynamics' nanoknife system for treatment of brain gliomas, Virgina Tech—Wake Forest University, May 22, 2013, pp. 1-46.

Garcia, et al., "A Parametric Study Delineating Irreversible Electroporation from Thermal Damage Based on a Minimally Invasive Intracranial Procedure," Biomed Eng Online, vol. 10:34, 22 pages, 2011.

Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).

Garcia, P. A., et al., "Towards a predictive model of electroporation-based therapies using pre-pulse electrical measurements," Conf Proc IEEE Eng Med Biol Soc, vol. 2012, pp. 2575-2578, 2012.

Garcia, p. A., et al., Intracranial Nonthermal Irreversible Electroporation: In Vivo Analysis. Journal of Membrane Biology, 2010. 236(1): p. 127-136.

Garcia, P.A., R.V. Davalos, and D. Miklavcic, A Numerical Investigation of the Electric and Thermal Cell Kill Distributions in Electroporation-Based Therapies in Tissue. Plos One, 2014. 9(8).

Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.

Garcla-Sanchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.

Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).

Gauger, et al., A Study of Dielectric Membrane Breakdown in the Fucus Egg, J. Membrane Biol., vol. 48, No. 3, pp. 249-264, 1979.

Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.

Gehl, et al., In Vivo Electroporation of Skeletal Muscle: Threshold, Efficacy and Relation to Electric Field Distribution, Biochimica et Biphysica Acta 1428, 1999, pp. 233-240.

Gencer, et al., Electrical Impedance Tomography: Induced-Current Imaging Achieved with a Multiple Coil System, IEEE Transactions on Biomedical Engineering, vol. 43, No. 2, Feb. 1996, pp. 139-149.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Gilbert, T. W., et al., "Decellularization of tissues and organs", Biomaterials, Elsevier Science Publishers, Barking, GB, vol. 27, No. 19, Jul. 1, 2006, pp. 3675-3683.

Gimsa et al., "Dielectric spectroscopy of single human erythrocytes at physiological ionic strength: dispersion of the cytoplasm." Biophysical Journal, vol. 71, pp. 495-506 (1996).

Glidewell, et al., The Use of Magnetic Resonance Imaging Data and the Inclusion of Anisotropic Regions in Electrical Impedance Tomography, Biomed, Sci. Instrum. 1993; 29: 251-7.

Golberg, A. and Rubinsky, B., "A statistical model for multidimensional irreversible electroporation cell death in tissue." Biomed Eng Online, 9, 13 pages, 2010.

Gothelf, et al., Electrochemotherapy: Results of Cancer Treatment Using Enhanced Delivery of Bleomycin by Electroporation, Cancer Treatment Reviews 2003: 29: 371-387.

International Search Report for PCT/US2010/022011 ISR dated Aug. 30, 2010.

International Search Report for PCT/US2010/022011 WOSA dated Aug. 30, 2010.

International Search Report for PCT/US2010/029243 IPRP dated Oct. 4, 2011.

International Search Report for PCT/US2010/029243 WOSA dated Jul. 30, 2010.

International Search Report for PCT/US2010/036734 IPRP dated Nov. 29, 2011.

International Search Report for PCT/US2010/036734 ISR dated Dec. 23, 2010.

International Search Report for PCT/US2010/036734 WOSA dated Dec. 23, 2010.

International Search Report for PCT/US2010/053077 IPRP dated Apr. 17, 2012.

International Search Report for PCT/US2011/024909 IPRP dated Aug. 21, 2012.

International Search Report for PCT/US2011/024909 ISR dated Oct. 18, 2011.

International Search Report for PCT/US2011/024909 WOSA dated Oct. 18, 2011.

International Search Report for PCT/US2011/025003 IPRP dated Aug. 21, 2012.

International Search Report for PCT/US2011/025003 ISR dated Oct. 24, 2011. 10 pages.

International Search Report for PCT/US2011/025003 WOSA dated Oct. 24, 2011.

International Search Report for PCT/US2011/056177 ESO dated Mar. 28, 2014.

International Search Report for PCT/US2011/056177 IPRP dated Apr. 16, 2013. 6 pages.

International Search Report for PCT/US2011/056177 ISR dated May 30, 2012.

International Search Report for PCT/US2011/056177 WOSA dated May 30, 2012.

International Search Report for PCT/US2011/062067 IPRP dated May 28, 2013.

International Search Report for PCT/US2011/062067 ISR dated Jul. 25, 2012.

International Search Report for PCT/US2011/062067 WOSA dated Jul. 25, 2012.

International Search Report PCT-US-07-000084 ISR dated Dec. 14, 2007, 2 pages.

International Search Report PCT/US07/00084 WOSA dated Dec. 14, 2007, 7 pages.

International Search Report PCT/US2009/038661 ISR dated Jun. 12, 2009.

Issa, et al, Recent Reports: The TUNA procedure for BPH: Review of the technology, Infections in Urology, Jul. 1998, 8 pages.

ISSA, et al., Specialty Surgery: The TUNA procedure for BPH: Basic procedure and clinical results, Infections in Urology, Sep. 1998, 6 pages.

ISSA, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998. 8 pages.

Ivanusa, et al., MRI Macromolecular Contrast Agents as Indicators of Changed Tumor Blood Flow, Radiol. Oncol. 2001; 35(2): 139-47.

Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.

Ivorra et al., "In vivo electric impedance measurements during and after electroporation of rat live." Bioelectrochemistry, vol. 70, pp. 287-295 (2007).

Ivorra et al., "In vivo electrical conductivity measurements during and after tumor electroporation: conductivity changes reflect the treatment outcome." Physics in Medicine and Biology, vol. 54, pp. 5949-5963 (2009).

(56) References Cited

OTHER PUBLICATIONS

Ivorra, "Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Ivorra, et al., Impedance analyzer for in vivo electroporation studies, Proceedings of the 28th IEEE EMBS Annual International Conference, IEEE, Aug. 30, 2006, pp. 5056-5059.
Jan Ko et al, "New anti-huntingtin monoclonal antibodies: implications for huntingtin conformation and its binding proteins", Brain Research Bulletin, Elsevier Science Ltd, Oxford, GB, (Oct. 1, 2001), vol. 56, No. 3-4, doi:10.1016/S0361-9230(01)00599-8, ISSN 0361-9230, pp. 319-329, XP002509144 (Oct.-Nov. 2001).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8: 16, 9 Pages (2008).
Jiang, et al, Membrane-targeting approaches for enhanced cancer cell destruction with irreversible electroporation, Annuals of Biomedical Engineering, Aug. 15, 2013.
Jordan, D.W., et al., "Effect of pulsed, high-power radiofrequency radiation on electroporation of mammalian cells", Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Kanduser, et al, Cell membrane fluidity related to electroporation and resealing, Eur Biophys J, Oct. 8, 2006, 35, pp. 196-204.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita et al., "Electroporation of cell membrane visualized under a pulsed-laser fluorescence microscope." Biophysical Journal, vol. 53, pp. 1015-1019 (1988).
Kinosita et al., "Voltage-induced pore formation and hemolysis of human erythrocytes." Biochimica et Biophysica Acta (BBA)—Biomembranes, 471 (1977) pp. 227-242.
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Bulvik, B. E. et al. "Irreversible Electroporation versus Radiofrequency AblationD: A Comparison of Local and Systemic Effects in a Small Animal Model," Radiology, vol. 280, No. 2, 2016, 413-424.
Butikofer, R. et al., "Electrocutaneous Nerve Stimulation-11 Stimulus Waveform Selection," IEEE Trans. Biomed. Eng., vol. BME-26, No. 2, 69-75, 1979, abstract only, 2 pages.
Butikofer, R. et al., "Electrocutaneous Nerve Stimulation-I: Model and Experiment," IEEE Trans. Biomed. Eng., vol. BME-25, No. 6, 526-531, 1978,6 pages.
Cannon et al., "Safety and early efficacy of irreversible electroporation for hepatic tumors in proximity to vital structures." Journal of Surgical Oncology, 6 pages (2012).
Carmi, and Georgiades, Combination percutaneous and intraarterial therapy for the treatment of hepatocellular carcinoma: A review, Seminars in Interventional Radiology, 2010, vol. 27, No. 3, pp. 296-301.
Carpenter A.E. et al., "CellProfiler: image analysis software for identifying and quantifying cell phenotypes." Genome Biol. 2006; 7(10): R100. Published online Oct. 31, 2006, 11 pages.
Carson, et al., Improving patient satisfaction, BPH management strategies, Supplement to Urology Times, May 2001, Vo. 29, Suppl. 1, pp. 1-22.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001. 1 page.
Chang, D.C., "Cell Poration and Cell-Fusion Using an Oscillating Electric-Field". Biophysical Journal, 56(4): p. 641-652 (1989).
Charpentier, et al., Irreversible electroporation of the liver an dliver hilum in swine, HBP, 2011, 13, pp. 168-173.
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.
Chen, M.T., et al., "Two-dimensional nanosecond electric field mapping based on cell electropermeabilization", PMC Biophys, 2(1 ):9 (2009).
Choi, et al, Preclinical analysis of irreversible electroporation on rat liver tissues using a microfabricated electroporator, Tissue Engineering Part C, 2010, vol. 16, No. 6, pp. 1245-1253.
Clark et al., "The electrical properties of resting and secreting pancreas." The Journal of Physiology, vol. 189, pp. 247-260 (1967).
Coates, C.W., et al., "The Electrical Discharge of the Electric Eel, Electrophorous Electricus," Zoologica, 1937, 22(1), pp. 1-32.
Cook, et al, ACT3: a high-speed, high-precision electrical impedance tomograph, IEEE Transactions on Biomedical Engineering, 1994, vol. 41, No. 8, pp. 713-722.
Corovic et al., "Analytical and numerical quantification and comparison of the local electric field in the tissue for different electrode configurations," Biomed Eng Online, 6, 14 pages, 2007.
Cosman, E. R. et al., "Electric and Thermal Field Effects in Tissue Around Radiofrequency Electrodes," Pain Med., vol. 6, No. 6, 405-424, 2005, 20 pages.
Cowley, Good News for Boomers, Newsweek, Dec. 30, 1996/Jan. 6, 1997, p. 1.
Cox, et al., Surgical Treatment of Atrial Fibrillation: A Review, Europace (2004) 5, S20-S-29.
Craiu, Scadden, Chapter 22 flow electroporation with pulsed electric fields for purging tumor cells, Electroporation Protocols: Preclinical and Clinical Gene Medicine, Methods in Molecular Biology, vol. 423, 2008, pp. 301-310.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Crowley, Electrical Breakdown of Biomolecular Lipid Membranes as an Electromechanical Instability, Biophysical Journal, vol. 13, pp. 711-724, 1973.

(56) References Cited

OTHER PUBLICATIONS

Cukjati, et al, Real time electroporation control for accurate and safe in vivo non-viral gene therapy, Bioelectrochemistry, Nov. 10, 2006, 70, pp. 501-507.
Dahl et al., "Nuclear shape, mechanics, and mechanotransduction." Circulation Research vol. 102, pp. 1307-1318 (2008).
Daniels, Rubinsky, Electrical field and temperature model of nonthermal irreversible electroporation in heterogeneous tissues, Journal of Biomedical Engineering, Jul. 2009, vol. 131, 071006, pp. 1-12.
Daniels, Rubinsky, Temperature modulation of electric fields in biological matter, PLOS One, vol. 6, Iss. 6, e20877, pp. 1-9, Jun. 2011.
Daskalov, I., et al, "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002, pp. 400-403.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi: 10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, pp. 1-237.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap junctional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Deodhar, et al, Irreversible electroporation near the heart: Ventricular arrhythmias can be prevented with ECG synchronization, AJR, Mar. 2011, 196, pp. W330-W335.
Deodhar, et al, Renal tissue ablation with irreversible electroporation: Preliminary results in a porcine model, Technology and Engineering, Urology, 2010, 1-7.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Du Pre, et al, Minimal coronary artery damage by myocardial electroporation ablation, European Society of Cardiology, Europace, May 31, 2012, pp. 1-6.
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields-A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses". Part I. Increased efficiency of permeabilization. Bioelectrochemistry, 54(1): p. 83-90 (2001).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).
Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.
Kroeger, et al., Curvature-driven pore growth in charged membranes during charge-pulse and voltage-clamp experiments, Biophysical Journal, Feb. 2009, 96, 3, pp. 907-916.
Kurup, Callstrom, Image-guided percutaneous ablation of bone and soft tissue tumors, Seminars in Interventional Radiology, 2010, vol. 27, No. 3, pp. 276-284.
Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lavee, et al., "A Novel Nonthermal Energy Source for Surgical Epicardial Atrial Ablation: Irreversible Electroporation," The Heart Surgery Forum #2006-1201, vol. 10 (2): 96-101 (2007).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, Cassinian Oval, Nov. 2004, Mathematics Department of The University of California at Irvine, pp. 1-5.
Lee, E. W. et al. Advanced Hepatic Ablation Technique for Creating Complete Cell Death : Irreversible Electroporation. Radiology 255, 426-433, doi: 10.1148/radiol.10090337 (2010).
Lee, et al, Imaging guided percutaneous irreversible electroporation: Ultrasound and immunohistological correlation, Technology in Cancer Research and Treatment, Aug. 2007, vol. 6, No. 4, pp. 287-293.
Lee, et al, Irreversible electroporation: A novel image-guided cancer therapy, Gut and Liver, Sep. 2010, vol. 4, Supp. 1, pp. S99-S104.
Lee, R. C., D. J. Canaday, and S. M. Hammer. Transient and stable ionic permeabilization of isolated skeletal muscle cells after electrical shock. J. Burn Care Rehabil. 14:528-540, 1993.
Li, W., et al., "The Effects of Irreversible Electroporation (IRE) on Nerves" PloS One, Apr. 2011, 6(4), e18831. 7 pages.
Lin, et al., An optically induced cell lysis device using dielectrophoresis, Applied Physics Letters, Jan. 20, 2009, 94, 033901, pp. 1-3.

(56) References Cited

OTHER PUBLICATIONS

Lion, et al., Poly(I:C) enhances the susceptibility of leukemic cells to NK cell cytotoxicity and phagocytosis by DC, PLOS ONE, vol. 6, Iss. 6, e20952, pp. 1-10, Jun. 17, 2011.

Liu, et al., Measurement of Pharyngeal Transit Time by Electrical Impedance Tomography, Clin. Phys. Physiol. Meas., 1992, vol. 13, Suppl. A, pp. 197-200.

Long, G., et al., "Targeted Tissue Ablation With Nanosecond Pulses", IEEE Transactions on Biomedical Engineering, 58(8) (2011).

Lu, et al., Irreversible electroporation: Ready for prime time?, Techniques in Vascular and Interventional Radiology, 2013, 16, pp. 277-286.

Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.

Lurquin, Gene Transfer by Electroporation, Molecular Biotechnology, vol. 7, 1997. 27 pages.

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.

Lynn, et al., A New Method for the Generation and Use of Focused Ultrasound in Experimental Biology, The Journal of General Physiology, vol. 26, 179-193, 1942.

Macek Lebar and Miklavcic, "Cell electropermeabilization to small molecules in vitro: control by pulse parameters." Radiology and Oncology, vol. 35(3), pp. 193-202 (2001).

Machado-Aranda, et al, Gene transfer of the Na+, K+K—ATPase B1 subunit using electroporation increases lung liquid clearance, American Journal of Respiratory and Critical Care Medicine, 2004, vol. 171, pp. 204-211.

Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.

Mahmood, F., et al., "Diffusion-Weighted MRI for Verification of Electroporation-Based Treatments", Journal of Membrane Biology 240: 131-138 (2011).

Mahmood, Gehl, Optimizing clinical performance and geometrical robustness of a new electrode device for ntracranial tumor electroporation, Bioelectrochemistry, Jan. 6, 2011, 81, pp. 10-16.

Mahnic-Kalamiza, et al., "Educational application for visualization and analysis of electric field strength in multiple electrode electroporation," BMC Med Educ, vol. 12:102, 13 pages, 2012.

Mali, et al., "The Effect of Electroporation Pulses on Functioning of the Heart," Med Biol Eng Comput (2008) 46:745-757.

Malpica et al., "Grading ovarian serous carcinoma using a two-tier system." The American Journal of Surgical Pathology, vol. 28, pp. 496-504 (2004).

Maor et al., The Effect of Irreversible Electroporation on Blood Vessels, Tech, in Cancer Res. and Treatment, vol. 6, No. 4, Aug. 2007, pp. 307-312.

Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.

Maor, et al, Intravascular irreversible electroporation: Theoretical and experimental feasibility study, 30th Annual International IEEE EMBS Conference, IEEE, Aug. 20, 2008, pp. 2051-2054.

Maor, Rubinsky, Endovascular nonthermal irreversible electroporation: A finite element analysis, Journal of Biomedical Engineering, Feb. 7, 2010, vol. 132, 031008, pp. 1-7.

Marszalek et al., "Schwan equation and transmembrane potential induced by alternating electric field." Biophysical Journal, vol. 58, pp. 1053-1058 (1990).

Martin et al., "Gene Transfer to Intact Mesenteric Arteries by Electroporation" Journal of Vascular Research, 37:372-380 (2000).

Martin, n.R.C.G., et al., "Irreversible electroporation therapy in the management of locally advanced pancreatic adenocarcinoma." Journal of the American College of Surgeons, 2012. 215(3): p. 361-369.

Martinsen, 0. G. and Grimnes, S., Bioimpedance and bioelectricity basics. Academic press, 2011.

Marty, M., et al., "Electrochemotherapy—An easy, highly effective and safe treatment of cutaneous and subcutaneous métastases: Results of ESOPE (European Standard Operating Procedures of Electrochemotherapy) study," European Journal of Cancer Supplements, 4, 3-13, 2006.

Maybody, An Overview of Image-Guided Percutaneous Ablation of Renal Tumors, Seminars in Interventional Radiology/vol. 27, No. 3, 2010, pp. 261-267.

\* cited by examiner

CONGESTIVE OBSTRUCTION PULMONARY DISEASE (COPD)

CROSS REFERENCE TO RELATED APPLICATIONS

This application claims priority to U.S. patent application Ser. No. 12/754,210, which claims priority to U.S. Provisional Application No. 61/166,386 filed Apr. 3, 2009, both of which are incorporated herein by reference.

FIELD OF THE INVENTION

The present invention relates to advances in medical procedures aimed at improving the quality and length of life of individuals with Congestive Obstructive Pulmonary Disease (COPD). More particularly, the present invention relates to a method of using Irreversible Electroporation (IRE) to ablate diseased portions of the lung to further enhance lung functions while reducing complications associated with conventional procedures.

BACKGROUND OF THE INVENTION

Chronic Obstructive Pulmonary Disease; hereinafter, COPD is a disease of the lungs wherein the airways become narrowed which leads to a restriction in the flow of air into and out of the lungs causing shortness of breath. COPD includes both chronic emphysema and chronic bronchitis and is mainly caused by noxious particle or gases, most commonly from smoking, which initiates an abnormal inflammatory response in the lung. Other causes of COPD are intense or prolonged exposure to workplace dusts and particles found in coal and gold mining, in the cotton textile industry with chemicals such as cadmium and isocyanates, fumes from welding, and non-smokers being exposed to the noxious particles and gases emitted from smokers. Lung damage, inflammation of the lung airways (alveoli), and clogged mucus in the bronchial tubes are conditions associated with bronchitis and emphysema.

FIG. 1 shows a view of a lung (10) depicting an enlarged bronchus (12) and alveoli (14) which are microscopic grape-like clusters of air sacs at the end of the smallest bronchiole (airways) (12). The alveoli (14) are where gas exchange takes place, and are regarded as the primary functional units of the lungs. Alveoli (14) are densely covered with capillaries [for sake of clarity, too small to show about the alveoli (14), but are extensions to the capillaries (16) about the bronchus (12)] wherein blood is brought to the capillaries (16) by the pulmonary artery (not shown) and carried away by the pulmonary vein (not shown). When the alveoli (14) inflate with inhaled air, oxygen diffuses into the blood in the capillaries (16) to the tissues of the body, and carbon dioxide diffuses out of the blood into the lungs (10), where it is exhaled.

Bronchitis is an inflammation of the bronchial tubes (12), or bronchi, that bring air into the lungs (10). When the cells lining the bronchi are irritated, the tiny hairs (cilia) that normally trap and eliminate particulates from the air stop working. Formation of material (mucus and phlegm) associated with irritation (inflammation) also increases; causing the passages to become clogged. Mucus/phlegm and the inflamed bronchial lining (18 of FIGS. 2A and 2B) constrict the airways causing them to become smaller and tighter which makes it difficult to get air into and out of the lungs. As an attempt to rid the constricted airways of the mucus/phlegm, the body responds with persistent, intense and severe coughing spells. Chronic bronchitis is often either misdiagnosed or neglected until it is in advanced stages.

FIGS. 2A and 2B are cross-sectional views of a normal bronchus (12) and a bronchus (12) affected by chronic bronchitis, respectively. FIG. 2A depicts the bronchus (12) with an inner bronchial wall (18) having a thickness (T1), and the airway (A1) of the bronchus (12) having a diameter (D1). FIG. 2B depicts the bronchus (12) having an inner bronchial wall (18) with a thickness (T2), and the airway (A2) of the bronchus (12) having a diameter (D2). In comparison to a normal bronchus (12), as shown in FIG. 2A, the inner bronchial wall (18) of the bronchus (12) affected by chronic bronchitis has an increased thickness (T2) which creates the decreased diameter (D2) airway (A2). The inner bronchial wall (18) becomes enlarged or swollen due to irritants within the air when air is taken in. Once the inner bronchial wall (18) is irritated, the small hairs (cilia) that normally protect the bronchus (12) from foreign matter stop working. As a result, (mucus and phlegm) associated with irritation (inflammation) forms; thereby decreasing the diameter of the airway (D2) and causing the passages to become clogged and restricted. The decreased diameter (D2) airway (A2) prevents the proper flow of air into and out of the lung inhibiting the natural functions of the lung.

Emphysema is defined as a breakdown or destruction in the walls of the alveoli causing them to become abnormally enlarged. A lung (10) affected by emphysema has enlarged and engorged alveoli (14). The breakdown or destruction of the alveoli (14) reduces the surface area available for the exchange of oxygen and carbon dioxide during breathing resulting in poor oxygenation (low oxygen and high carbon dioxide levels within the body). Also, elasticity of the lung (10) itself is decreased leading to the loss of support of the airway embedded in the lung (10) which often times leads to collapse of the airway thereby further limiting airflow.

FIGS. 3A and 3B are cross-sectional views of normal alveoli (14) and alveoli (14) affected by emphysema, respectively. FIG. 3A depicts and enlarged view of normal alveoli (14) showing the grape-like configurations or individual alveolus (20) and surrounding tissue (22). The individual alveolus (20) is tightly compacted together and is clearly defined by the surrounding tissue (22). However, with emphysema, as the alveoli (14) deteriorates or is destroyed, the surrounding tissue (22) loses its elasticity thereby causing the individual alveolus (20) to expand and become engorged, see FIG. 3B. FIG. 3B also shows that the individual alveolus (20) is much less compacted and has reduced amounts of surrounding tissue (22). Due to the inelasticity of the surrounding tissue (22), the abnormally enlarged alveoli (14) fill easily with air during inhalation/inspiration, but lose the ability to empty the lung during exhalation/expiration.

In both cases of COPD, chronic bronchitis and emphysema, the greatest reduction in airflow occurs when breathing out (exhalation/expiration) because the pressure in the chest tends to compress rather than expand the airways. A person with COPD may not be able to completely finish breathing out before needing to take another breath. A small amount of the air from the previous breath remains within the lungs when the next breath is started. Easy filling and poor emptying of the lungs leads to progressive hyperexpansion or dynamic hyperinflation of the lungs resulting in inefficient breathing mechanics. Hyperexpansion/hyperinflation of the lungs, in addition to the poor oxygenation capability, makes it progressively difficult to breathe.

In order to compensate for the breathing deficiencies, some people with advanced COPD manage to breathe faster; however, as a result, they usually develop dyspnea (chronic shortness of breath). Others, who may be less short of breath, tolerate the low oxygen and high carbon dioxide levels in their bodies, but eventually develop headaches, drowsiness and even heart failure. Advanced COPD can lead to complications beyond the lung such as depression, muscle loss, weight loss, pulmonary hypertension, osteoporosis and heart disease.

Currently, there is no cure available for chronic bronchitis; most treatment is focused on making the symptoms less severe and trying to prevent further damage. The most common types of treatment involve changes in lifestyle, medication and supplemental oxygen supply. Examples of medications are bronchodilators to open airways; corticosteroids to reduce inflammation, swelling and phlegm production; and expectorants to stop the cough that often accompanies chronic bronchitis.

Lung Volume Reduction Surgery; herein after (LVRS), is a treatment option for patients with severe emphysema. In LVRS, a physician removes approximately 20-35% of the damaged lungs or of the poorly functioning space occupying the lung tissue from each lung. By reducing the lung size, the remaining lung and surrounding muscles are able to work more efficiently, making breathing easier.

LVRS is typically performed by techniques such as thoracoscopy, sternotomy and thoracotomy. Thoracoscopy is a minimally invasive technique where three small (approximately 1 inch) incisions are made in each side, between the ribs. A video-assisted thoracic surgery (VATS) or videoscope is placed through one of the incisions which allows the surgeon to see the lungs. A special surgical stapler/grasper is inserted in the other incisions and is used to cut away the damaged areas of the lung, reseal the remaining lung from leaking blood and air, and dissolvable sutures are used to close the incisions. Thoracoscopy can be used to operate on either one or both lungs and allows for assessment and resection of any part of the lungs. Thoracopic laser treatment of portions of the lung can also be performed using this technique. In contrast, thoracopic laser treatment, although capable of ablating emphysematous tissue only at the lung surface, prohibits simultaneous bilateral lung applications.

Sternotomy or open chest surgery involves an incision being made through the breastbone to expose both lungs. Both lungs are reduced in this procedure, one after the other. The chest bone is wired together and the skin is closed. This is the most invasive technique and is used when thoracoscopy is not appropriate. This approach is usually used only for upper lobe disease of the lung.

Thoracotomy is a technique often used when the surgeon is unable to see the lung clearly through the thoracoscope or when dense adhesions (scar tissue) are found. A 5 to 12 inch long incision is made between the ribs; and the ribs are separated, but not broken, to expose the lungs. With this procedure only one lung is reduced and the muscle and skin are closed by sutures.

Although the goal of surgical therapy of COPD is to prolong life by relieving shortness in breath, preventing secondary complications, and enhancing quality of life by improving functional status, LVRS for COPD has higher surgical risks than heart surgery. Other risks associated with LVRS involve, but are not limited to: air leakage from the lung tissue at the suture line and into the chest cavity, pneumonia, bleeding, stroke, heart attack and death (resulting from worsening of any of the aforementioned complications). Because of the dangers associated with LVRS and despite advances in medical therapy, a significant number of patients with advanced COPD face a miserable existence and are at an extremely high risk for death. Over the years, a number of minimally invasive methods have been developed to address the concerns related to LVRS and to focus on the selective destruction of specific areas of undesirable tissue as an alternative to LVRS. Some of these methods include cryosurgery, non-selective chemical ablation, and ablation through radiofrequency or (RF), ultrasound, microwave, laser and thermal electric methods. However, these developments are associated, as well, with a fair amount of surgically related setbacks including complications such as large and difficult to manipulate operating mechanisms and the inability to control therapy to the affected area. This is due to the fact that ablation techniques used historically have been non-selective in that they mediate cell death with methods such as extreme heat or cold temperatures. The aforementioned methods of focal destruction of affected areas have been proven to non-selectively and adversely affect blood vessels, nerves, and connective structures adjacent to the ablation zone. Disruption of the nerves locally impedes the body's natural ability to sense and regulate homeostatic and repair processes at and surrounding the ablation region. Disruption of the blood vessels prevents removal of debris and detritus. This also prevents or impedes repair systems, prevents homing of immune system components, and generally prevents normal blood flow that could carry substances such as hormones to the area. Without the advantage of a steady introduction of new materials or natural substances to a damaged area, reconstruction of the blood vessels and internal linings become retarded as redeployment of cellular materials is inefficient or even impossible. Therefore historical ablation treatments do not leave tissue in an optimal state for self-repair in regenerating the region.

Improvements in medical techniques have rekindled interest in the surgical treatment of COPD, wherein the effects highly resemble that of LVRS but without much of the associated risks and complications of conventional LVRS techniques. These recent developments offer an opportunity to advance the regenerative process following ablation treatments. Irreversible Electroporation or (IRE) is one such technique that is pioneering the surgical field with improved treatment of tissue ablation. IRE has the distinct advantage of non-thermally inducing cell necrosis without raising/lowering the temperature of the ablation zone, which avoids some of the adverse consequences associated with temperature changes of ablative techniques such as radiofrequency (RF) ablation, microwave ablation, or even cryo-ablation. IRE also offers the ability to have a focal and more localized treatment of an affected area. The ability to have a focal and more localized treatment is beneficial when treating the delicate intricacies of organs such as the lung.

IRE is a minimally invasive ablation technique in which permeabilization of the cell membrane is effected by application of micro-second, milli-second and even nano-second electric pulses to undesirable tissue to produce cell necrosis only in the targeted tissue, without destroying critical structures such as airways, ducts, blood vessels and nerves. More precisely, IRE treatment acts by creating defects in the cell membrane that are nanoscale in size and that lead to a disruption of homeostasis while sparing connective and scaffolding structure and tissue. Thus, destruction of undesirable tissue is accomplished in a controlled and localized region while surrounding healthy tissue, organs, etc. is spared. This is different from other thermal ablation modalities known for totally destroying the cells and other important surrounding organs and bodily structures.

BRIEF SUMMARY OF THE DISCLOSURE

The present invention relates to methods for treating tissue, more particularly to treating lung tissue, through utilization of Irreversible Electroporation (IRE) to non-thermally ablate diseased tissue and enhance lung functions in patients with Congestive Obstructive Pulmonary Disorder (COPD).

It is a purpose of this invention to successfully treat target regions of diseased lung tissue affected by chronic bronchitis and emphysema through IRE ablation. IRE involves the application of energy sources capable of generating a voltage configured to successfully ablate tissue through the utilization of electrode balloons, flexible devices, probes such as monopolar, bipolar, or multiple probes (i.e. combinations of monopolar or bipolar probes arranged in a variety of configurations, monopolar and bipolar probes used together, or a series of separate or mixed groups of monopolar or bipolar probes), electrode arrays, and other devices available in electro-medicine. IRE ablation devices are available in various combinations and configurations in order to accommodate the ablation of multiple shapes, sizes and intricate portions of the diseased tissue. Examples of IRE probes applicable to this invention are described in U.S. patent application Ser. No. 12/413,332 filed Mar. 27, 2009 and 61/051,832 filed May 15, 2008, both of which are incorporated herein.

The present invention involves the method of treating COPD using IRE through open surgical, percutaneous, laparoscopical, or endotracheal procedures including the steps of obtaining access to the diseased area by positioning one or more energy delivery devices coupled to an IRE device within a target region of diseased tissue; applying IRE energy the target region to ablate the tissue; disconnecting the energy source from the IRE probe and withdrawing the probe. More specifically, the invention involves ablating diseased portions of lung tissue. Although the method of the present invention is directed towards treatment of a diseased lung, the method can also be used to treat other organs or areas of tissue to include, but not limited to areas of the digestive, skeletal, muscular, nervous, endocrine, circulatory, reproductive, lymphatic, urinary, or other soft tissue or organs; and more particularly, areas of the liver, prostate, kidney, pancreas, uterus and brain, among others.

DETAILED DESCRIPTION OF THE INVENTION

Figure 1:
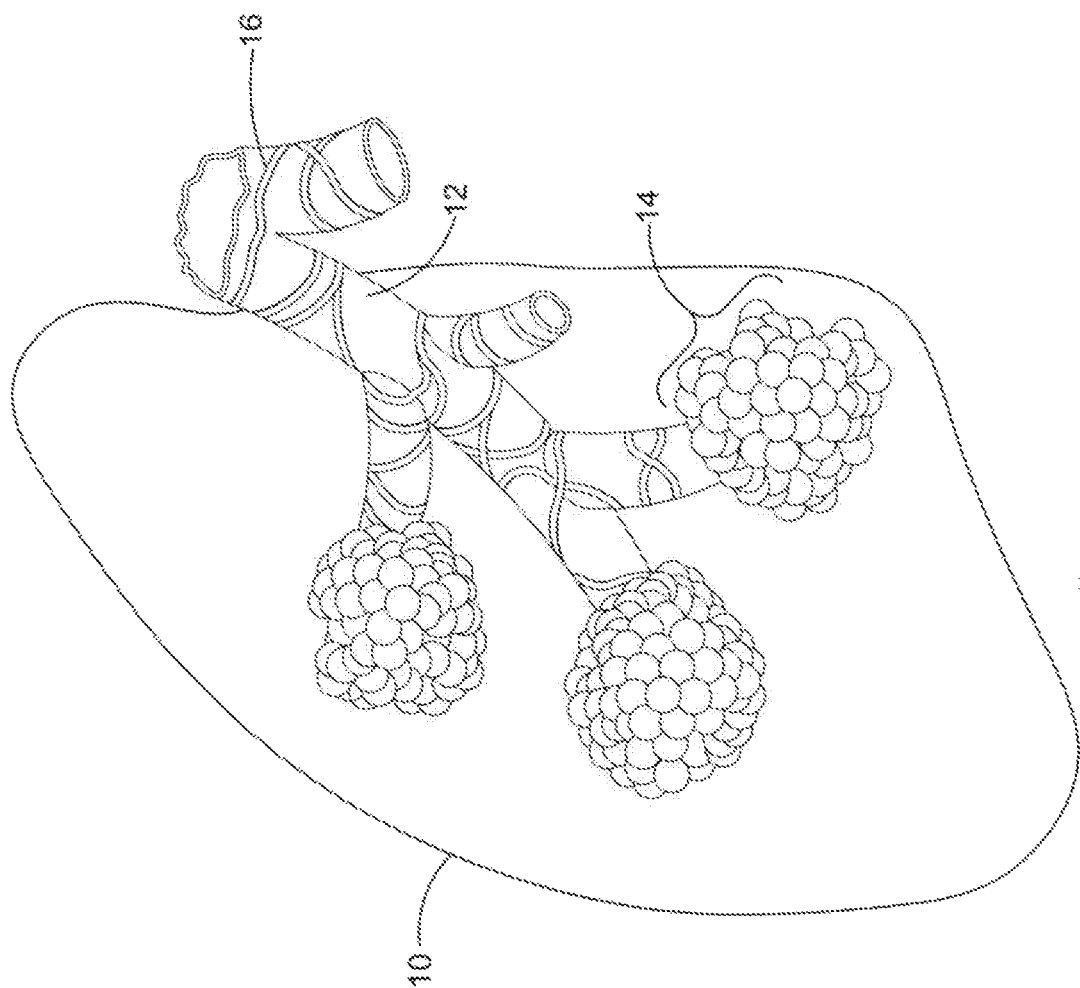
FIG. 1 is a perspective view of a lowermost portion of the lung depicting an enlarged bronchus and alveoli.
Figure 2A:
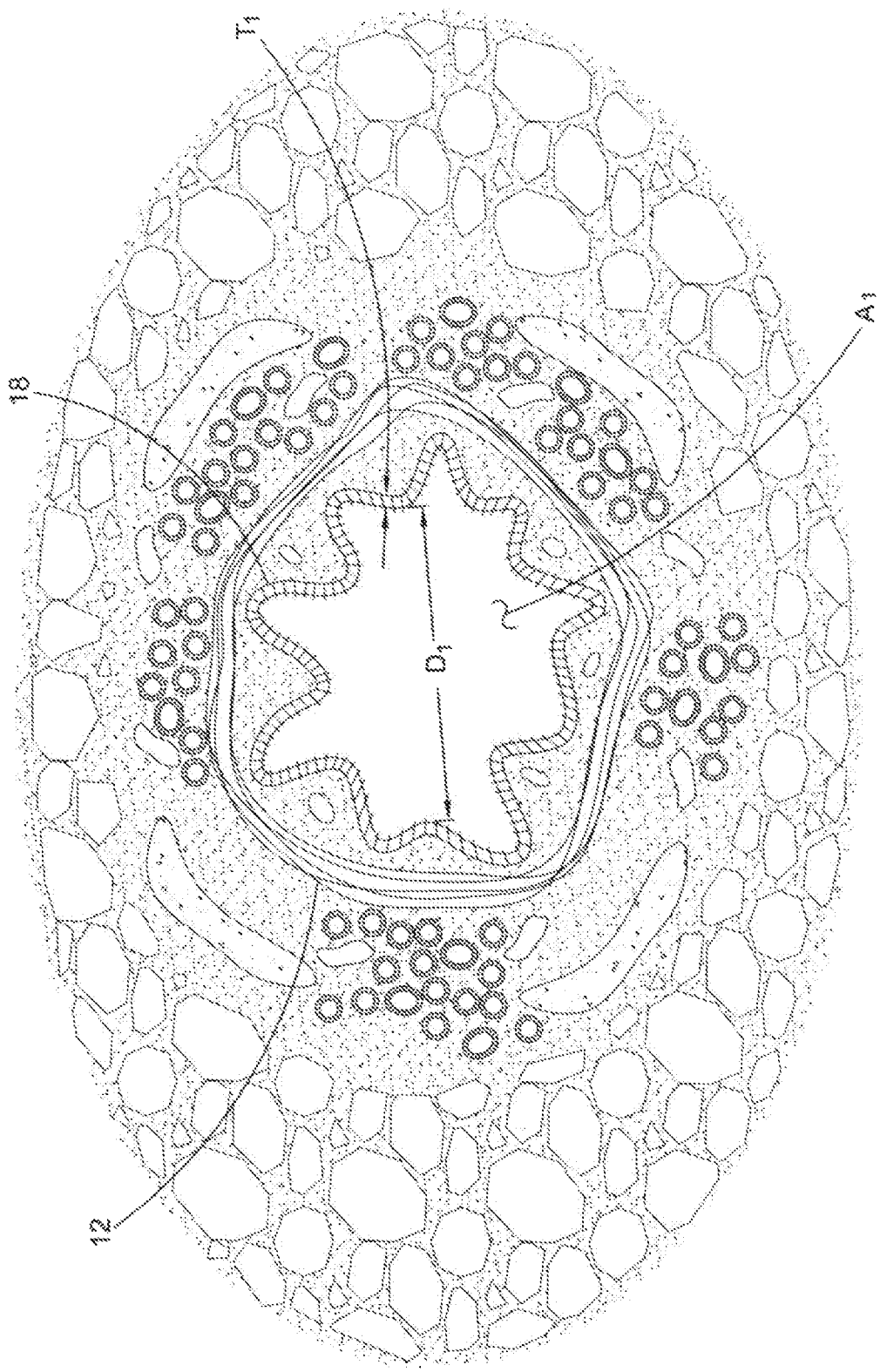
FIG. 2A is an enlarged cross-sectional view of a normal bronchus.
Figure 2B:
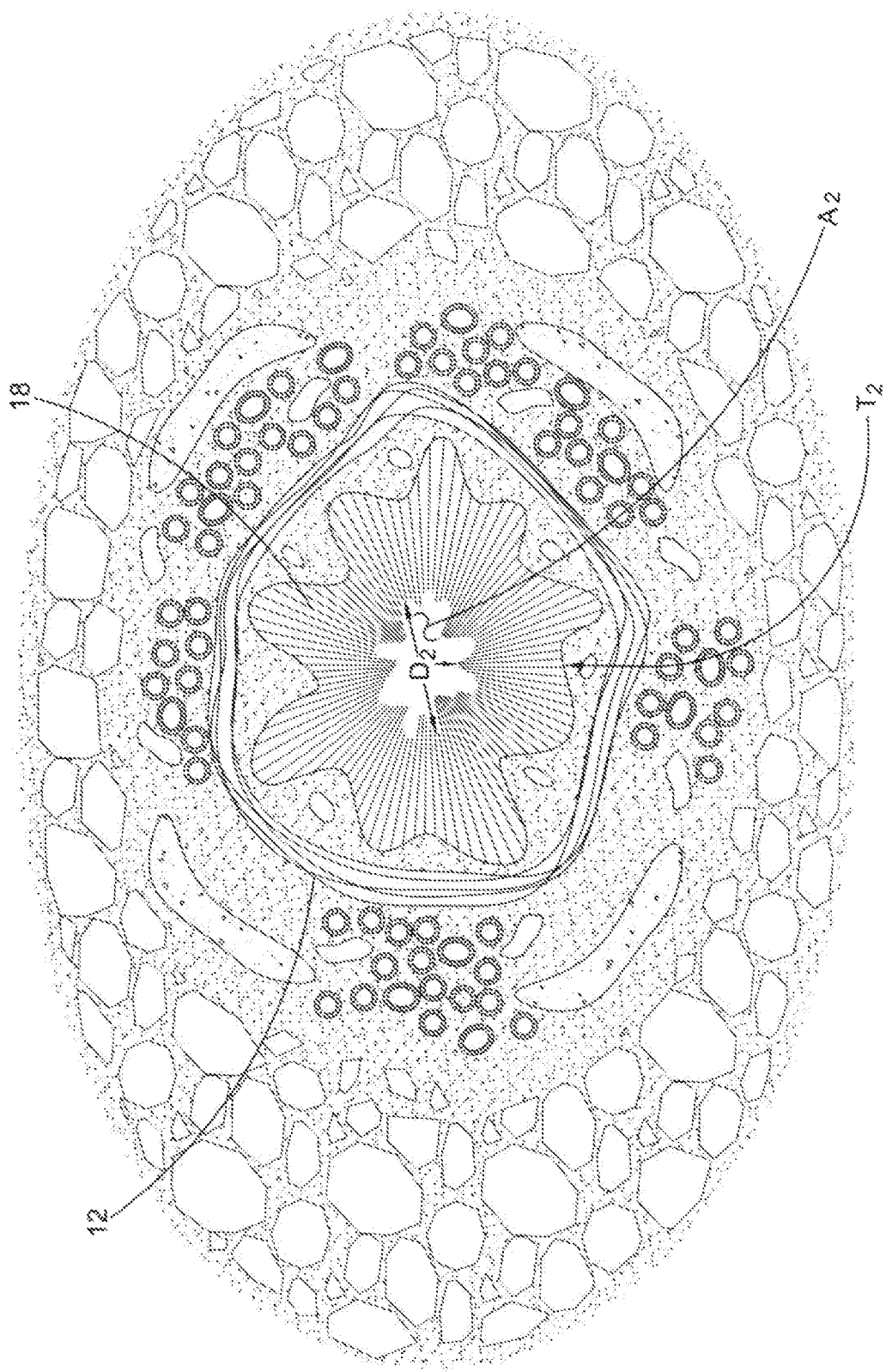
FIG. 2B is an enlarged cross-sectional view of a bronchus affected by chronic bronchitis.
Figure 3A:
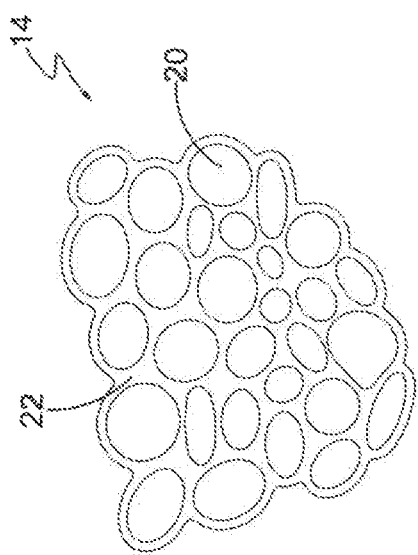
FIG. 3A is an enlarged cross-sectional view of normal alveoli.
Figure 3B:
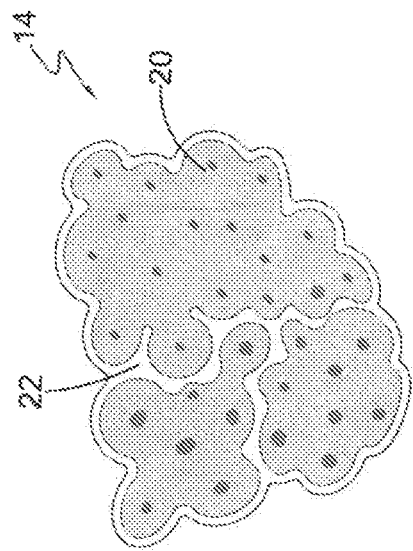
FIG. 3B is an enlarged cross-sectional view of alveoli affected by emphysema.
Figure 4:
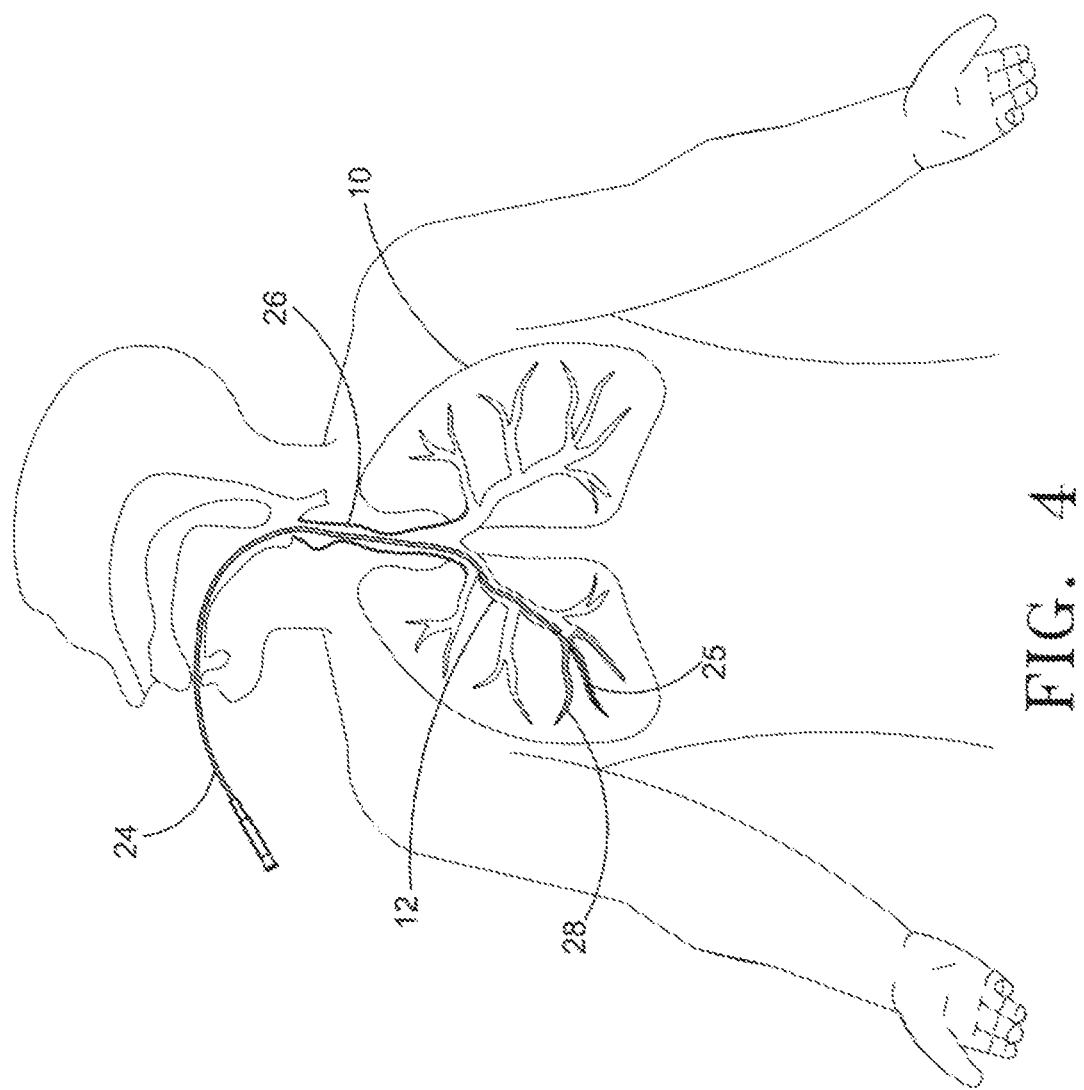
FIG. 4 is a perspective view of the endotracheal procedure for performing IRE on a lung affected by chronic bronchitis showing a catheter passed through the trachea and positioned within the bronchus.

FIG. 4 shows the endotracheal method of performing IRE on a lung (10) affected by chronic bronchitis. A catheter (24) is advanced through the trachea (26) to a diseased region (28) of the bronchus (12). Advancement through the trachea (26) is relatively simple and will optionally require a guidewire to select the advancement route through to the branching bronchus (12). Steering of the catheter (24) may be effected under real time imaging using video assisted thoracic surgery (VATS). Once the catheter (24) is in place inside the diseased region (28), a flexible IRE device (25) is inserted through the catheter (24) to the diseased region (28) of the bronchus (12). The flexible IRE device is used in the endotracheal method because it allows for the device to be easily steered through and properly positioned within the delicate intricacies of the lung (10) and into the bronchus (12). With the flexible IRE device (25) within the diseased region (28) of the lung (10), an IRE power source (not shown) is powered on and IRE energy is applied to ablate the inflamed bronchial tissue of the diseased region (28). To treat multiple bronchi, the IRE device (25) may then be retracted back into the catheter (24) and redeployed in an adjacent bronchus (12).

Figure 5A:
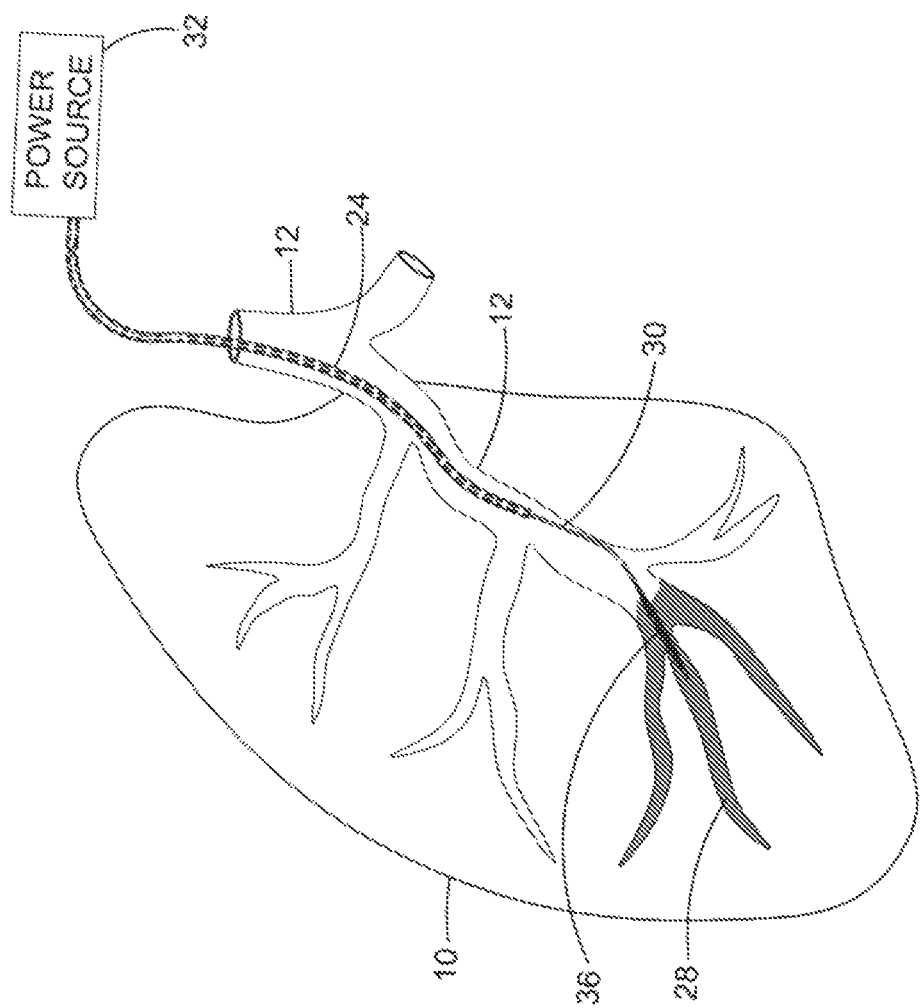
FIG. 5A is a perspective view of the endotracheal procedure for performing IRE on a lung affected by chronic bronchitis showing an IRE electrode balloon positioned within the bronchus.
Figure 5B:
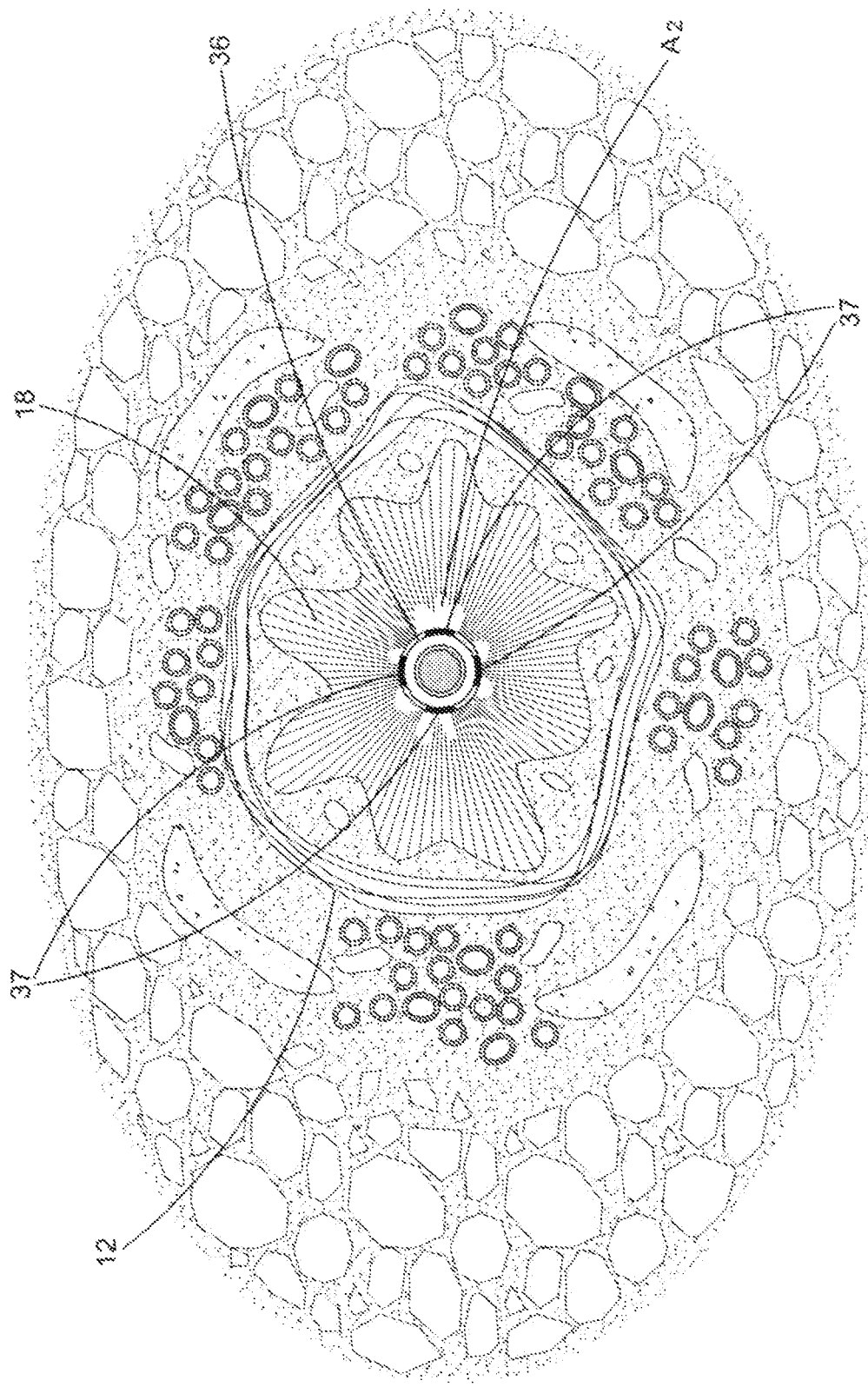
FIG. 5B is an enlarged cross-sectional view of a deflated IRE electrode balloon positioned within the bronchus prior application of IRE energy.
Figure 5C:
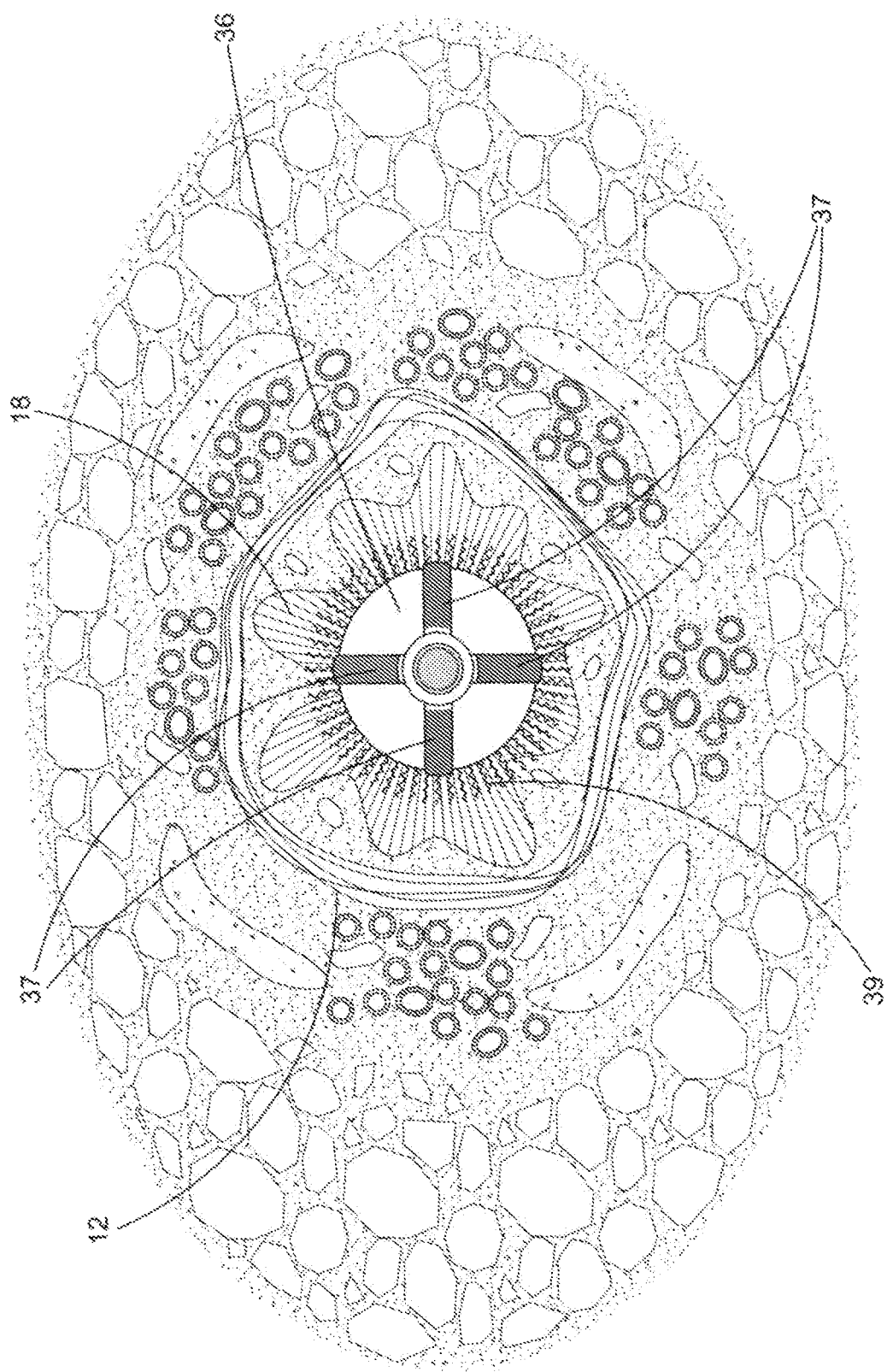
FIG. 5C is an enlarged cross-sectional view of an inflated IRE electrode balloon positioned within the bronchus during the application of IRE energy.
Figure 5D:
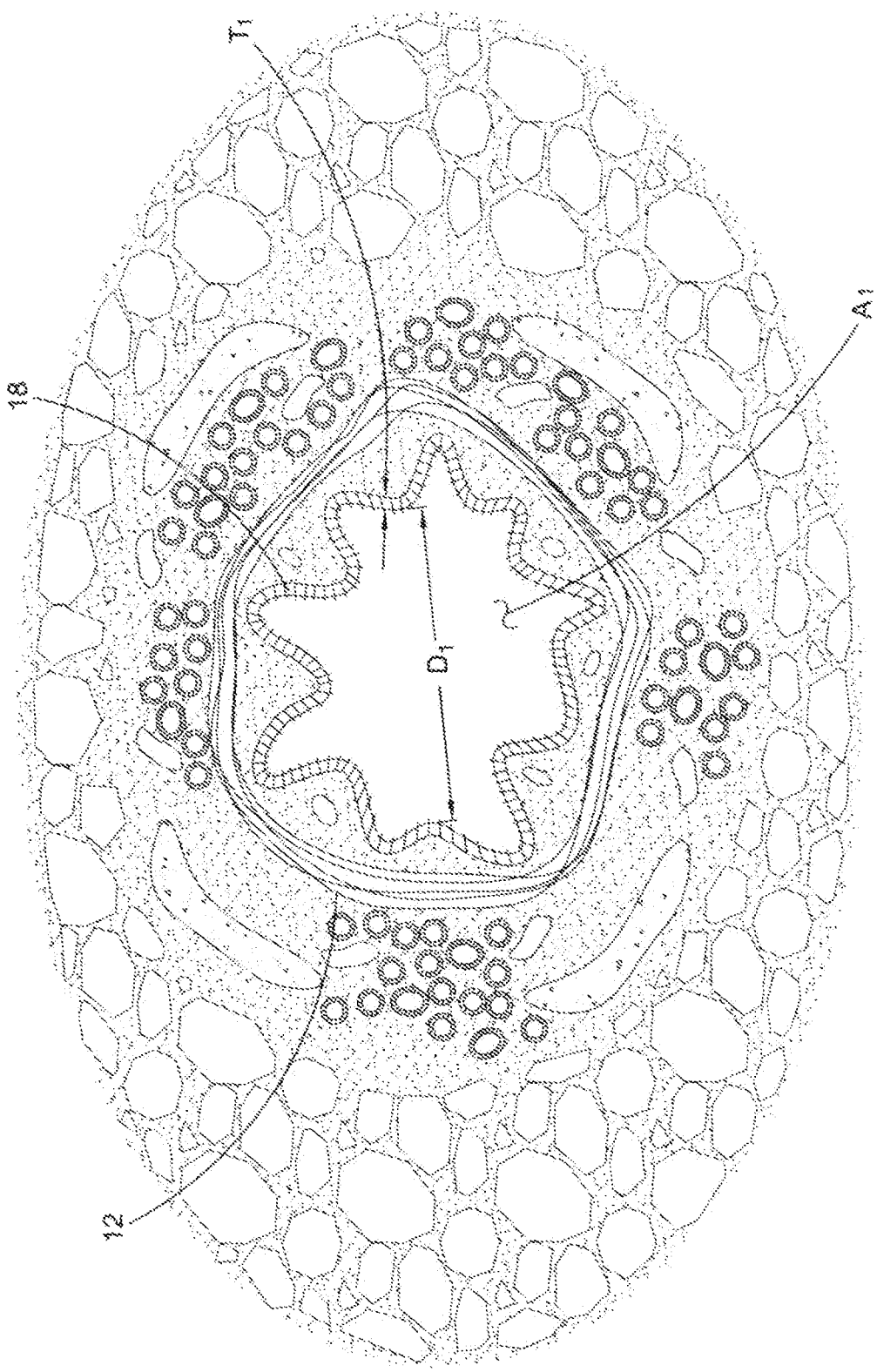
FIG. 5D is an enlarged cross-sectional view of the bronchus post-treatment showing the restored diameter of the bronchus.

The endotracheal method of performing IRE can be executed endo-bronchially or exo-bronchially. FIG. 5A shows a more detailed view of the flexible IRE device (30) in place within the diseased region (28) of the lung (10) wherein the IRE device (30) includes an electrode balloon (36). Although an electrode balloon is shown, the endotracheal procedure is not limited to such, other devices may be employed. FIG. 5B details the electrode balloon (36), in a deflated state, in place within the decreased diameter airway (A2) of the inflamed inner bronchial wall (18) of the bronchus (12). The electrode balloon (36) includes a plurality of electrodes 37 positioned on the surface of the deflated balloon. Prior to application of IRE energy, the IRE power source (32) is powered on, the electrode balloon (36) is inflated as shown in FIG. 5C. The expansion of the balloon results in a partial increase in bronchial airway diameter. Electrodes 37 are shown in contact with the inner bronchial wall (18) of the bronchus. As IRE energy is then applied to the inner bronchial wall (18) of the bronchus, electrical current (39) flows from the electrodes (37) into the bronchial wall (18) tissue. The inflamed portion of the bronchus is ablated, reducing the thickness of the bronchus wall. After treatment, the diameter (D1) of bronchial airway (A1) increases as shown in FIG. 5D. The airflow is restored and breathing functions improve.

A percutaneous method of treating a lung affected by chronic bronchitis may also be used. Very much similar to the endotracheal method, the percutaneous method may be executed both endo-bronchially and exo-bronchially. The probe, with increased rigidity and strength relative to an IRE catheter probe, is inserted into the lung tissue through the skin using a direct stick approach. The distal end section of the probe is then advanced through a wall of the bronchus into the lumen. IRE energy is applied to ablate the tissue of the diseased region such that inflammation of the bronchus is decreased and breathing functions are enhanced.

Figure 6A:
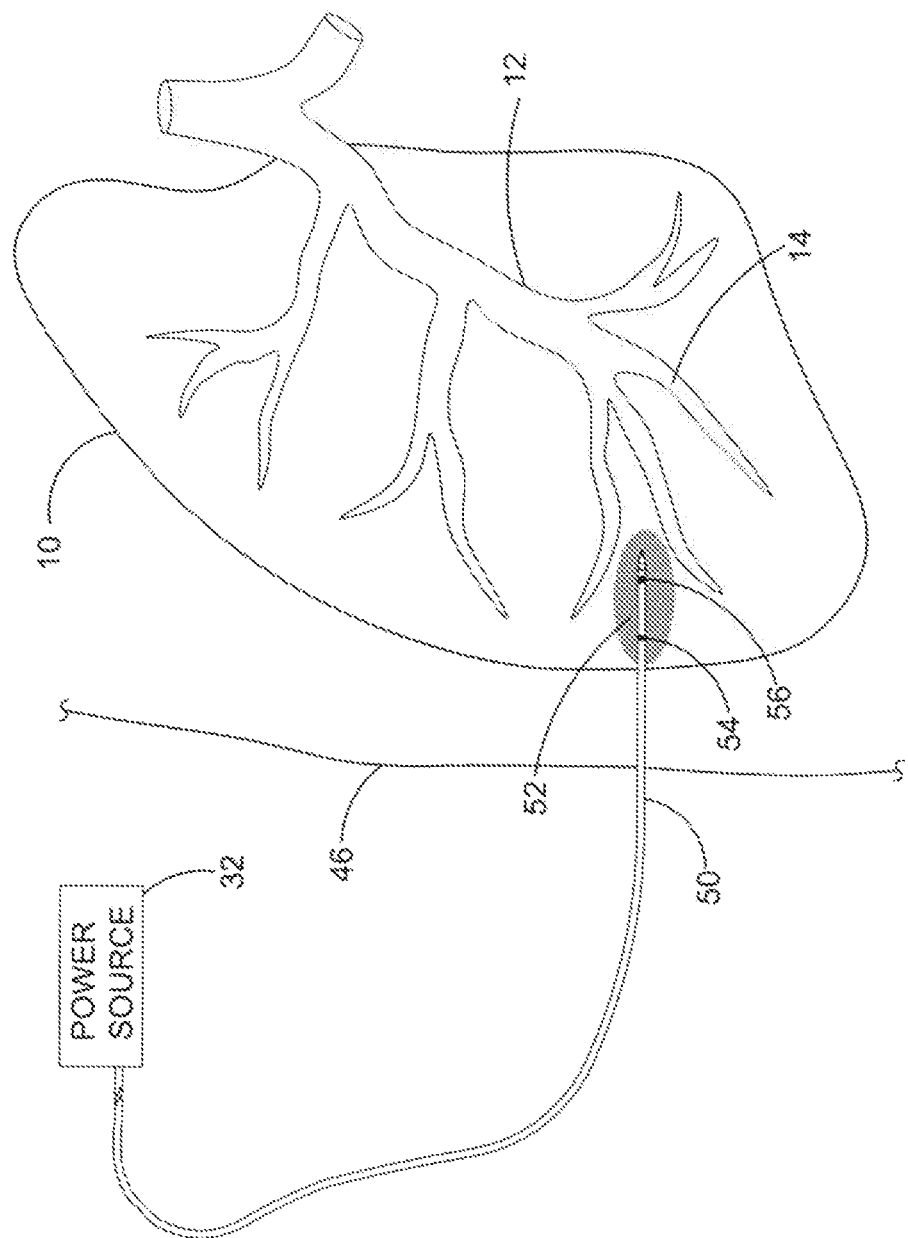
FIG. 6A is a perspective view of the percutaneous procedure of performing IRE detailing the use of an IRE probe to ablate the diseased region of the lung.
Figure 6B:
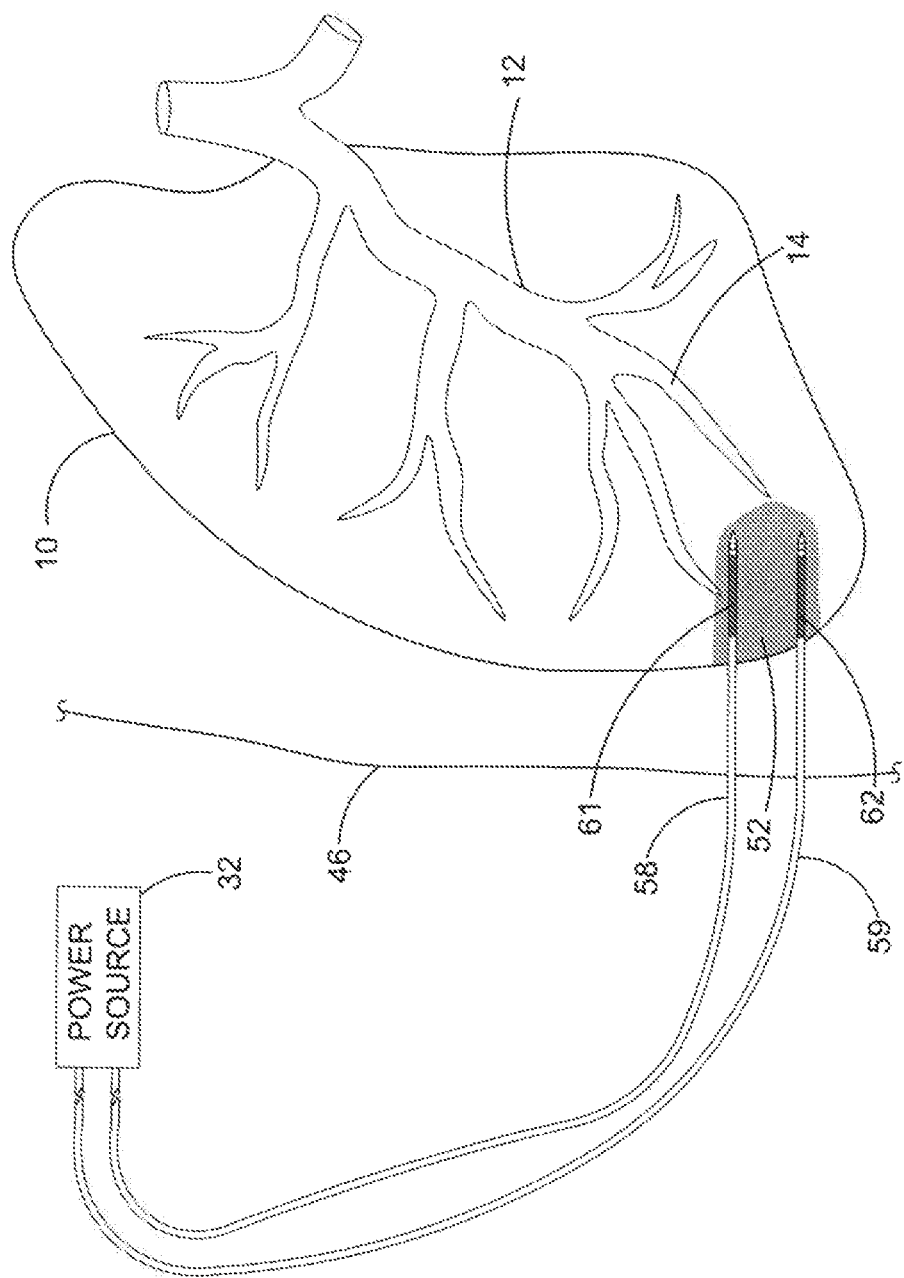
FIG. 6B is a perspective view of the percutaneous procedure of performing IRE detailing the use of two IRE probes to ablate the diseased region of the lung.

FIGS. 6A and 6B show a method of performing IRE on an emphysemic lung (10) using a percutaneous approach. Although not shown, the endotracheal approach previously described may also be used. FIG. 6A details a bipolar IRE probe (50) inserted through the skin (46) to the target area of the lung (10) near the alveoli (14). Advancement and positioning of the probe (50) may be effected under real time imaging modalities such as ultrasound or CT. Once the probe (50) is in place in the targeted lung region, the IRE power source (32) is powered on and IRE energy is applied to the probe. Electrical current flows between distal electrode (56) and proximal electrode (54), creating a zone of ablation (52).

Alternatively, as shown in FIG. 6B, two IRE probes of opposite polarity may be used to ablate a desired lung tissue volume. Electrode probe (58), which may be of positive polarity, is positioned within the lung tissue a selected distance away from negative electrode probe (59). The application of electrical energy from power source (32) creates an electrical field between the two electrodes 61 and 62 as shown by ablation zone (52). In another embodiment (not shown), an electrode probe with deployable electrode tines may be used to apply IRE energy to lung tissue. In all these embodiments, the ablated tissue dies, thereby reducing the overall lung volume. For larger target areas, sequential ablations may be performed. As with LVRS, up to approximately 20-35% of the damaged lung may be non-surgically ablated. By reducing the lung volume, the remaining lung tissue and surrounding muscles are able to work more efficiently, improving air flow.

Ablation of the targeted region of diseased tissue is achieved with an IRE generator as the power source, utilizing a standard wall outlet of 110 volts (v) or 230 v with a manually adjustable power supply depending on voltage. The generator should have a voltage range of 100 v to 10,000 v and be capable of being adjusted at 100 v intervals. The applied ablation pulses are typically between 20 and 100 microseconds in length, and capable of being adjusted at 10 microsecond intervals. The preferred generator should also be programmable and capable of operating between 2 and 50 amps, with test ranges involving an even lower maximum where appropriate. It is further desired that the IRE generator includes 2 to 6 positive and negative connectors, though it is understood that the invention is not restricted to this number of connectors and may pertain to additional connector combinations and amounts understood in the art and necessary for optimal configurations for effective ablation. Preferably, IRE ablation involves 90 pulses with maximum field strengths of 400 V/cm to 3000 V/cm between electrodes. Pulses are applied in groups or pulse-trains where a group of 1 to 15 pulses are applied in succession followed by a gap of 0.5 to 10 seconds. Pulses can be delivered using probes, needles, and electrodes each of varying lengths suitable for use in not only with percutaneous and laparoscopic procedures, but with open surgical procedures as well. In endotracheal procedures, due to the delicate intricacies and general make-up of the lung, it is preferable that a flexible device be used to ensure proper placement and reduced risk of perforation, abrasion, or other trauma to the lung tissue.

Although preferred specifics of IRE ablation devices are set forth above, electro-medicine provides for ablation processes that can be performed with a wide range of variations. For instance, some ablation scenarios can involve 8 pulses with maximum field strengths between electrodes of 250 V/cm to 500 V/cm, while others require generators having a voltage range of 100 kV-300 kV operating with nano-second pulses with maximum field strengths of 2,000 V/cm to, and in excess of, 20,000 V/cm between electrodes. Electrodes can be made using a variety of materials, sizes, and shapes known in the art, and may be spaced at an array of distances from one another. Conventionally, electrodes have parallel tines and are square, oval, rectangular, circular or irregular shaped; having a distance of 0.5 to 10 centimeters (cm) between two electrodes; and a surface area of 0.1 to 5 cm2.

Figure 7:
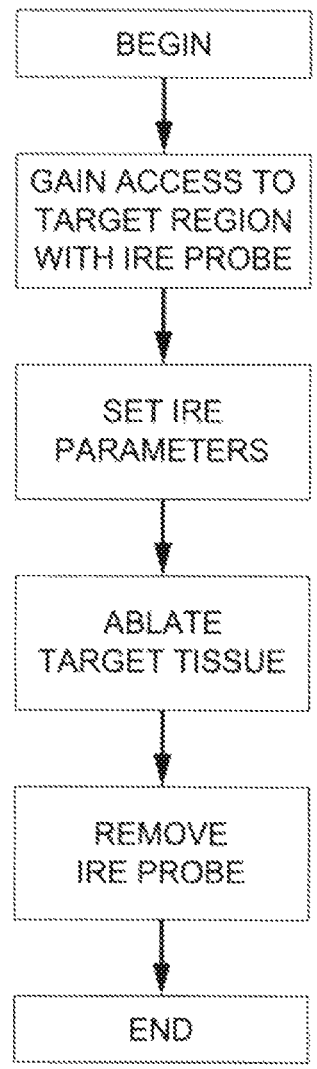
FIG. 7 is a flowchart showing the method of treating patients with COPD or chronic bronchitis using IRE ablation.

FIG. 7 is a flowchart detailing the basic method of performing IRE ablation on bronchitis or COPD patients. As detailed above, access to the diseased region is gained through open surgical, laparoscopical, percutaneous or endotracheal procedure. Once the IRE device is connected and in proper position, the IRE parameters are set. These parameters may vary and are selected depending upon several factors such as the diseased state, patient health and anatomy, and other considerations. After establishing and setting the required IRE energy parameters, the diseased region of the lung is ablated and the IRE device is removed. Thus, focal tissue ablation of the lung is achieved without causing harm to surrounding tissue and/or organs.

An unlimited number of variations and configurations for the present invention could be realized. The foregoing discussion describes merely exemplary embodiments illustrating the principles of the present invention, the scope of which is recited in the following claims. Those skilled in the art will readily recognize from the description, the claims, and drawings that numerous changes and modifications can be made without departing from the spirit and scope of the invention. Accordingly, the scope of the invention is not limited to the foregoing specification.

What is claimed is:

1. A method to non-thermally ablate tissue to treat a lung disease, comprising:
   advancing a guide sheath to a first treatment zone in a lung of a patient;
   operatively coupling an expandable electrode to a generator, wherein the electrode comprises a deployed state and a collapsed state;
   operatively coupling a second electrode to the generator;
   expanding the electrode from the compressed state to the deployed state at the first treatment zone;
   activating the generator programmed to generate a first set of bipolar electrical pulses configured to be delivered through the deployed electrode to the first treatment zone, wherein the bipolar electrical pulses are configured to result in non-thermal ablation of tissue in the first treatment zone;
   collapsing the deployed electrode to the collapsed state;
   withdrawing the electrode while in the collapsed state back into the guide sheath;
   advancing the guide sheath and the collapsed electrode to a second treatment zone in the lung;
   expanding the electrode the deployed state at the second treatment zone;
   reactivating the generator programmed to generate a second set of bipolar electrical pulses configured to be delivered through the deployed electrode to the second treatment zone, wherein the bipolar electrical pulses are configured to result in non-thermal ablation of tissue in the second treatment zone.

2. The method of claim 1, wherein the guide sheath comprises a steerable endobronchial device.

3. The method of claim 1, wherein the step of advancing the guide sheath to the first treatment zone further comprises steering the guide sheath under imaging.

4. The method of claim 3, wherein the imaging further comprises using video assisted 1 magmg.

5. The method of claim 1, wherein the expandable electrode and the second electrode are both monopolar electrodes.

6. The method of claim 1, wherein the expandable electrode further comprises a balloon and wherein the non-thermal ablation is irreversible electroporation.

7. The method of claim 1, wherein the electrode in the deployed state is configured to contact a target tissue in both the first treatment zone and the second treatment zone.

8. The method of claim 1, wherein the lung disease comprises any of the following: congestive obstructive pulmonary disease (COPD), emphysema, chronic bronchitis, bronchitis, inflammation of the lung airways, or clogged mucus in the bronchial tubes.

9. A method to non-thermally ablate lung tissue comprising:
advancing a guide device to a first treatment zone in the lung; operatively coupling an expandable electrode to a generator;
expanding the electrode from a collapsed state to a deployed state at the first treatment zone;
operatively coupling a second electrode to the generator;
activating the generator programmed to generate a first set of bipolar electrical pulses configured to be delivered through the deployed electrode to the first treatment zone, wherein the bipolar electrical pulses are configured to result in non-thermal ablation of cells in the first treatment zone;
collapsing the electrode from the deployed state to the collapsed state;
retracting the collapsed electrode back into the guide device;
advancing both the guide device and the collapsed electrode to a second treatment zone in the lung;
expanding the electrode from the collapsed state to the deployed state at the second treatment zone;
reactivating the generator programmed to generate a second set of bipolar electrical pulses configured to be delivered through the deployed electrode to the second treatment zone, wherein the bipolar electrical pulses are configured to result in non-thermal ablation of cells in the second treatment zone.

10. The method of claim 9, wherein the expandable electrode and the second electrode are both monopolar electrodes.

11. The method of claim 10, wherein the expandable electrode in the deployed state is configured to contact a target tissue in both the first treatment zone and the second treatment zone.

12. The method of claim 11, wherein the expandable electrode is a balloon and the non-thermal ablation is irreversible electroporation.

13. A method to non-thermally ablate lung tissue affected by bronchitis, comprising:
advancing an endobronchial device to a first treatment zone in the lung;
operatively coupling a deployable electrode and a non-deployable electrode to a generator;
expanding the deployable electrode from a collapsed state to a deployed state at the first treatment zone;
activating the generator programmed to generate a first set of bipolar electrical pulses configured to be delivered through the deployed electrode to the first treatment zone, wherein the bipolar electrical pulses are configured to result in non-thermal ablation of tissue affected by bronchitis in the first treatment zone;
collapsing the electrode from the deployed state to the collapsed state;
retracting the collapsed electrode back into the endobronchial device;
advancing both the endobronchial device and the collapsed electrode to a second treatment zone in the lung;
expanding the electrode from the collapsed state to the deployed state at the second treatment zone;
reactivating the generator programmed to generate a second set of bipolar electrical pulses configured to be delivered through the deployed electrode to the second treatment zone, wherein the bipolar electrical pulses are configured to result in non-thermal ablation of tissue affected by bronchitis in the second treatment zone.

14. The method of claim 13, wherein the deployable electrode and the non-deployable electrode are monopolar electrodes.

15. The method of claim 13, wherein the deployable electrode is a balloon and comprises bipolar electrodes.

16. The method of claim 13, wherein advancing the endobronchial device comprises any of the following procedures: a laparoscopical procedure, a percutaneous procedure, or an endotracheal procedure.

17. The method of claim 13, wherein the deployed electrode is configured to contact tissue affected by chronic bronchitis in both the first treatment zone and the second treatment zone.

18. The method of claim 13, wherein the step of advancing the endobronchial device to a first treatment zone further comprises steering the endobronchial device under video assisted 1 magmg.

* * * * *